US009150612B2

(12) United States Patent
Disney

(10) Patent No.: US 9,150,612 B2
(45) Date of Patent: Oct. 6, 2015

(54) RNA TARGETING COMPOUNDS AND METHODS FOR MAKING AND USING SAME

(75) Inventor: Matthew D. Disney, Williamsville, NY (US)

(73) Assignee: The Research Foundation of State University of New York, Amherst, NY (US)

(*) Notice: Subject to any disclaimer, the term of this patent is extended or adjusted under 35 U.S.C. 154(b) by 820 days.

(21) Appl. No.: 12/072,291

(22) Filed: Feb. 25, 2008

(65) Prior Publication Data

US 2008/0227213 A1    Sep. 18, 2008

Related U.S. Application Data

(60) Provisional application No. 60/903,212, filed on Feb. 23, 2007, provisional application No. 61/004,389, filed on Nov. 27, 2007.

(51) Int. Cl.
*C07K 4/00* (2006.01)
*C07D 249/04* (2006.01)
*A61K 31/7008* (2006.01)
*C07K 9/00* (2006.01)
*C07K 14/00* (2006.01)

(52) U.S. Cl.
CPC ............... *C07K 4/00* (2013.01); *A61K 31/7008* (2013.01); *C07D 249/04* (2013.01); *C07K 9/00* (2013.01); *C07K 14/001* (2013.01); *Y10T 436/143333* (2015.01)

(58) Field of Classification Search
CPC ........................................................ C07K 4/00
USPC .............................................. 514/2; 530/326
See application file for complete search history.

(56) References Cited

U.S. PATENT DOCUMENTS

| | | | | |
|---|---|---|---|---|
| 5,434,047 A | * | 7/1995 | Arnold, Jr. .......................... | 435/5 |
| 5,521,063 A | * | 5/1996 | Summerton et al. ......... | 435/6.12 |
| 5,539,082 A | * | 7/1996 | Nielsen et al. ................ | 530/300 |
| 5,635,383 A | * | 6/1997 | Wu et al. ........................ | 435/458 |
| 5,656,609 A | * | 8/1997 | Wu et al. ...................... | 514/44 R |
| 5,714,331 A | * | 2/1998 | Buchardt et al. ................... | 435/6 |
| 5,728,518 A | * | 3/1998 | Carmichael ........................ | 435/5 |
| 5,811,387 A | | 9/1998 | Simon et al. | |
| 5,831,005 A | | 11/1998 | Zuckerman et al. | |
| 5,972,900 A | * | 10/1999 | Ferkol et al. ................ | 514/44 R |
| 6,083,741 A | * | 7/2000 | Hart et al. ................... | 435/320.1 |
| 6,150,168 A | * | 11/2000 | Woo et al. ...................... | 435/440 |
| 6,395,474 B1 | * | 5/2002 | Buchardt et al. ................... | 435/6 |
| 7,030,216 B2 | * | 4/2006 | Horn et al. ..................... | 530/333 |
| 7,169,814 B2 | * | 1/2007 | Rothbard et al. ............. | 514/565 |
| 2003/0176670 A1 | | 9/2003 | Griffin et al. | |
| 2012/0027677 A1 | * | 2/2012 | Peretz et al. ................... | 424/9.1 |

FOREIGN PATENT DOCUMENTS

WO    0214545 A2    2/2002
WO    2007016455 A2    2/2007

OTHER PUBLICATIONS

Huq (Biochem 38, 5172-77, 1999).*
Prathiba, J. et al. Probing RNA-Antibiotic Interactions: A FTIR Study, Molecular Biology Reports, Mar. 2008, vol. 35, pp. 51-57.
Metallo, Steven J. et al. Using Bifunctional Polymers Presenting Vancomycin and Fluorescein Groups to Direct Anti-Fluorescein Antibodies to Self-Assembled Monolayers Presenting D-Alanine-D-Alanine Groups, J. Am. Chem. Soc., Mar. 20, 2003, vol. 125, pp. 4534-4540.
Thomas, Jason R. et al. Biochemical and Thermodynamic Characterization of Compounds that Bind to RNA Hairpin Loops: Towards and Understanding of Selectivity, Biochemistry, Sep. 1, 2006, vol. 45, No. 36, pp. 10928-10938.
Kanadia et al. Reversal of RNA Missplicing and Myotonia after Muscleblind Overexpression in a Mouse poly (CUG) Model for Myotonic Dystrophy, PNAS, Aug. 1, 2006, vol. 103, No. 31, pp. 11748-11753.
Henklein et al., "5-Norbornene-2,3-dicarboximido Carbonochloridate. A New Stable Reagent for the Introduction of Amino-Protecting Groups," Synthesis, 1987:166-167 (1987).
Woese et al., "Secondary Structure Model for Bacterial 16S Ribosomal RNA: Phylogenetic, Enzymatic and Chemical Evidence," Nucleic Acids Res., 8:2275-2293 (1980).
Zaug et al., "The Intervening Sequence RNA of Tetrahymena is an Enzyme," Science, 231:470-475 (1986).
Zuckermann et al., "Efficient Method for the Preparation of Peptoids |Oligo(N-Substituted Glycines)| by Submonomer Solid-Phase Synthesis ," J. Am. Chem. Soc., 114(26):10646-10647 (1992).
Joyce, "In vitro evolution of nucleic acids," Curr. Opin. Struct. Biol., 4:331-336 (1994).
Klug et al., "All You Wanted to Know About SELEX," Mol. Biol. Rep., 20:97-107 (1994).
Roestamadji et al., "Loss of Individual Electrostatic Interactions Between Aminoglycoside Antibiotics and Resistance Enzymes as an Effective Means to Overcoming Bacterial Drug Resistance," J. Am. Chem. Soc., 117:11060-11069 (1995).

(Continued)

*Primary Examiner* — David Lukton
(74) *Attorney, Agent, or Firm* — Hodgson Russ LLP

(57) ABSTRACT

Disclosed are RNA targeting compounds having the formula:

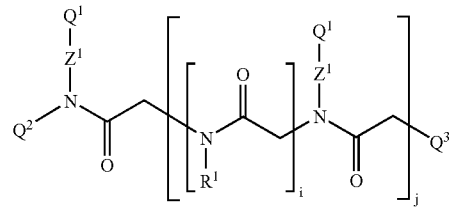

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ represents the same or different RNA binding ligand; $Q^2$ is an alkyl group; $Q^3$ is a halogen, an alkyl group, an aryl group, or an amine. Also disclosed are RNA targeting compounds that include a polymer backbone and two or more pendant RNA binding ligands that are bound to the polymer backbone. Methods for using the subject RNA targeting compounds to treat myotonic dystrophy and other diseases are also disclosed, as are compounds that can be used to prepare the subject RNA targeting compounds.

32 Claims, 12 Drawing Sheets

(56) References Cited

OTHER PUBLICATIONS

Fourmy et al., "Structure of the A Site of *Escherichia coli* 16S Ribosomal RNA Complexed With an Aminoglycoside Antibiotic," Science, 274:1367-1371 (1996).
Hamy et al., "An Inhibitor of the Tat/TAR RNA Interaction That Effectively Suppresses HIV-1 Replication," Proc. Natl. Acad. Sci. U.S.A., 94:3548-3553 (1997).
Weber et al., "A Fast and Inexpensive Method for N-Terminal Fluorescein-Labeling of Peptides," Bioorg. Med. Chem. Lett., 8:597-600 (1998).
Batey et al., "Tertiary Motifs in RNA Structure and Folding," Angew. Chem., Int. Ed. Engl., 38:2326-2343 (1999).
Griffey et al., "Determinants of Aminoglycoside-Binding Specificity for rRNA by Using Mass Spectrometry," Proc. Natl. Acad. Sci. U.S. A., 96:10129-10133 (1999).
MacBeath et al., "Printing Small Molecules as Microarrays and Detecting Protein-ligand Interactions En Masse," J. Am. Chem. Soc., 121:7967-7968 (1999).
Mathews et al. "Expanded Sequence Dependence of Thermodynamic Parameters Improves Prediction of RNA Secondary Structure," J. Mol. Biol., 288:911-940 (1999).
Disney et al., "Targeting a Pneumocystis Carinii Group I Intron With Methylphosphonate Oligonucleotides: Backbone Charge is Not Required for Binding or Reactivity," Biochemistry, 39:6991-7000 (2000).
Doudna, "Structural Genomics of RNA," Nat. Struct. Biol., 7 (Suppl.):954-956 (2000).
Mankodi et al., "Myotonic Dystrophy in Transgenic Mice Expressing an Expanded CUG Repeat," Science, 289:1769-1772 (2000).
Miller et al., "Recruitment of Human Muscleblind Proteins to (CUG)n Expansions Associated with Myotonic Dystrophy," EMBO J., 19:4439-4448 (2000).
Satz et al., "Synthesis of Fluorescent Microgonotropens (FMGTs) and Their Interactions with dsDNA," Bioorg. Med. Chem., 8(8):1871-1880 (2000).
Tian et al., "Expanded CUG Repeat RNAs Form Hairpins That Activate the Double-Stranded RNA-Dependent Protein Kinase PKR," RNA 6:79-87 (2000).
Gallego et al., "Targeting RNA with Small Molecule Drugs: Therapeutic Promise and Chemical Challenges," Acc. Chem. Res., 34:836-843 (2001).
Kolb et al., "Click Chemistry: Diverse Chemical Function from a Few Good Reactions," Angew. Chem., Int. Ed. Engl., 40:2004-2021 (2001).
Lagos-Quintana et al., "Identification of Novel Genes Coding for Small Expressed RNAs," Science, 294:853-858 (2001).
Mankodi et al., "Muscleblind Localizes to Nuclear Foci of Aberrant RNA in Myotonic Dystrophy Types 1 and 2," Hum. Mol. Genet., 10:265-2170 (2001).
Mankodi et al., "Myotonic Syndromes," Curr. Opin. Neurol., 15:545-552 (2002).
Swayze et al., "SAR by MS: A Ligand Based Technique for Drug Lead Discovery Against Structured Rna Targets," J. Med. Chem. ,45:3816-3819 (2002).
Winkler et al., "Thiamine Derivatives Bind Messenger RNAs Directly to Regulate Bacterial Gene Expression," Nature, 419:952-956 (2002).
Carter et al., "X Functional Insights From the Structure of the 30S Ribosomal Subunit and its Interactions With Antibiotics," Nature, 407:340-348 (2003).
Johnson et al., "Application of NMR Shapes Screening to an RNA Target," J. Am. Chem. Soc., 125:15724-15725 (2003).
Kanadla et al., "A Muscleblind Knockout Model for Myotonic Dystrophy," Science, 302:1978-1980 (2003).
Kolb et al., "The Growing Impact of Click Chemistry on Drug Discovery," Drug Discovery Today, 8:1128-1137 (2003).
Lynch et al., "Comparison of X-ray Crystal Structure of the 30S Subunit-Antibiotic Complex with NMR Structure of Decoding Site Oligonucleotide-Paromomycin Complex," Structure, 11:43-53 (2003).
Chan et al., "Polytriazoles as Copper(1)-Stabilizing Ligands in Catalysis," Org. Lett., 6:2853-2855 (2004).
Denap et al., "Combating Drug-Resistant Bacteria: Small Molecule Mimics of Plasmid Incompatibility as Antiplasmid Compounds," J. Am. Chem. Soc., 126:15402-15404 (2004).
Disney et al. "Aminoglycoside Microarrays to Explore Interactions of Antibiotics with RNAs and Proteins," Chemistry, 10:3308-3314 (2004).
Disney et al.,"Aminoglcoside Microarrays to Study Antibiotic Resistance," Angew. Chem. Int. Ed. Engl.,43:1591-1594 (2004).
Disney et al., "The Use of Carbohydrate Microarrays to Study Carbohydrate-Cell Interactions and to Detect Pathogens," Chem. Biol., 11:1701-1707 (2004).
He et al., "Synthesis and Evaluation of Novel Bacterial rRNA-Binding Benzimidazoles by Mass Spectrometry," Bioorg. Med. Chem. Lett., 14:695-699 (2004).
Kaul et al., "Fluorescencebased Approach for Detecting and Characterizing Antibiotic-Induced Conformational Changes in Ribosomal RNA: Comparing Aminoglycoside Binding to Prokaryotic and Eukaryotic Ribosomal RNA Sequences," J. Am. Chem. Soc., 126:3447-3453 (2004).
Mathews et al., "Incorporating Chemical Modification Constraints into a Dynamic Programming Algorithm for Prediction of RNA Secondary Structure," Proc. Natl. Acad. Sci. U.S.A., 101:7287-7292 (2004).
Ratner et al., "Tools for Glycomics: Mapping Interactions of Carbohydrates in Biological Systems," ChemBioChem, 5: 1375-1383 (2004).
Shandrick et al., "Monitoring Molecular Recognition of the Ribosomal Decoding Site," Angew. Chem., Int. Ed. Engl., 43: 3177-3182 (2004).
Gao et al., "Regio- and Chemoselective 6'-N-Derivatization of Aminoglycosides: Bisubstrate Inhibitors as Probes to Study Aminoglycoside 6'-N-Acetyltransferases," Angew. Chem. Int. Ed., 44(42):6859-6862 (2005).
Jang et al., "Click to Fit: Versatile Polyvalent Display on a Peptidomimetic Scaffold," Org. Lett., 7:1951-1954 (2005).
Seth et al., "SAR by MS: Discovery of a New Class of RNA-binding Small Molecules for the Hepatitis C Virus: Internal Ribosome Entry Site IIA Subdomain," J. Med. Chem., 48:7099-7102 (2005).
Thomas et al., "Size-Specific Ligands for RNA Hairpin Loops," J. Am. Chem. Soc.,127:12434-12435 (2005).
Thomas et al., "The Relationship Between Aminoglycosides' RNA Binding Proclivity and Their Antiplasmid Effect on an IncB Plasmid Combating Drug-Resistant Bacteria: Small Molecule Mimics of Plasmid Incompatibility as Antiplasmid Compounds," Biochemistry, 44:6800-6808 (2005).
Kaul et al., "Aminoglycosideinduced Reduction in Nucleotide Mobility at the Ribosomal RNA A-Site as a Potentially Key Determinant of Antibacterial Activity," J. Am. Chem. Soc., 128:1261-1271 (2006).
Lin et al., "Failure of MBNL 1-Dependent Post-Natal Splicing Transitions in Myotonic Dystrophy," Hum. Mol. Genet., 15:2087-2097 (2006).
Thomas et al., "Biochemical and Thermodynamic Characterization of Compounds That Bind to RNA Hairpin Loops: Toward an Understanding of Selectivity," Biochemistry, 45:10928-10938 (2006).
Childs-Disney et al., "A Small Molecule Microarray Platform to Select RNA Internal Loop-Ligand Interactions.," ACS Chem Biol., 2(11):745-754 (2007).
Disney et al., "An Aminoglycoside Microarray Platform for Directly Monitoring and Studying Antibiotic Resistance," Biochemistry, 40:11223-11230 (2007).
Disney et al., "Using Selection to Identify and Chemical Microarray to Study the RNA Internal Loops Recognized by 6'-N-Acylated Kanamycin A," ChemBioChem, 8(6):649-656 (2007).

* cited by examiner

43a R=n-propyl; n=4
43b R=n-propyl; n=8
43c R=n-propyl; n=12
43d R=n-propyl; n=16
44  R=methyl;  n=16

RNA TARGETING COMPOUNDS AND METHODS FOR MAKING AND USING SAME

The present application claims the benefit of U.S. Provisional Patent Application Ser. No. 60/903,212, filed Feb. 23, 2007, and of U.S. Provisional Patent Application Ser. No. 61/004,389, filed Nov. 27, 2007, which provisional patent applications is hereby incorporated by reference.

FIELD OF THE INVENTION

The present invention relates to methods and materials for systematically identifying RNA-ligand interactions, and, more particularly, to methods and materials that can be used to identify small molecules that target particular RNA motifs.

The present application cites a number of references, some or all of which are cited by number in square brackets. The references thus cited are listed in a section entitled "References" immediately before the claims. Each reference cited in this application, whether by number or otherwise, is hereby incorporated in its entirety, by reference.

BACKGROUND OF THE INVENTION

RNA forms complex tertiary structures that impart diverse functions [1, 2]. For example, RNA catalyzes reactions [3], regulates gene expression [4, 5], encodes protein, and plays other essential roles in biology. Therefore, RNA is an interesting and important target for developing drugs or probes of function [6, 7]. It is a vastly under-utilized target, however, mainly because of the limited information available on RNA ligand interactions that could facilitate rational design.

One advantage of using RNA as a drug target is that secondary structure information, which includes the motifs that comprise an RNA, can be easily obtained from sequence by free energy minimization [8, 9] or phylogenic comparison [10]. RNA tertiary structures are composites of the secondary structural motifs and the long-range contacts that form between them. Furthermore, RNA motifs can have similar properties both as isolated systems and as parts of larger RNAs. For example, aminoglycoside antibiotics affect the structure of the bacterial rRNA A-site similarly when they bind the entire ribosome or an oligonucleotide mimic of the bacterial rRNA A-site [11-16]. Studies on the binding of aminoglycosides and streptamine dimers to RNA hairpins [17-20] have facilitated the development of compounds to combat multidrug resistance by causing plasmid incompatibility [19, 20]. These results show that the identification of RNA motifs that bind small molecules can be useful for targeting the larger RNAs that contain them.

However, since RNA can adopt diverse structures, internal and hairpin loops for example, an understanding of how to target RNA with small molecules and other ligands has been elusive.

Illustrative methods to study and identify RNA ligand interactions include systematic evolution of ligands by exponential enrichment ("SELEX") [21, 22], structure-activity relationships ("SAR") by mass spectrometry ("MS") [23-26] and NMR [27], and chemical microarrays [28-30]. These methods probe RNA space (SELEX) or chemical space (SAR by MS and NMR and chemical microarrays) separately. However, these methods do not permit a systematic study of RNA-ligand interactions.

More recently, a method for systematically identifying RNA-ligand interactions has been developed. The method is described in, for example, Disney et al., "Using Selection to Identify and Chemical Microarray to Study the RNA Internal Loops Recognized by 6-N-Acylated Kanamycin A," *Chem Bio Chem*, 8:649-656 (2007); Childs-Disney et al., "A Small Molecule Microarray Platform to Select RNA Internal Loop-Ligand Interactions," *ACS Chem Biol.*, 2(11):745-754 (2007) (and in the associated Supporting Information (available on the internet at http://pubs.acs.org/subscribe/journals/acbcct/suppinfo/cb700174r/cb700174r-File003.pdf)); U.S. patent application Ser. No. 11/998,466 of Disney et al., filed Nov. 29, 2007; and PCT Patent Application No. PCT/US07/024,546 of Disney et al., filed Nov. 29, 2007, each of which is hereby incorporated by reference.

While aforementioned methods identify RNA-ligand interactions, there continues to be a need for compounds and associated methods and materials which exploit such RNA-ligand interactions, and the present invention is directed, in part, to addressing this need.

SUMMARY OF THE INVENTION

The present invention relates to an RNA targeting compound having the formula:

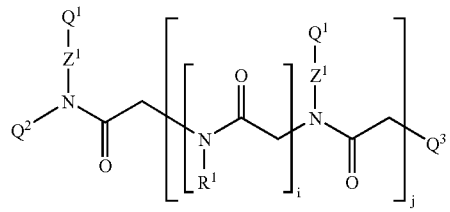

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ represents the same or different RNA binding ligand; $Q^2$ is an alkyl group; $Q^3$ is a halogen, an alkyl group, an aryl group, or an amine.

The present invention also relates to an RNA targeting compound comprising a polymer backbone and two or more pendant RNA binding ligands, wherein said two or more pendant RNA binding ligands are bound to said polymer backbone.

BRIEF DESCRIPTION OF THE DRAWINGS

FIG. 3A is a reaction scheme for making peptoid backbones that can be used to prepare various compounds of the present invention.

DETAILED DESCRIPTION OF THE INVENTION

Figure 1A:
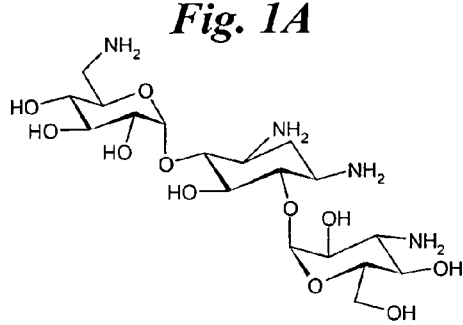
FIGS. 1A-1G are structural formulae of RNA binding ligands that can be used in the compounds of the present invention.

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as used herein, is meant to include unsubstituted alkyls, such as those set forth above, in which no atoms other than carbon and hydrogen are present. "Alkyl", as used herein, is also meant to include substituted alkyls. Suitable substituents include substituted or unsubstituted aryl groups (such as where the alkyl is a benzyl group or another aryl-substituted methyl group), heterocyclic rings (saturated or unsaturated and optionally substituted), alkoxy groups (which is meant to include aryloxy groups (e.g., phenoxy groups)), amine groups (e.g., unsubstituted, monosubstituted, or disubstituted with, for example, aryl or alkyl groups), guanidine and guanidinium groups (optionally substituted with, for example, one or more alkyl or aryl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl". Other suitable substituents include hydroxy groups and protected hydroxy groups (e.g., an acyloxy group, such at an acetoxy group; a silyl ether group, such as a trimethylsilyl ("TMS") ether group and a tert-butyldimethylsilyl ("TBS") ether group).

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e., —CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group.

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings, pyridiminyl rings, and furanyl rings. The aromatic rings can be optionally substituted. "Aryl" is also meant to include aromatic rings to which are fused one or more other aryl rings or non-aryl rings. For example, naphthyl groups, indole groups, isoindole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" is meant to include homocyclic or heterocyclic rings. The homocyclic or heterocyclic ring can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems, and such fused ring systems can be saturated or unsaturated, aromatic or non-aromatic. In the case where the ring is saturated (i.e., in the case where each of the atoms making up the ring are joined by single bonds to other members of the ring), the ring may optionally include unsaturated (aromatic or nonaromatic) or saturated substituents. Illustratively, the ring or ring system can contain 3, 4, 5, 6, 7, 8, 9, 10, or more members.

The present invention relates to an RNA targeting compound having the following Formula I:

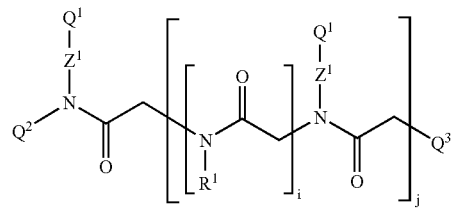

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ represents the same or different RNA binding ligand; $Q^2$ is an alkyl group; $Q^3$ is a halogen, an alkyl group, an aryl group, or an amine.

As used herein RNA targeting compound is meant to refer to a compound that binds to RNA. By way of illustration, the RNA targeting compound can bind to one or more RNA motifs, such as RNA repeat motifs and/or RNA structural motifs. "RNA structural motif", as used herein, is meant to refer to a targetable RNA internal loop, hairpin loop, bulge, or other targetable RNA structural motifs, for example, as described in Batey et al., "Tertiary Motifs in RNA Structure and Folding," *Angew. Chem. Int. Ed.,* 38:2326-2343 (1999), which is hereby incorporated by reference. Examples of RNA motifs include symmetric internal loops, asymmetric internal loops, 1×1 internal loops, 1×2 internal loops, 1×3 internal loops, 2×2 internal loops, 2×3 internal loops, 2×4 internal loops, 3×3 internal loops, 3×4 internal loops, 4×4 internal loops, 4×5 internal loops, 5×5 internal loops, 1 base bulges, 2 base bulges, 3 base bulges, 4 base bulges, 5 base bulges, 4 base hairpin loops, 5 base hairpin loops, 6 base hairpin loops, 7 base hairpin loops, 8 base hairpin loops, 9 base hairpin loops, 10 base hairpin loops, multibranch loops, pseudoknots, etc.

As noted above, j is an integer from 1 to 100. For example, j can be an integer from 1 to 50, from 1 to 20, from 1 to 10, from 2 to 100, from 2 to 50, from 2 to 20, from 2 to 10. Illustratively, j can be 1, 2, 3, 4, 5, 6, 7, 8, 9, 10, 11, 12, 13, 14, 15, 16, 17, 18, 19, or 20.

As noted above, each i is the same or different and is zero or an integer from 1 to 100, for example, zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, or 20. For example, when j is 1, there is one i value; when j is 2, there are two i values, and these two i values can be the same or they can be different; when j is 3, there are three i values, and these three i values can all be the same, they can all be different, or two can be the same and the other can be different; etc.

In certain embodiments, j is an integer from 2 to 10, and each i is the same or different and is zero or an integer from 1 to 20. In certain embodiments, each i is the same and is zero or an integer from 1 to 20. In certain embodiments, j is an integer from 2 to 10, and each i is the same and is zero or an integer from 1 to 20.

As noted above, each $R^1$ is the same or different and represents an alkyl group or an aryl group. For example, when j is 1 and i is 1, there is one $R^1$; when j is 1 and i is 2, or when j is 2 and each i is 1, or when j is 2 and one i is 2 and the other is zero, etc., there are two $R^1$'s, and these two $R^1$'s can be the same or they can be different; when j is 1 and i is 3, or when j is 3 and each i is 1, or when j is 2 and one i is 1 and the other i is two, or when j is 3 and one i is 3 and the other two i's are zero, etc., there are three $R^1$'s, and these three $R^1$'s can all be the same, they can all be different, or two can be the same and the other can be different; etc.

In certain embodiments, each $R^1$ is the same, as in the case where each $R^1$ is an unsubstituted methyl, ethyl, or propyl group. In certain embodiments, at least one $R^1$ is different, as in the case where all but one of the $R^1$'s are the same, all but two of the $R^1$'s are the same, all but three of the $R^1$'s are the same, all but two of the $R^1$'s are different, all but three of the $R^1$'s are different, some of the $R^1$'s are the same and others are different, etc. By way of illustration, in certain embodiments, at least one $R^1$ is an alkyl group and at least one $R^1$ is an aryl group; in certain embodiments, each $R^1$ is the same or different and is an alkyl group; in certain embodiments, each $R^1$ is the same or different and is an aryl group; in certain embodiments, each $R^1$ is the same or different and is an unsubstituted alkyl; in certain embodiments, each $R^1$ is the same or different and is a C1-C12 alkyl, such as a substituted C1-C12 alkyl or an unsubstituted C1-C12 alkyl; in certain embodiments, each $R^1$ is the same or different and is a C1-C6 alkyl, such as a substituted C1-C6 alkyl or an unsubstituted C1-C6 alkyl; in certain embodiments, each $R^1$ is the same or different and is a linear alkyl, such as a substituted linear alkyl or an unsubstituted linear alkyl, such as a C1-C12 unsubstituted linear alkyl, a C1-C6 unsubstituted linear alkyl, a C1-C4 unsubstituted linear alkyl, or a C1-C3 unsubstituted linear alkyl.

As noted above, $Q^3$ can be a halogen, an alkyl group, an aryl group, or an amine. In certain embodiments, $Q^3$ is an amine, such as an unsubstituted amine, a monosubstituted amine, or a disubstituted amine.

For example, $Q^3$ can have the formula $-NR^2R^3$, in which $R^2$ is a hydrogen atom or an alkyl group and in which $R^3$ is a hydrogen atom, an alkyl group or an alkylcarbonyl group, for example, as in the case where $R^2$ is a substituted alkyl and $R^3$ is a hydrogen atom, an alkyl group or an alkylcarbonyl group.

Illustratively, $Q^3$ can have the formula $-NR^2R^3$, in which $R^3$ is a hydrogen atom, an alkyl group or an alkylcarbonyl group and in which $R^2$ is a substituted alkyl having the formula $-Z^1-Q^1$, where in $Z^1$ and $Q^1$ are as described above and illustrated below. Thus, in certain embodiments, compounds of Formula I can have the following Formula II:

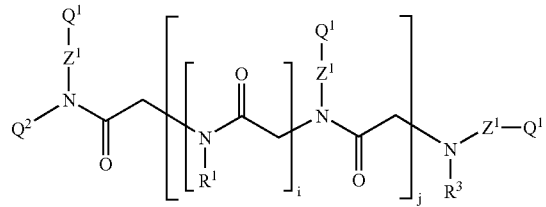

As yet further illustration, in certain embodiments, $Q^3$ can have the formula $-NR^2R^3$, in which $R^2$ is a hydrogen atom or an alkyl group and in which $R^3$ is an alkylcarbonyl group, such as an unsubstituted alkylcarbonyl group or a substituted alkylcarbonyl group (e.g., an ω-aminoalkylcarbonyl group, such as one having the formula $-C(O)-(CH_2)_n-Q^6$, in which n is an integer from 1 to 20 (e.g., from 1 to 12, from 1 to 6, from 1 to 4, etc.) and in which $Q^6$ is an unsubstituted, monosubstituted, or disubstituted amino group). For example, $Q^3$ can have the formula $-NR^2R^3$, in which $R^2$ is a hydrogen atom or an alkyl group and in which $R^3$ is an alkylcarbonyl group substituted with a dye, such as in the case where $Q^3$ can have the formula $-NR^2R^3$, in which $R^2$ is a hydrogen atom or an alkyl group, in which $R^3$ has the formula $-C(O)-R^6-Z^4-Q^7$, and in which $R^6$ represents a bivalent alkyl moiety, $Z^4$ represents a linking moiety (e.g., an amide linkage, an ester linkage, a triazole ring linkage, etc.), and $Q^7$ represents a label, such as a dye (e.g., fluorescein dye or another fluorescent dye), a radioactive label, an enzymatic label, etc. As further examples of dyes that can be used, there can be mentioned Alexa dyes, Bodipy dyes, rhodamine dyes, pyrene dyes, dansyl dyes, and the like.

As yet further illustration, in certain embodiments, $Q^3$ can have the formula $-NR^2R^3$, in which $R^3$ is an alkylcarbonyl group substituted with a dye and in which $R^3$ has the formula $-Z^1-Q^1$.

As another example, $Q^3$ is an amine having the formula:

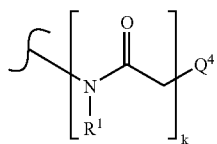

wherein k is an integer from 1 to 100 (e.g., as in the case where k is an integer from 1 to 50, from 1 to 20, from 1 to 10, from 2 to 100, from 2 to 50, from 2 to 20, from 2 to 10 and/or as in the case where k is 1, 2, 3, 4, 5, 6, 7, 8, 9, 10, 11, 12, 13, 14, 15, 16, 17, 18, 19, or 20) and wherein $Q^4$ is a halogen, an alkyl group, an aryl group, or an amine, examples of which include those discussed above with regard to $Q^3$. Thus, in certain embodiments, compounds of Formula I can have the following Formula III:

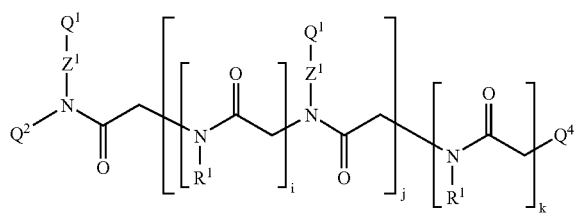

As noted above, $Q^2$ is an alkyl group, such as an unsubstituted alkyl group or a substituted alkyl group. In certain embodiments, $Q^2$ has the formula $-CH_2-C(O)-Q^5$, wherein $Q^5$ is an amine, such as an unsubstituted amine, a monosubstituted amine, or a disubstituted amine. Illustratively, $Q^2$ can have the formula $-CH_2-C(O)-NR^4R^5$, in which $R^4$ is a hydrogen atom or an alkyl group and in which $R^5$ is a hydrogen atom or an alkyl group. In certain embodiments, $Q^2$ has the formula $-CH_2-C(O)-NR^4R^5$, in which $R^4$ is an alkyl group substituted with a dye and in which $R^5$ is a hydrogen atom. In certain embodiments, $Q^2$ has the formula $-CH_2-C(O)-NR^4R^5$, in which $R^4$ is a hydrogen atom and in which $R^5$ is a hydrogen atom, for example, as in the case where a compound of Formula I has the following Formula IV:

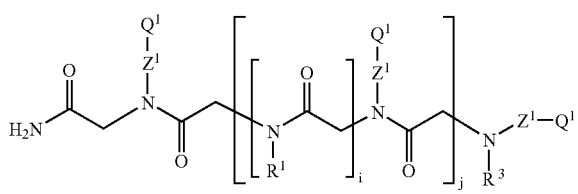

As another example, $Q^2$ can be a substituted alkyl in which $Q^2$ has the following formula:

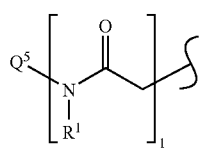

wherein l is an integer from 1 to 100 (e.g., as in the case where l is an integer from 1 to 50, from 1 to 20, from 1 to 10, from 2 to 100, from 2 to 50, from 2 to 20, from 2 to 10 and/or as in the case where l is 1, 2, 3, 4, 5, 6, 7, 8, 9, 10, 11, 12, 13, 14, 15, 16, 17, 18, 19, or 20), and wherein $Q^5$ is an alkyl group, examples of which include those discussed above with regard to $Q^2$. Thus, in certain embodiments, compounds of Formula I can have the following Formula V:

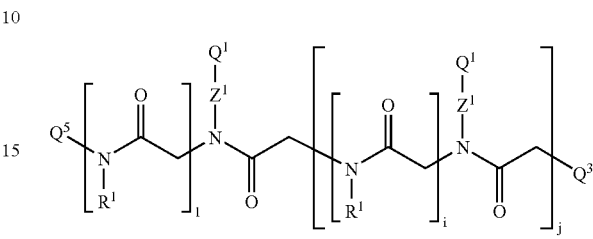

By way of still further illustration, compounds of Formula I can have the following Formula VI:

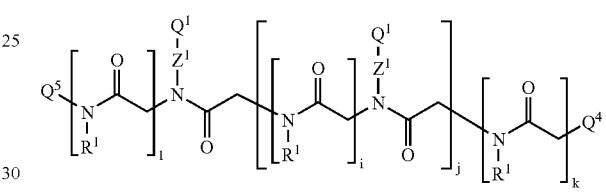

in which $Q^4$, $Q^5$, i, j, k, and l are as set forth above.

In the above Formulae I-VI, each $Z^1$ represents the same or different linking moiety; and each $Q^1$ represents the same or different RNA binding ligand.

For example, when j is 1, there are two $Q^1$'s and two $Z^1$'s in Formula I, the two $Q^1$'s can be the same or they can be different, and the two $Z^1$'s can be the same or they can be different; when j is 2, there are three $Q^1$'s and three $Z^1$'s in Formula I, the three $Q^1$'s can all be the same, they can all be different, or two can be the same and the other one can be different, and the three $Z^1$'s can all be the same, they can all be different, or two can be the same and the other one can be different; etc.

In certain embodiments, each $Q^1$ is the same. In certain embodiments, at least one $Q^1$ is different, as in the case where all but one of the $Q^1$'s are the same, all but two of the $Q^1$'s are the same, all but three of the $Q^1$'s are the same, all but two of the $Q^1$'s are different, all but three of the $Q^1$'s are different, some of the $Q^1$'s are the same and others are different, etc. In certain embodiments, each $Z^1$ is the same. In certain embodiments, at least one $Z^1$ is different, as in the case where all but one of the $Z^1$'s are the same, all but two of the $Z^1$'s are the same, all but three of the $Z^1$'s are the same, all but two of the $Z^1$'s are different, all but three of the $Z^1$'s are different, some of the $Z^1$'s are the same and others are different, etc. The $Z^1$'s and $Q^1$'s can be selected independently of one another. Thus, for example, in certain embodiments, all of the $Q^1$'s are the same, and all of the $Z^1$'s are the same; in certain embodiments, all of the $Q^1$'s are the same, but not all of the $Z^1$'s are the same; in certain embodiments, all of the $Z^1$'s are the same, but not all of the $Q^1$'s are the same; in certain embodiments, not all of the $Q^1$'s are the same, and not all of the $Z^1$'s are the same; etc.

As noted above, each $Z^1$ represents a linking moiety, such as a linking moiety that covalently links its corresponding RNA binding ligand (i.e., its corresponding $Q^1$) with the peptoid polymer backbone. By way of illustration, $Z^1$ can have the formula: $-Z^2-Z^3-Z^4$- wherein $Z^2$ is an alkylene moiety, $Z^4$ is an alkylene moiety, and $Z^3$ is a linkage which serves to covalently connect the $Z^2$ and $Z^4$ alkylene moieties. Examples of suitable $Z^3$'s include amide linkages; ester linkages; ether linkages; and triazole ring linkages, e.g., triazole ring linkages having the formula:

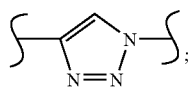

etc. In certain embodiments, $Z^1$ can have the formula $-Z^2-C(O)-NH-Z^4-$, e.g., the formula $-(CH_2)_y-C(O)-NH-(CH_2)_z-$; the formula $-Z^2-NH-C(O)-Z^4-$, e.g., the formula $-(CH_2)_y-NH-C(O)-(CH_2)_z-$; the formula $-Z^2-C(O)-O-Z^4-$, e.g., the formula $-(CH_2)_y-C(O)-O-(CH_2)_z-$; the formula $-Z^2-O-C(O)-Z^4-$, e.g., the formula $-(CH_2)_y-O-C(O)-(CH_2)_z-$; the formula $-Z^2-O-Z^4-$, e.g., the formula $-(CH_2)_y-O-(CH_2)_z-$; the formula:

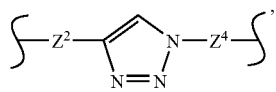

e.g., the formula:

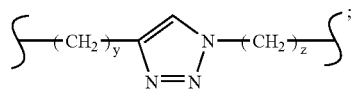

the formula:

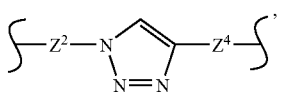

e.g., the formula:

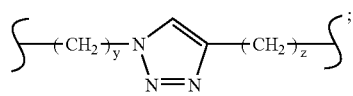

in which y is an integer from 1 to 6 and in which z is an integer from 1 to 6. $Z^1$ can also represent combinations of the above formulae, such as in the case where $Z^1$ has the formula -$Z^2$-$Z^6$-$Z^7$-$Z^8$-$Z^4$-, in which $Z^2$, $Z^4$, and $Z^7$ are alkylene moieties, such as those discussed above; and $Z^6$ and $Z^8$ are independently selected from amide linkages, ester linkages, ether linkages, and triazole ring linkages.

As noted above, each $Q^1$ represents the same or different RNA binding ligand. As used herein, "RNA binding ligand" is meant to refer to non-nucleic acid compounds that may be capable of binding to or otherwise interacting with one or more RNAs or with one or more RNA motifs, such as the RNA motifs discussed above. In this regard, "interacting" is mean to refer to binding or other stabilized association between the ligand and the RNA or RNA motif. The association can be thermodynamically stabilized or kinetically stabilized or both, and the interaction can be the result of covalent bonding, hydrogen bonding, van der Waals interactions, electrostatic interactions, or combinations of these and/or other types of interactions. Examples of RNA binding ligands include proteins, polypeptides, carbohydrates, and other non-nucleic acid biopolymers; peptoids (which is meant to include polypeptoids); whole cells; and small molecules. "Small molecules", as used herein, are meant to refer to non-biopolymer compounds having, for example, a molecular weight of less than 10,000 grams/mole, such as less than 9000 grams/mole, less than 8000 grams/mole, less than 7000 grams/mole, less than 6000 grams/mole, less than 5000 grams/mole, less than 4000 grams/mole, less than 3000 grams/mole, less than 2000 grams/mole, less than 1000 grams/mole, less than 900 grams/mole, less than 800 grams/mole, less than 700 grams/mole, less than 600 grams/mole, less than 500 grams/mole, less than 400 grams/mole, etc.) that may be capable of binding to or otherwise interacting with one or more nucleic acids or nucleic acid motifs. Examples of small molecules that can be used in connection with the present invention include small molecule antibiotics, small molecule antiviral agents, small molecule antifungals, small molecule chemotherapeutics, small molecule heterocyclics, and other small molecule drugs. The small molecules can be biological compounds or mixtures of such compounds (e.g., derived from plant, fungal, bacterial, algal, or other extracts); or they can be synthetic organic compounds; or they can be inorganic compounds (e.g., cisplatin).

Suitable RNA binding ligands (e.g., RNA binding ligands that bind to or otherwise interact with one or more target RNAs or with one or more target RNA motifs) can be identified, for example, using the methods described in Disney et al., "Using Selection to Identify and Chemical Microarray to Study the RNA Internal Loops Recognized by 6-N-Acylated Kanamycin A," *Chem Bio Chem*, 8:649-656 (2007); Childs-Disney et al., "A Small Molecule Microarray Platform to Select RNA Internal Loop-Ligand Interactions," *ACS Chem Biol.*, 2(11):745-754 (2007) (and in the associated Supporting Information (available on the internet at http://pubs.acs.org/subscribe/journals/acbcct/suppinfo/cb700174r/cb700174r-File003.pdf)); U.S. patent application Ser. No. 11/998,466 of Disney et al., filed Nov. 29, 2007; and/or PCT Patent Application No. PCT/US07/024,546 of Disney et al., filed Nov. 29, 2007, each of which is hereby incorporated by reference.

By way of illustration, two or more $Q^1$'s can be selected so as to bind to RNA structural motifs, such as RNA internal loop motifs, RNA hairpin loop motifs, RNA bulge motifs, RNA multibranch loop motifs, and/or an RNA pseudoknot motifs.

For example, some (i.e., one or more) of the $Q^1$'s can be selected so as to bind to a first RNA structural motif and some (i.e., one or more) of the $Q^1$'s can be selected so as to bind to a second RNA structural motif, wherein the first RNA structural motif and the second RNA structural motif are different. Illustratively, some (i.e., one or more) of the $Q^1$'s can be selected so as to bind to an RNA internal loop motif and some (i.e., one or more) of the $Q^1$'s can be selected so as to bind to a second, different RNA internal loop motif; or some (i.e., one or more) of the $Q^1$'s can be selected so as to bind to an RNA internal loop motif and some (i.e., one or more) of the $Q^1$'s can be selected so as to bind to an RNA hairpin loop motif; or some (i.e., one or more) of the $Q^1$'s can be selected so as to bind to an RNA internal loop motif and some (i.e., one or more) of the $Q^1$'s can be selected so as to bind to an RNA bulge motif; etc.

Alternatively, all of the $Q^1$'s can be selected so as to bind to the same RNA structural motif, for example, as where all of the $Q^1$'s are selected so as to bind to multiple copies of the same RNA structural motif. Illustratively, all of the $Q^1$'s are selected so as to bind to multiple copies of the same RNA internal loop motif, or the same RNA hairpin loop motif, or the same RNA bulge motif, etc.

By way of further illustration, two or more $Q^1$'s can be selected so as to bind to RNA repeat motifs, such as RNA triplet repeat motifs (e.g., CUG RNA triplet repeat motifs, CGG RNA triplet repeat motifs, GCC RNA triplet repeat motifs, GAA RNA triplet repeat motifs, CAG RNA triplet repeat motifs, etc.) or RNA tetra repeat motifs (e.g., CCUG RNA tetra repeat motifs).

For example, some (i.e., one or more) of the $Q^1$'s can be selected so as to bind to a first RNA repeat motif and some (i.e., one or more) of the $Q^1$'s can be selected so as to bind to a second RNA repeat motif, wherein the first RNA repeat motif and the second RNA repeat motif are different. Illustratively, some (i.e., one or more) of the $Q^1$'s can be selected so as to bind to a CUG RNA triplet repeat motif and some (i.e., one or more) of the $Q^1$'s can be selected so as to bind to a different RNA triplet repeat motif (e.g., a CAG RNA triplet repeat motif).

Alternatively, all of the $Q^1$'s can be selected so as to bind to the same RNA repeat motif, for example, as where all of the $Q^1$'s are selected so as to bind to a CUG RNA triplet repeat motif, a CGG RNA triplet repeat motif, a GCC RNA triplet repeat motif, a GAA RNA triplet repeat motif, a CAG RNA triplet repeat motif, a CUG RNA triplet repeat motif, or a CCUG RNA tetra repeat motifs).

By way of still further illustration, one or more of the $Q^1$'s can be selected so as to bind to an RNA structural motif, such as any of those described above (e.g., an RNA internal loop motif); and one or more of the $Q^1$'s can be selected so as to bind to an RNA repeat motif, such as any of those described above (e.g., a CUG RNA triplet repeat motif).

Figure 1B:
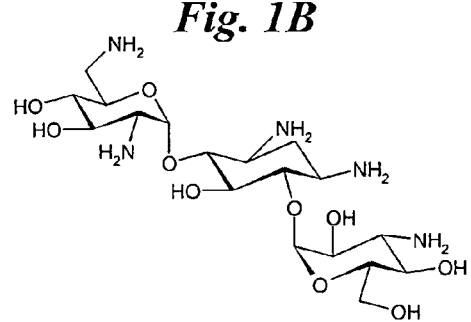
Figure 1C:
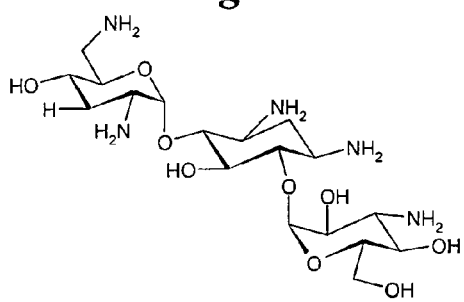
Figure 1D:
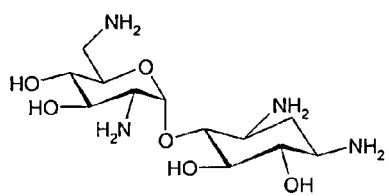
Figure 1E:
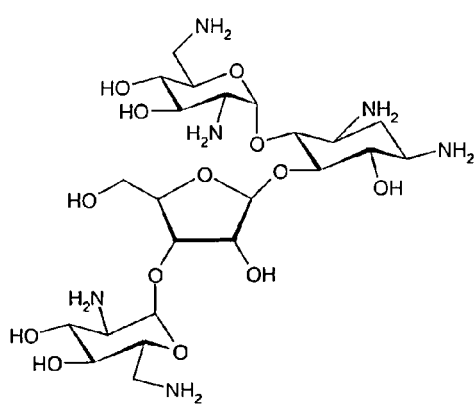
Figure 1F:
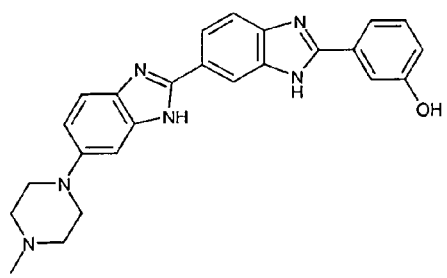
Figure 1G:
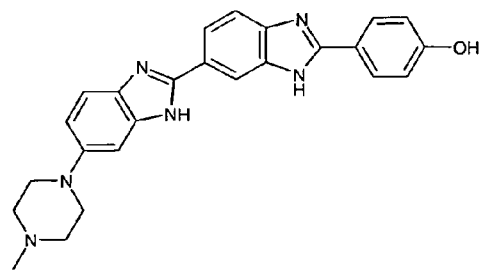

Examples of RNA binding ligands that can be used in the practice of the present invention include aminoglycoside sugars, such as kanamycins (e.g., kanamycin A's (e.g., having the structure shown in FIG. 1A), kanamycin B's (e.g., having the structure shown in FIG. 1B), etc.), tobramycins (e.g., having the structure shown in FIG. 1C), neamines (e.g., having the structure shown in FIG. 1D), neomycins (e.g., having the structure shown in FIG. 1E), and the like; and bis-benzimidazoles, such as pibenzimols (e.g., having the structures shown in FIGS. 1F and 1G, such as Hoechst 33258). Kanamycins, tobramycins, neamines, neomycins, and bis-benzimidazoles can be particularly useful in cases where the target RNA motifs are CUG RNA triplet repeat motifs.

The manner in which the RNA binding ligands are coupled to the $Z^1$'s depends on the nature of the RNA binding ligand(s) being employed and the linkage(s) to be used. Illustratively, coupling can be effected via an RNA binding ligand's carbon atom which bears a hydroxyl group or amine group (e.g., via an RNA binding ligand's hydroxymethyl carbon atom, via an RNA binding ligand's aminomethyl carbon atom, via an RNA binding ligand's hydroxy-substituted ring carbon atom, via an RNA binding ligand's amine-substituted ring carbon atom, and the like). In cases where the RNA binding ligand is an aminoglycoside sugar, coupling can be effected, for example, via the aminoglycoside sugar's 6' position (e.g., via the 6' position of kanamycin A, kanamycin B, tobramycin, neamine, and neomycin); via the aminoglycoside sugar's 6" position (e.g., via the 6" position of kanamycin A, kanamycin B, and tobramycin); via the aminoglycoside sugar's 5 position (e.g., via the 5 position of neamine); in those cases where the aminoglycoside sugar includes a tetrahydrofuran ring, via the tetrahydrofuran ring's hydroxymethyl carbon atom (e.g., via the tetrahydrofuran ring's hydroxymethyl carbon atom in neomycin); etc.

In certain embodiments, each Q.sup.1 is the same or different and is selected from aminoglycoside sugars and bis-benzimidazoles, such as in the case where each Q.sup.1 is the same or different and is an aminoglycoside sugar. In certain embodiments, each Q.sup.1 is a kanamycin A. In certain embodiments, each Q.sup.1 is a neamine. In certain embodiments, each Q.sup.1 is a bis-benzimidazole. In certain embodiments, some (i.e., one or more) of the Q.sup.1's are kanamycin A's and some of the Q.sup.1's are bis-benzimidazoles. In certain embodiments, some (i.e., one or more) of the Q.sup.1's are kanamycin A's and some of the Q.sup.1's are neamines. In certain embodiments, some (i.e., one or more) of the Q.sup.1's are neamines and some of the Q.sup.1's are bis-benzimidazoles.

For example, a $Q^1$ (or more than one $Q^1$) can be selected so as to bind to one or more RNA internal loop motifs that comprise a pyridimine across from a pyridimine (e.g., a uracil opposing a uracil, a cytosine across from a cytosine, a uracil across from a cytosine, etc.). Examples of such RNA internal loop motifs include 1×1, 2×2, 3×3, etc. internal loops, such as 5'C/3'C; 5'U/3'U; 5'AU/3'AU; 5'UA/3'UA; 5'UAU/3'UUU; 5'GUC/3'GCU; 5'GCU/3'GUC; 5'CUC/3'CGU; 5'CGU/3'CUC; 5'UGA/3'UGG; 5'UGG/3'UGA; etc. Such RNA internal loop motifs can be targeted with an aminoglycoside sugar, such as a kanamycin A (e.g., a kanamycin A coupled via its 6", position).

As a further example, a $Q^1$ (or more than one $Q^1$) can be selected so as to bind to one or more RNA internal loop motifs that comprise a guanine across from a guanine. Examples of such RNA internal loop motifs include 1×1, 2×2, 3×3, etc. internal loops, such as 5'G/3'G; 5'CG/3'CG; 5'GA/3'GC; 5'GC/3'GA; 5'AG/3'GG; 5'GG/3'AG; 5'AG/3'CG; 5'CG/3'AG; 5'AGA/3'CGA; 5'CGA/3'AGA; etc. Such RNA internal loop motifs can be targeted with an aminoglycoside sugar, such as a tobramycin (e.g., a tobramycin coupled via its 6" position).

As a further example, a $Q^1$ (or more than one $Q^1$) can be selected so as to bind to one or more RNA internal loop motifs that comprise an adenine across from a guanine. Examples of such RNA internal loop motifs include 1×1, 2×2, 3×3, etc. internal loops, such as 5'A/3'G; 5'G/3'A; 5'CA/3'CG; 5'CG/3'CA; 5'AG/3'GG; 5'GG/3'AG; 5'UA/3'UG; 5'UG/3'UA; 5'GA/3'AA; 5'AA/3'GA; 5'GGA/3'AUG; 5'AUG/3'GGA; 5'AAC/3'GGU; 5'GGU/3'AAC; 5'AGA/3'CUG; 5'CUG/3'AGA; 5'AAG/3'CUA; 5'CUA/3'AAG; 5'AAC/3'GCU; 5'GCU/3'AAC; 5'AAC/3'GUA; 5'GUA/3'AAC; etc., and such RNA internal loop motifs can be targeted with an aminoglycoside sugar, such as a neamine (e.g., a neamine coupled via its 5 position). Other examples of such RNA internal loop motifs also include 1×1, 2×2, 3×3, etc. internal loops, such as 5'A/3'G; 5'G/3'A; 5'AA/3'GC; 5'GC/3'AA; 5'AA/3'CG; 5'CG/3'AA; 5'AA/3'GA; 5'AA/3'GA; 5'AU/3'GC; 5'GC/3'AU; 5'AA/3'GG; 5'GG/3'AA; 5'CAA/3'AUG; 5'AUG/3'CAA; 5'CAC/3'CGC; 5'CGC/3'CAC; 5'CUA/3'CCG; 5'CCG/3'CUA; 5'AGU/3'GGC; 5'GGC/3'AGU; 5'AAC/3'GGA; 5'GGA/3'AAC; 5'GUA/3'GAG; 5'GAG/3'GUA; 5'AGA/3'ACG; 5'ACG/3'AGA; 5'AGC/3'GCC; 5'GCC/3'AGC; etc., and such RNA internal loop motifs can be targeted with an aminoglycoside sugar, such as a neomycin (e.g., a neomycin coupled via the hydroxymethyl carbon atom of the neomycin's tetrahydrofuran ring).

The above-described RNA targeting compounds of Formula I in which j is 1 can have the following Formula VII:

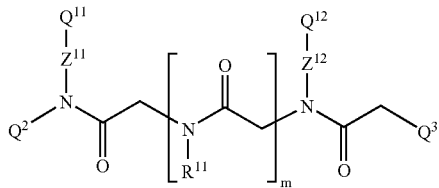

wherein m is zero or an integer from 1 to 100 (e.g., zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, or 20); $Z^{11}$ and $Z^{12}$ represent the same or different linking moieties (examples of which include those described above with regard to $Z^1$); $R^{11}$ is an alkyl or aryl group (examples of which include those described above with regard to $R^1$); and $Q^{11}$ and $Q^{12}$ represent the same or different RNA binding ligands (examples of which include those described above with regard to $Q^1$).

The above-described RNA targeting compounds of Formula I in which j is 2 can have the following Formula VIII:

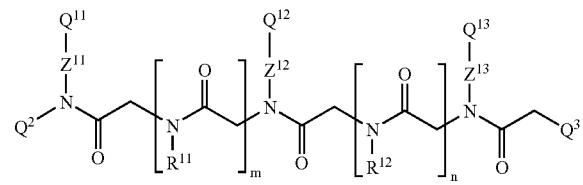

wherein m is zero or an integer from 1 to 100; n is zero or an integer from 1 to 100; $Z^{11}$, $Z^{12}$, and $Z^{13}$ represent the same or different linking moieties (examples of which include those described above with regard to $Z^1$); $R^{11}$ and $R^{12}$ represent the same or different alkyl or aryl groups (examples of which include those described above with regard to $R^1$); and $Q^{11}$, $Q^{12}$, and $Q^{13}$ represent the same or different RNA binding ligands (examples of which include those described above with regard to $Q^1$). Illustratively, m and n can be the same, or they can be different; and examples of suitable m and n include zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, and 20).

The above-described RNA targeting compounds of Formula I in which j is 3 can have the following Formula IX:

wherein m is zero or an integer from 1 to 100; n is zero or an integer from 1 to 100; p is zero or an integer from 1 to 100; $Z^{11}$, $Z^{12}$, $Z^{13}$, and $Z^{14}$ represent the same or different linking moieties (examples of which include those described above with regard to $Z^1$); $R^{11}$, $R^{12}$, and $R^{13}$, represent the same or different alkyl or aryl groups (examples of which include those described above with regard to $R^1$); and $Q^{11}$, $Q^{12}$, $Q^{13}$, and $Q^{14}$ represent the same or different RNA binding ligands (examples of which include those described above with regard to $Q^1$). Illustratively, m, n, and p can be the same, or they can be different; and examples of suitable m, n, and p include zero or an integer from 1 to 50, zero or an integer from 1 to 20, zero or an integer from 1 to 10, an integer from 2 to 100, an integer from 2 to 50, an integer from 2 to 20, an integer from 2 to 10, 0, 1, 2, 3, 4, 5, 6, 7, 8, 9, 10, 11, 12, 13, 14, 15, 16, 17, 18, 19, and 20).

In each of Formulae VII, VIII, and IX, $Q^2$ and $Q^3$ have the meanings described above with regard to Formula I. It will be appreciated that Formulae VII, VIII, and IX are intended to be illustrative of RNA targeting compounds of Formula I (specifically RNA targeting compounds of Formula I in which j is 1, 2, and 3, respectively). RNA targeting compounds of Formula I in which j is greater than 3 (e.g., 4, 5, 6, 7, 8, 9, 10, etc.) having structures that are analogous to Formulae VII, VIII, and IX can be readily envisioned are intended to be encompassed by Formula I.

The RNA targeting compounds of Formula I can be prepared by any suitable method, such as those described below and in the Examples which follow.

Illustratively, the compounds of the present invention can be prepared using a peptoid synthesis scheme in which the peptoid backbone is built in a step-wise manner by sequential reactions with (1) bromoacetic acid and (2) functionalized alkyl amines (i.e., alkyl amines in which the alkyl group bears a substituent to which an RNA binding ligand can be coupled) or non-functionalized alkyl amines (e.g., alkyl amines in which the alkyl group is unsubstituted or substituted with a group that is not involved in coupling the RNA binding ligand). The peptoid backbone can be built on a suitable substrate (e.g., a resin), and the resulting peptoid can be cleaved from the substrate after the reaction is complete. The step-wise process permits the introduction of functionalized alkyl groups at particular positions on the peptoid backbone and, consequently, permits one to control the spacing between RNA binding ligands (once the RNA binding ligands are coupled to the functionalized alkyl groups).

Figure 2:
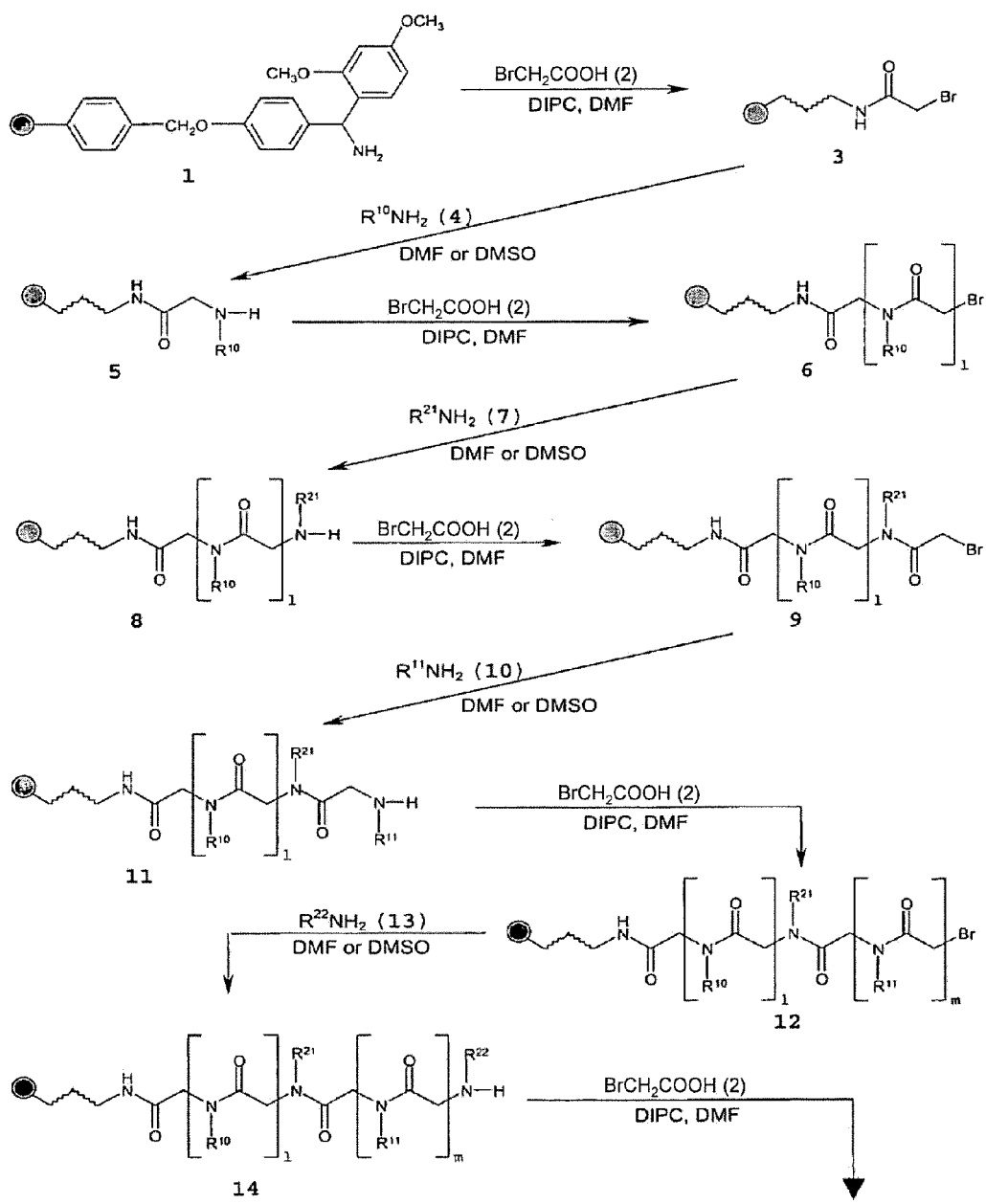
FIGS. 2 and 3A are reaction schemes for making peptoid backbones that can be used in the preparation of various compounds of the present invention.
Figure 2:
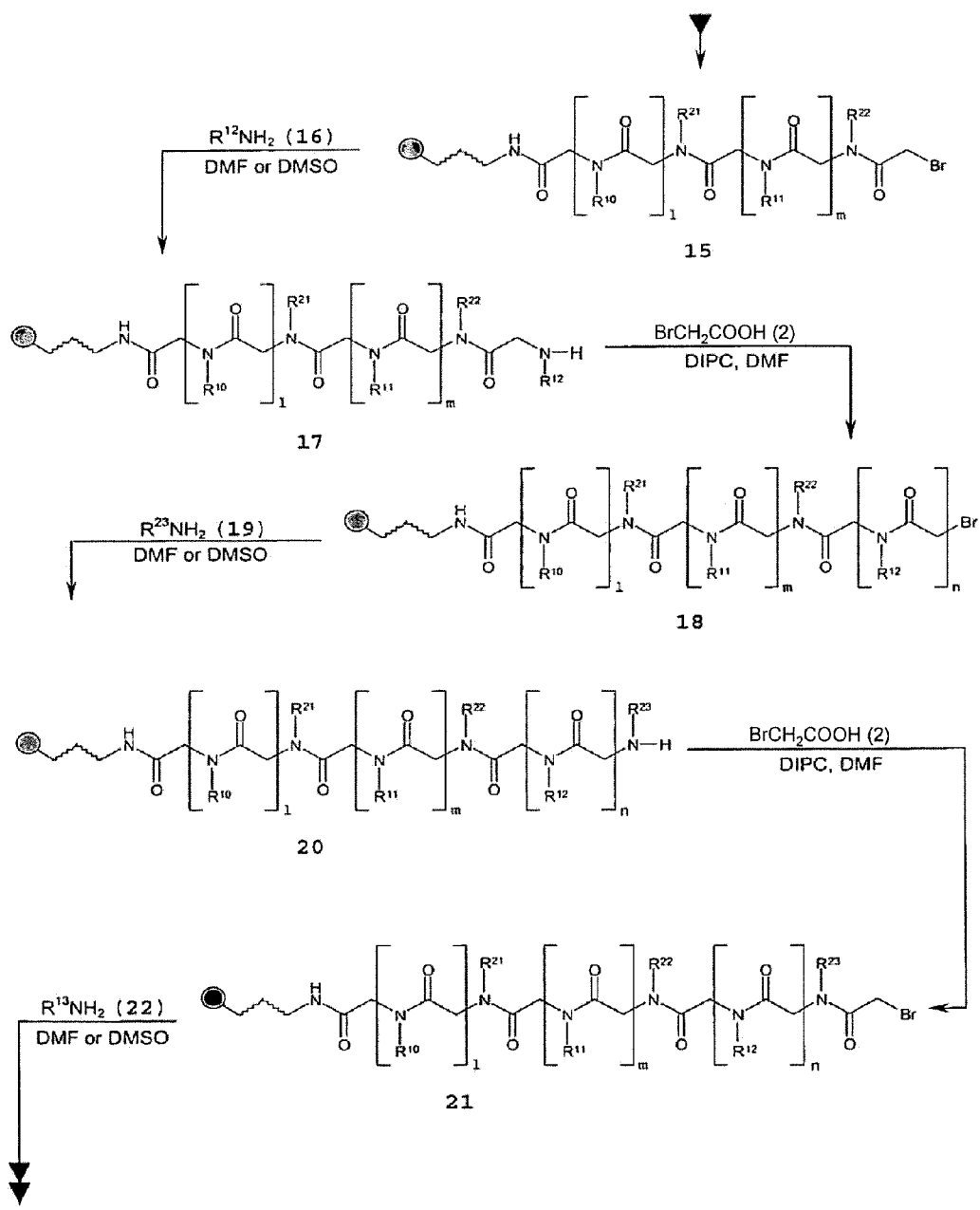
Figure 2:
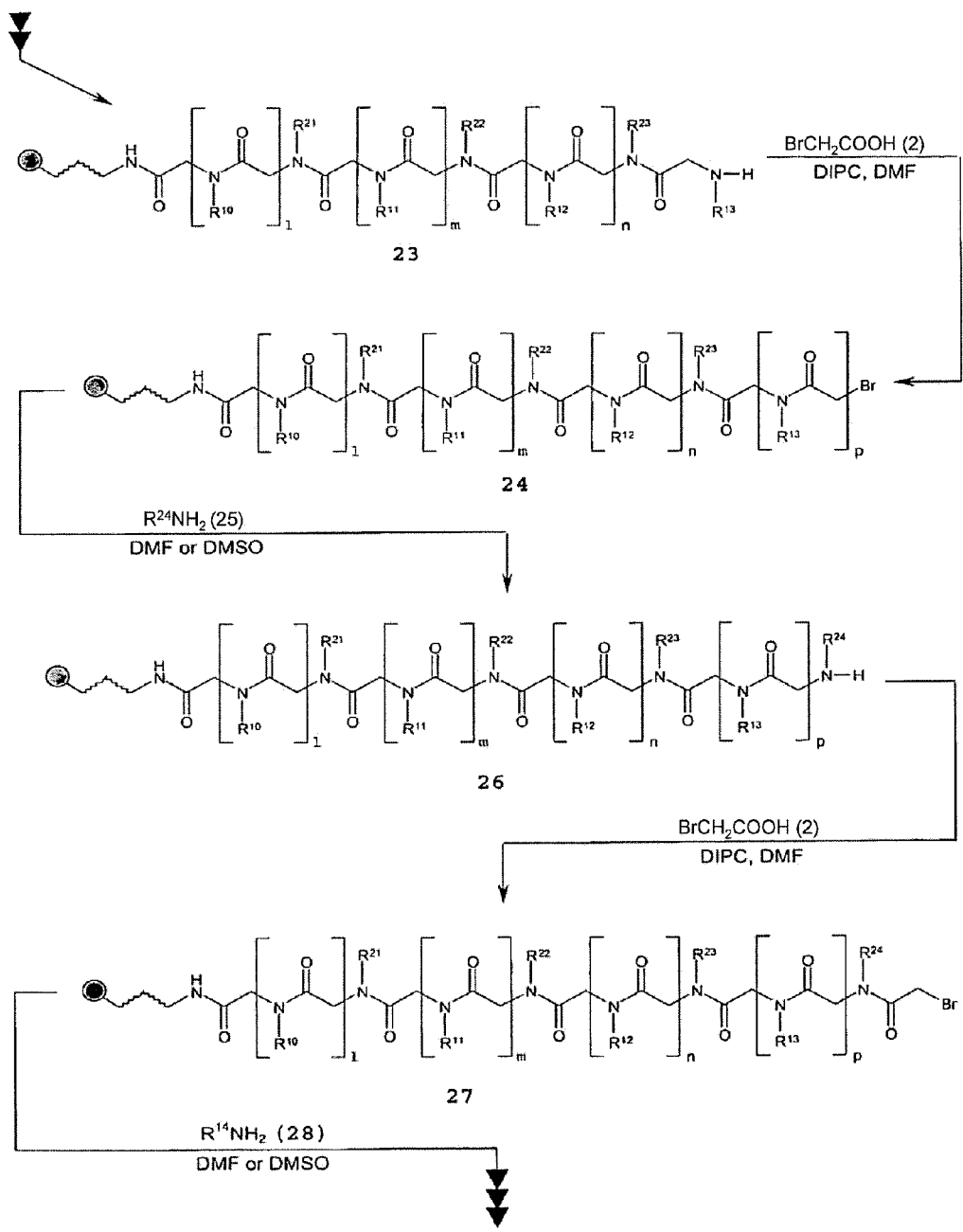
Figure 2:
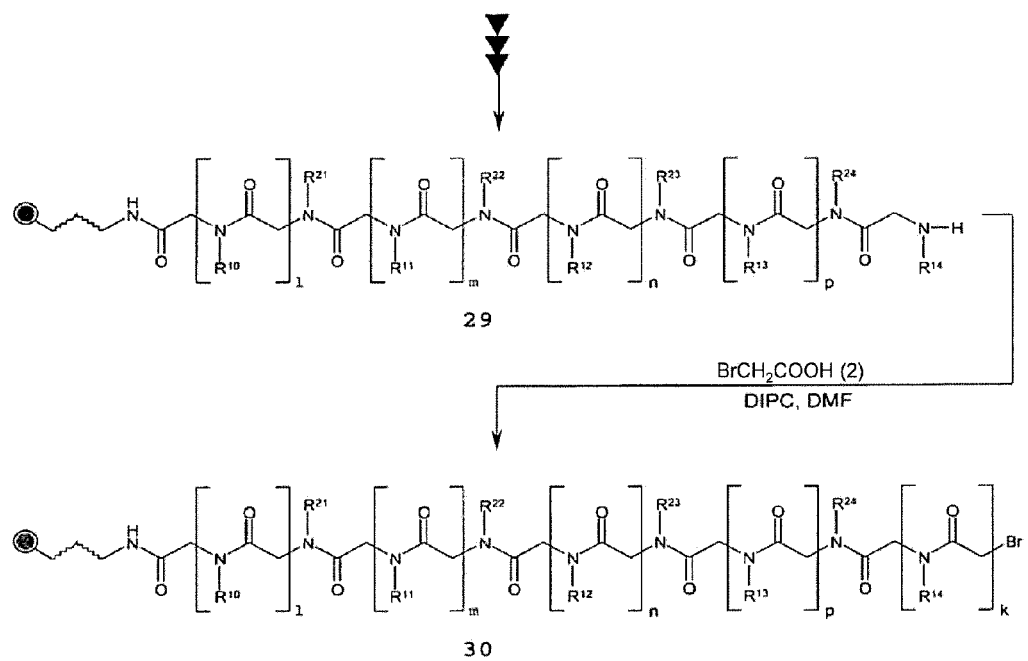

A step-wise synthetic scheme for the preparation of a compound of Formula I is presented in FIG. 2. More particularly, the scheme shown in FIG. 2 is designed to produce compounds of Formula I having the following Formula X:

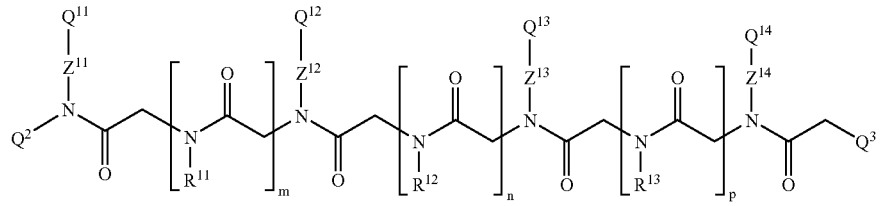

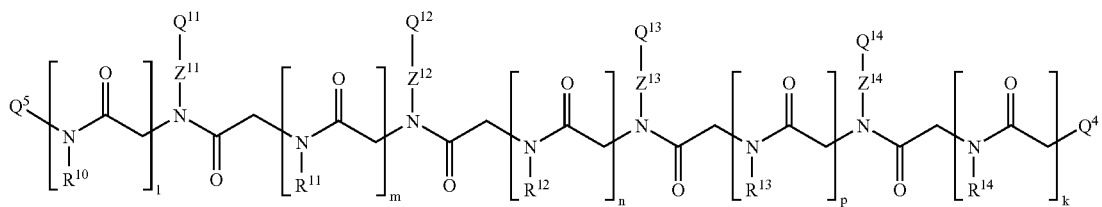

in which k, l, m, n, p, $R^{11}$, $R^{12}$, $R^{13}$, $Z^{11}$, $Z^{12}$, $Z^{13}$, $Z^{14}$, $Q^{11}$, $Q^{12}$, $Q^{13}$, $Q^{14}$, $Q^4$, and $Q^5$ are as described above and in which each $R^{10}$ and each $R^{14}$ are independently selected alkyl or aryl groups.

Briefly, a resin bearing primary amine groups (such as deprotected Fmoc-Rink amide resin 1) is reacted with bromoacetic acid 2 in a suitable solvent (e.g., dimethylformamide ("DMF")) and in the presence of a dehydration agent, such as a dialkylcarbodiimide (e.g., diisopropylcarbodiimide ("DIPC")), for a suitable period of time (e.g., for from about 5 minutes to about 1 hour, such as for about 20 minutes) and at a suitable temperature (e.g., at from about room temperature to about 50° C., such as at about 37° C.) to produce bromoacetamide 3. After washing with a suitable solvent (e.g., dichloromethane ("DCM") or another suitable chlorinated hydrocarbon, DMF, or combinations thereof), bromoacetamide 3 is optionally (in those cases where l is not zero) reacted with non-functionalized amine 4 in a suitable solvent (e.g., DMF or tetrahydrofuran ("THF")) for a suitable period of time (e.g., for from about 5 minutes to about 1 hour, such as for about 20 minutes) and at a suitable temperature (e.g., at from about room temperature to about 50° C., such as at about 37° C.) to produce aminoacetamide 5; and, after washing with, for example, DCM and DMF, aminoacetamide 5 is then reacted with bromoacetic acid 2, as described above, to produce bromoacetamide 6 (l=1). In those cases where l>1, the process (reaction with non-functionalized amine 4 followed by reaction with bromoacetic acid 2) is repeated l–1 additional times. In each repetition, $R^{10}$ in non-functionalized amine 4 can be varied if desired.

Bromoacetamide 6 (l≠0) (or, in those cases where l is zero, bromoacetamide 3) is then reacted with functionalized amine 7 in a suitable solvent (e.g., DMF or THF) for a suitable period of time (e.g., for from about 5 minutes to about 1 hour, such as for about 20 minutes) and at a suitable temperature (e.g., at from about room temperature to about 50° C., such as at about 37° C.) to produce aminoacetamide 8. After washing with, for example, DCM and DMF, aminoacetamide 8 is then reacted with bromoacetic acid 2, as described above, to produce bromoacetamide 9.

Bromoacetamide 9 is optionally (in those cases where m is not zero) reacted with non-functionalized amine 10, as described above, to produce aminoacetamide 11; and, after washing with, for example, DCM and DMF, aminoacetamide 11 is then reacted with bromoacetic acid 2, as described above, to produce bromoacetamide 12 (m=1). In those cases where m>1, the process (reaction with non-functionalized amine 10 followed by reaction with bromoacetic acid 2) is repeated m–1 additional times. In each repetition, $R^{11}$ in non-functionalized amine 10 can be varied if desired.

Bromoacetamide 12 (m≠0) (or, in those cases where m is zero, bromoacetamide 9) is then reacted with functionalized amine 13 in a suitable solvent (e.g., DMF or THF), as described above, to produce aminoacetamide 14. After washing with, for example, DCM and DMF, aminoacetamide 14 is then reacted with bromoacetic acid 2, as described above, to produce bromoacetamide 15.

Bromoacetamide 15 is optionally (in those cases where n is not zero) reacted with non-functionalized amine 16, as described above, to produce aminoacetamide 17; and, after washing with, for example, DCM and DMF, aminoacetamide 17 is then reacted with bromoacetic acid 2, as described above, to produce bromoacetamide 18 (n=1). In those cases where m>1, the process (reaction with non-functionalized amine 16 followed by reaction with bromoacetic acid 2) is repeated n–1 additional times. In each repetition, $R^{12}$ in non-functionalized amine 16 can be varied if desired.

Bromoacetamide 18 (or, in those cases where n is zero, bromoacetamide 15) is then reacted with functionalized amine 19, as described above, to produce aminoacetamide 20. After washing with, for example, DCM and DMF, aminoacetamide 20 is then reacted with bromoacetic acid 2, as described above, to produce bromoacetamide 21.

Bromoacetamide 21 is optionally (in those cases where p is not zero) reacted with non-functionalized amine 22, as described above, to produce aminoacetamide 23; and, after washing with, for example, DCM and DMF, aminoacetamide 23 is then reacted with bromoacetic acid 2, as described above, to produce bromoacetamide 24 (p=1). In those cases where p>1, the process (reaction with non-functionalized amine 22 followed by reaction with bromoacetic acid 2) is repeated n–1 additional times. In each repetition, $R^{13}$ in non-functionalized amine 22 can be varied if desired.

Bromoacetamide 24 (or, in those cases where p is zero, bromoacetamide 21) is then reacted with functionalized amine 25, as described above, to produce aminoacetamide 26. Aminoacetamide 26 can then reacted with bromoacetic acid 2, as described above, to produce bromoacetamide 27.

In those cases where k is not 0, bromoacetamide 27 can then be reacted with non-functionalized amine 28, as described above, to produce aminoacetamide 29. In those cases where k>1, the process (reaction with non-functionalized amine 28 followed by reaction with bromoacetic acid 2) can be repeated k–1 more times. In each repetition, $R^{14}$ in non-functionalized amine 28 can be varied if desired. The resulting aminoacetamide 29 (k≠0) can then reacted with bromoacetic acid 2, as described above, to produce bromoacetamide 30 ($Q^4$=Br in Formula X).

As one skilled in the art will appreciate, the process described above can be repeated any number of times to extend the peptoid backbone and introduce additional functionalized alkyl groups.

The terminal bromine (e.g., the bromine on the right size of bromoacetamide 27 (in cases where k is zero) or the bromine on the right size of bromoacetamide 30 (in cases where k>0) provides a convenient place to perform additional chemistry. Illustratively, bromoacetamide 27 or bromoacetamide 30 can be alkylated or arylated to provide compounds in which $Q^4$ is an alkyl or aryl group. Alternatively, bromoacetamide 27 or bromoacetamide 30 can be reacted with a functionalized amine (e.g., $HNR^{25}$ in which $R^{21}$ is a functionalized alkyl), for example, to produce a compound in which $Q^4$ has the formula —$NHR^{25}$ (e.g., as a way of producing a compound of Formula X in which $Q^4$ has the formula —$NHZ^{15}Q^{15}$ in which $Q^{15}$ is an RNA binding ligand (examples of which include those described above with regard to $Q^1$) and in which $Z^{15}$ is a linking moiety (examples of which include those described above with regard to $Z^1$)). Still alternatively, bromoacetamide 27 or bromoacetamide 30 can be reacted with a non-functionalized amine, for example, to produce a compound in which $Q^4$ has the formula —$NHR^{15}$ in which $R^{15}$ is an alkyl group or an aryl group (e.g., an unsubstituted alkyl group). In those cases where bromoacetamide 27 or bromoacetamide 30 are reacted with a functionalized or non-functionalized amine, the amine's nitrogen can provide a convenient site for further chemistry. For example, reaction of the terminal amine with an acid, such as a Fmoc-protected aminoalkanoic acid (e.g., a Fmoc-protected 6-aminohexanoic acid) provides a functionalized spacer, to which a dye (e.g., a fluorescent dye) or other labeling moiety can be coupled.

In FIG. 2 and in the above discussion, $R^{21}$, $R^{22}$, $R^{23}$, $R^{24}$, and $R^{25}$ represent functionalized alkyl groups (i.e., alkyl groups which bear a substituent to which an RNA binding ligand can be coupled via, for example, an amide linkage, an ester linkage, an ether linkage, or a triazole ring linkage. Suitable functional groups include, for example, carboxylic acids and protected carboxylic acids, amines and protected amines, hydroxyls and protected hydroxyls, alkynes, and azides. To produce compounds of Formula X, the functional groups on $R^2$, $R^{22}$, $R^{23}$, $R^{24}$, and $R^{25}$ are coupled to the desired RNA binding ligands to produce the -$Z^{11}$-$Q^{11}$, -$Z^{12}$-$Q^{12}$, $Z^{13}$-$Q^{13}$, $Z^{14}$-$Q^{14}$, and -$Z^{15}$-$Q^{15}$ moieties, respectively.

This can be done while the peptoid backbone is being constructed, for example, as in the case where $R^{21}$ of aminoacetamide 8 is coupled to the desired RNA binding ligand (to produce the -$Z^{11}$-$Q^{11}$ moiety) prior to reacting aminoacetamide 8 with bromoacetic acid 2 to produce bromoacetamide 9; and as in the case where $R^{21}$ of aminoacetamide 8 is coupled to the desired RNA binding ligand (to produce the -$Z^{11}$-$Q^{11}$ moiety) after reacting aminoacetamide 8 with bromoacetic acid 2 to produce bromoacetamide 9 but prior to optionally reacting bromoacetamide 9 with non-functionalized amine 10 to produce aminoacetamide 11 and/or prior to reacting bromoacetamide 12 with functionalized amine 13 to produce aminoacetamide 14. This step-wise coupling is particularly useful in those cases where different RNA binding ligands are to be coupled at different locations along the peptoid backbone.

In cases where some of the RNA binding ligands are the same and adjacent to one another (e.g., as in the case where $Q^{11}$ and $Q^{12}$ are the same but different from $Q^{13}$), $R^{21}$ and $R^{22}$ of aminoacetamide 14 can be coupled to the desired RNA binding ligand (to produce the -$Z^{11}$-$Q^{11}$ and -$Z^{12}$-$Q^{12}$ moieties) in a single step prior to reacting bromoacetamide 18 with functionalized amine 19 to produce aminoacetamide 20.

In cases where all of the RNA binding ligands are the same, $R^{21}$, $R^{22}$, $R^{23}$, and $R^{24}$ of aminoacetamide 29 or bromoacetamide 30 or subsequent reaction products thereof (and any other functionalized alkyl groups that might be present, such as $R^{25}$) can be coupled to the desired RNA binding ligand in a single step. This single-step coupling can take place before or after the peptoids are cleaved from the resin or other substrate (described below).

After the peptoid backbone is prepared and after the RNA binding ligands are coupled (if such coupling is to be performed prior to cleavage from the resin or other substrate) and/or after any other desired chemistry is performed (e.g., any reactions involving the terminal bromine and/or terminal amine) (if such chemistry is to be performed prior to cleavage from the resin or other substrate), the peptoids are cleaved from the resin or other substrate. Methods for cleaving the peptoids from the substrate will depend on the nature of the substrate. Where a Fmoc-Rink amide resin is employed (as in FIG. 2 and the discussion above), cleavage can be effected using 95:5 trifluoroacetic acid:water.

The present invention, in another aspect thereof, relates to an RNA targeting compound that includes a polymer backbone and two or more pendant RNA binding ligands, wherein the two or more pendant RNA binding ligands are bound to the polymer backbone.

Illustratively, the RNA targeting compound can include 2 pendant RNA binding ligands, 3 or more pendant RNA binding ligands, 4 or more pendant RNA binding ligands, 5 or more pendant RNA binding ligands, from 2 to 100 pendant RNA binding ligands, from 2 to 50 pendant RNA binding ligands, from 2 to 20 pendant RNA binding ligands, and/or 2, 3, 4, 5, 6, 7, 8, 9, 10, 15, or 20 pendant RNA binding ligands.

The two or more pendant RNA binding ligands can bind to RNA structural motifs, such as in the case where each of the RNA structural motifs is independently selected from an RNA internal loop motif, an RNA hairpin loop motif, an RNA bulge motif, an RNA multibranch loop motif, and/or an RNA pseudoknot motif. Additionally, or alternatively, the two or more pendant RNA binding ligands can bind to RNA repeat motifs, such as RNA triplet repeat motifs (e.g., CUG RNA triplet repeat motifs, CUG RNA triplet repeat motifs, CGG RNA triplet repeat motifs, GCC RNA triplet repeat motifs, GAA RNA triplet repeat motifs, and/or CAG RNA triplet repeat motifs) or RNA tetra repeat motifs (e.g., CCUG RNA tetra repeat motifs).

In certain embodiments, each of the two or more pendant RNA binding ligands are the same. In certain embodiments, the two or more pendant RNA binding ligands are not the same (e.g., at least one is different from the others, at least two are different from the others; etc.).

Examples of suitable pendant RNA binding ligands include those described above (e.g., with regard to Q.sup.1). Illustratively, the two or more pendant RNA binding ligands can be the same or different and are selected from aminoglycoside sugars and bis-benzimidazoles. In certain embodiments, the two or more pendant RNA binding ligands are aminoglycoside sugars, such as kanamycins (e.g., kanamycin A's, kanamycin B's), tobramycins, neamines, neomycins, and the like. In certain embodiments, the two or more pendant RNA binding ligands are kanamycin A's. In certain embodiments, the two or more pendant RNA binding ligands are neamines. In certain embodiments, the two or more pendant RNA binding ligands are tobramycins. In certain embodiments, the two or more pendant RNA binding ligands are neomycins. In certain embodiments, the two or more pendant RNA binding ligands are bis-benzimidazoles, such as in the case where the two or more pendant RNA binding ligands are pibenzimols, examples of which include Hoechst 33258.

As used herein in this context, "polymer backbone" is meant to refer to a repeating, substantially linear collection of 3 or more (e.g., 4 or more, 5 or more, etc.) atoms that are covalently bonded to one another. The polymer backbone can be, for example, a peptoid polymer backbone (e.g., as in the case where the polymer backbone has a repeating —C(O)—N-alkylene-structure (e.g., a repeating —C(O)—N—$CH_2$— structure, such as where the polymer backbone can be represented by the formula: $\{C(O)-N-CH_2\}_z$ where z is an integer greater than or equal to 2, such as from 2 to 1000, from 3 to 1000, from 4 to 1000, from 5 to 1000, from 2 to 200, from 3 to 200, from 4 to 200, from 5 to 200, from 2 to 100, from 3 to 100, from 4 to 100, from 5 to 100, and/or 2, 3, 4, 5, 6, 7, 8, 9, 10, 20, 30, 40, 50, and the like. Other suitable polymer backbones include those based on biological monomers, such as peptides (e.g., alpha amino acids, beta amino acids, etc.) as well as those based on non-biological monomers (e.g., polyethers; polyurethanes; polyamides; polyacrylates; polyethylenes, polypropylenes, and other polyolefins; polyethylene glycols; and the like).

As noted above, the two or more pendant RNA binding ligands are bound (e.g., covalently) to the polymer backbone, for example, via a linking moiety, examples of which include those discussed above in the context of Formula I. Illustratively, in the case where the polymer backbone is a peptoid polymer backbone, the two or more pendant RNA binding ligands can be bound (e.g., via an optional linker) to some or all of the peptoid polymer backbone's nitrogen atom. Those nitrogen atoms in the peptoid polymer backbone that are not bound to pendant RNA binding ligands can be substituted with the same or different substituents, such as alkyl or aryl groups (some or all of which alkyl or aryl groups can be substituted or not).

Methods for making the subject RNA targeting compounds that utilize a peptoid polymer backbone include those described hereinabove in relation to the preparation of RNA targeting compounds of Formula I. In those cases where non-peptoid polymer backbones are employed, one skilled in the art can readily identify suitable methods of preparation, taking into account the functional groups that may be present on the polymer backbone to be used, the functional groups that may be present on the RNA binding ligands to be used, the preparative methods described above with regard to the synthesis of compounds of Formula I, and conventional synthetic methodologies.

The compounds of the present invention can be used in a variety of ways.

Illustratively, the compounds can be used, for example in a competitive binding assay, to determine the ability of other compounds to bind to particular RNA or particular RNA motifs.

By way of further illustration, compounds of the present invention that include a dye (e.g., a fluorescent dye), a label, a marker, or other probe can be used to detect the presence of a particular RNA or particular RNA motifs in a sample. Such assays can be carried out in vivo, ex vivo, or in vitro. Illustratively, compounds of the present invention that include a dye (e.g., a fluorescent dye) or other probe can be used to detect the presence, quantify the amount, and/or determine the location of the particular RNA or particular RNA motifs that may be present in a sample, such as a biological sample, a tissue sample, a blood sample, a urine sample, a cell sample, or in an organism.

By way of still further illustration, compounds of the present invention can be used to treat RNA-mediated diseases or conditions, such as diseases or conditions that are caused by triplet repeats, for example, triplet repeats in non-coding regions (examples of which include myotonic dystrophy (CUG repeat), spinocerebellar ataxia type 8 (CUG repeat), Fragile X syndrome (CGG repeat), Fragile XE syndrome (GCC repeat), Friedreich's ataxia (GAA repeat), and spinocerebellar ataxia type 12 (CAG repeat)) and triplet repeats in coding regions (examples of which include spinocerebellar ataxia type 1 (CAG repeat), spinocerebellar ataxia type 2 (CAG repeat), spinocerebellar ataxia type 3 (CAG repeat), spinobulbar muscular atrophy (Kennedy's Disease) (CAG repeat), Huntington's Disease (CAG repeat), dentatorubral-pallidoluysian atrophy (CAG repeat), spinocerebellar ataxia type 6 (CAG repeat), and spinocerebellar ataxia type 7 (CAG repeat)); or that are caused by RNA tetra repeats, such as myotonic dystrophy type 2 (CCUG repeats).

For example, the present invention relates to a method for treating a disease caused by RNA triplet or tetra repeats in a subject, and the method includes administering, to the subject, an RNA targeting compound of the present invention in which at least some of the RNA binding ligands (e.g., each of the RNA binding ligands) bind to a RNA triplet or tetra repeat motif. In certain embodiments, the disease is myotonic dystrophy, and some or all of the RNA binding ligands bind to a CUG RNA triplet repeat motif. In certain embodiments, the disease is myotonic dystrophy, and the RNA binding ligands are the same or different and are selected from aminoglycoside sugars and bis-benzimidazoles. In certain embodiments, the disease is spinocerebellar ataxia type 8, and some or all of the RNA binding ligands bind to a CUG RNA triplet repeat motif. In certain embodiments, the disease is spinocerebellar ataxia type 8, and the RNA binding ligands are the same or different and are selected from aminoglycoside sugars and bis-benzimidazoles. In certain embodiments, the disease is Fragile X syndrome, and some or all of the RNA binding ligands bind to a CGG RNA triplet repeat motif. In certain embodiments, the disease is Fragile XE syndrome, and some or all of the RNA binding ligands bind to a GCC RNA triplet repeat motif. In certain embodiments, the disease is Friedreich's ataxia, and some or all of the RNA binding ligands bind to a GAA RNA triplet repeat motif. In certain embodiments, the disease is selected from spinocerebellar ataxia type 1, type 2, type 3, type 6, type 7, or type 12, spinobulbar muscular atrophy, Huntington's Disease, and dentatorubral-pallidoluysian atrophy; and some or all of the RNA binding ligands bind to a CAG RNA triplet repeat motif. In certain embodiments, the disease is myotonic dystrophy type 2, and some or all of the RNA binding ligands bind to a CCUG RNA tetra repeat motif.

The aforementioned RNA targeting compound of the present invention can be administered to the subject by any conventional route. The compositions herein may be made up in any suitable form appropriate for the desired use. Examples of suitable dosage forms include oral, parenteral, or topical dosage forms.

Illustratively, suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In addition to the above, generally non-active components of the above-described formulations, these formulations can include other active materials, for example, actives which have been identified as useful in the treatment of autoimmune disorders or conditions or in the alleviation of symptoms associated therewith. These actives can be broad-based actives, such as those that are useful in the treatment of a variety of autoimmune disorders or conditions or in the alleviation of symptoms associated with a variety of autoimmune disorders or conditions; or they may be more specific, for example, as in the case where the other active is specific for the treatment of the particular autoimmune disorder or condition with which the subject is afflicted or in the alleviation of symptoms associated with the particular autoimmune disorder or condition. As further illustration of the actives which can be additionally included in the above-described formulations (i.e., in addition to the RNA targeting compounds and in addition to non-active components), there can be mentioned actives which are conventionally employed to treat or otherwise alleviate the symptoms of myotonic dystrophy and/or related complications.

It will be appreciated that the actual preferred amount of RNA targeting compound to be administered according to the present invention will vary according to the particular RNA targeting compound being employed, the particular composition formulated, and the mode of administration. Many factors that may modify the action of the RNA targeting compound (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

By way of still further illustration, RNA targeting compounds of the present invention can be used to interfere with the interaction of muscleblind protein with RNA molecules that comprise CUG repeats. The method includes contacting the RNA molecules with an RNA targeting compound of the present invention in which some or all of the RNA binding ligands bind to a CUG RNA triplet repeat motif. Illustratively, the RNA binding ligands can be the same or different and can be selected from aminoglycoside sugars and bis-benzimidazoles, examples of which include those discussed above. Contacting can be carried out in vivo, ex vivo, or in vitro. In those cases where contacting is carried out in vivo, for example, in a subject suffering from myotonic dystrophy and/or other diseases or conditions involving the interaction of muscleblind protein with RNA molecules that comprise CUG repeats, the RNA targeting compound can be administered by any of the routes and in any of the compositions described above.

The present invention is further illustrated by the following non-limiting examples.

EXAMPLES

Example 1

Preparation of Multivalent RNA-Targeting Compounds Displaying Kanamycin A RNA Binding Ligands This Example 1 and in the following Examples 2-4 describe methods to prepare multivalent oligomers that target RNA. These oligomers are decorated with multiple copies of a single ligand or several different ligands that bind to an RNA motif. Ligands are multivalently displayed on peptoid polymers [31] that are functionalized with azides suitable for conjugation to ligands that display an alkyne via a 1,3 dipolar Huisgen cycloaddition reaction [32-34]. Also described are the design and synthesis of peptoids that vary the spacing between the ligands by coupling methylamine into a growing peptoid chain.

To illustrate the present invention, these examples describe the synthesis of peptoids that display 6'-N-5-hexynoate kanamycin A with varying spacing is described. We have identified this kanamycin derivative as a lead compound for binding to the 5'CUG/3'GUC motif that is present in multiple copies in a RNA that causes a form of muscular dystrophy called myotonic dystrophy ("DM") [35-41]. The presence of an expanded 5'CUG/3'GUC repeat ($CUG_n$) binds to muscleblind protein, preventing normal muscle function and causing DM. Disruption of muscleblind-$CUG_n$ by multivalently displayed kanamycin A could be the first treatment of the cause of DM.

Example 2

Preparation of RNA Binding Ligands

N-Succinimidyl-5-hexynoate was prepared using the procedure described below:

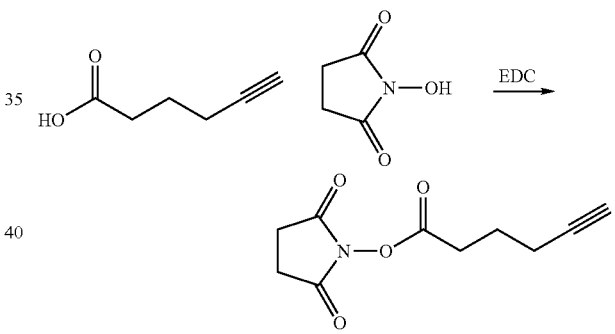

5-hexynoic acid (1 g, 8.3 mmole) was dissolved in 4 mL of a mixture of chloroform and DMF (9:1) and stirred. To this solution was added N-hydroxyl succinimide (0.95 g, 8.3 mmole) and N-(3-dimethylaminopropyl)-N'-ethylcarbodimide ("EDC") (1.58 g, 8.3 mmole), and the reaction was stirred overnight. The reaction was then diluted to 100 mL with methylene chloride and extracted with 0.1 N HCl (3×50 mL) and 5% $NaHCO_3$ (3×50 mL), dried over $MgSO_4$, and concentrated. The crude reaction mixture was used for all subsequent experiments (1.1 g, yield 60%). TLC analysis (3:7 EtOAc:$CH_2Cl_2$) showed a single product ($R_f$ 0.70).

N-benzyloxycarbonyloxy-5-norebornene-endo-2,3 dicarboximide was prepared using the procedure described below:

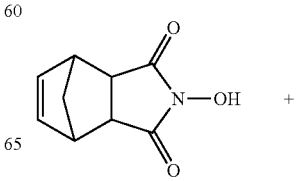

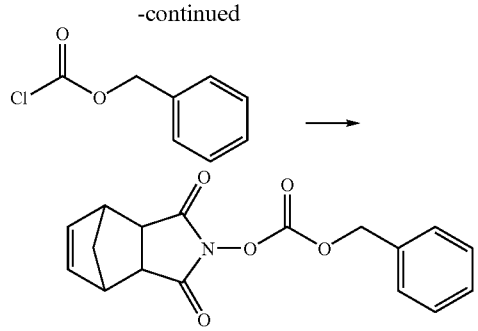

A synthesis of this compound using phosgene has been reported [42]. To eliminate the use of phosgene, a new and safer synthesis was developed. This compound was used in the synthesis of 1,3,3''-tri-N-(tert-butoxycarbon-yl)-kanamycin A and 1,3,3''-tri-N-(tert-butoxycarbon-yl)-neamine, as described [43]. Endo-N-hydroxy-5-norbornene-2,3-dicarboximide (10 g, 56 mmole) was dissolved in 100 mL of CH$_2$Cl$_2$ and 5 mL of pyridine and stirred in an ice bath. Bezylchloroformate was added, and the solution was stirred overnight and warmed to room temperature. The next morning, the solution was heated at 48° C. for 3 h. Solvent was removed via rotovap, and the solid was recrystallized from 90% aqueous MeOH to afford clear needles (10.1 g, 31 mmole, 57% yield). The spectrum $^1$H NMR spectrum was identical to that reported [42].

1,3,3'-Tri-N-(tert-butoxycarbonyl)-6'-N-5-hexyno-ate-kanamycin A was prepared using the procedure described below:

To a solution of 1,3,3''-tri-N-(tert-butoxycarbonyl)-kanamycin A [43] (200 mg, 255 µmol) in 6.0 mL of DMSO was added N-succinimidyl-5-hexynoate (140 mg, 714 µmol, 2.8 eq), and the reaction was stirred overnight. The reaction mixture was evaporated in a speed vac and purified by silica gel chromatography (CHCl$_3$:MeOH:NH$_4$OH, 4:1:0.1) to give the desired product (155 mg, 166 µmol, 65%, R$_f$=0.2).

6'-N-5-Hexynoatekanamycin A trifluoroactetic acid salt (31) was prepared using the procedure described below:

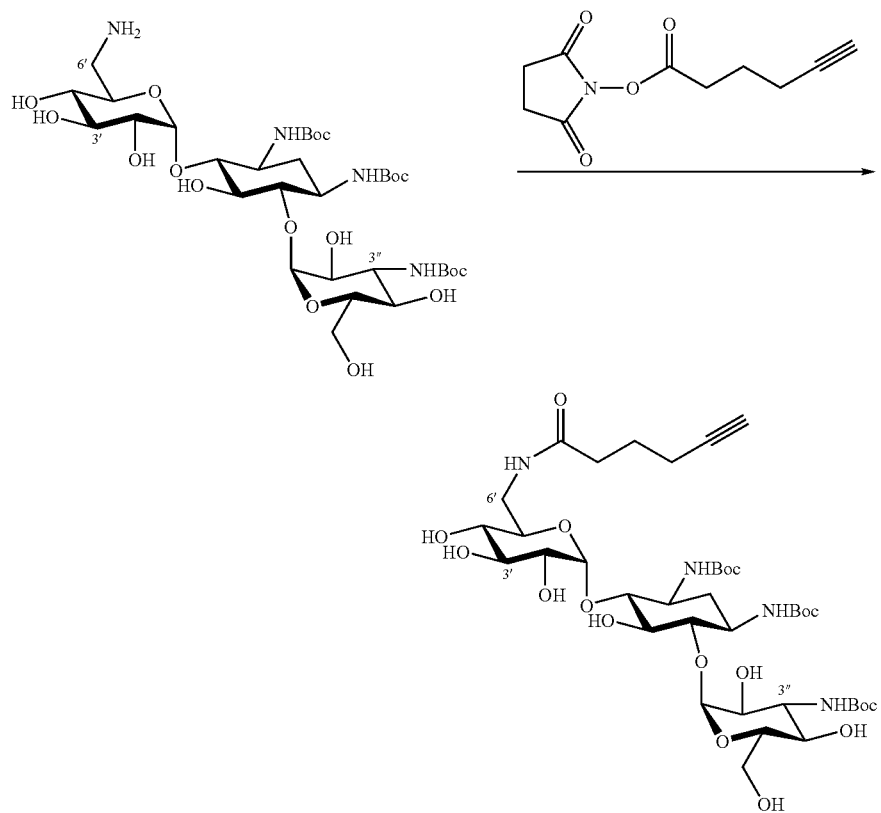

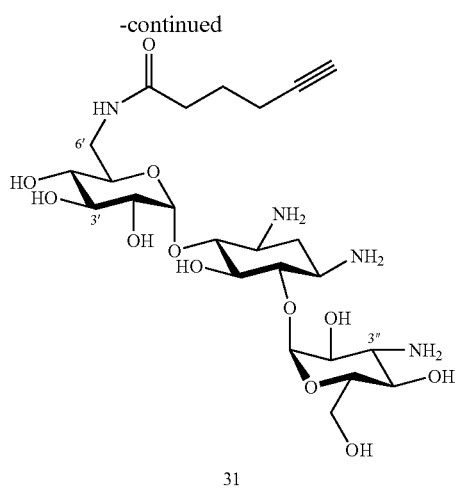

31

1,3,3''-Tri-N-(tert-butoxycarbonyl)-6'-N-5-hexynoate-kanamycin A (95 mg, 105 μmol) was dissolved in 10 mL of a mixture of CH$_2$Cl$_2$ and trifluoroacetic acid ("TFA") (1:1) and stirred for 1 h at room temperature. The reaction was diluted with 10 mL of toluene and concentrated. Then an additional portion of toluene was added, and the reaction was concentrated again. A yellow oil was obtained that was dissolved in 10 mL of nanopure water and lyophilized. A tan solid was isolated, and the solid was placed into Eppendorf tubes into which 4 mL of diethyl ether was added. The tubes were tumbled for 2 h. The tubes were centrifuged to pellet the solid, and the ether was decanted. Residual solvent was removed via vacuum concentration, and a white solid was obtained (45 mg, 80 μmole, 76%).

1,3,2'-Tri-N-(tert-butoxycarbonyl)-6'-N-5-hexynoateneamine was prepared using the procedure described below:

reaction was evaporated in vacuo and purified via column chromatography (CHCl$_3$:MeOH:NH$_4$OH, 4:1:0.1) to give the desired product (408 mg, 560 μmol, 74%, R$_f$=0.2).

6'-N-5-Hexynoateneamine trifluoroactetic acid salt was prepared using the procedure described below:

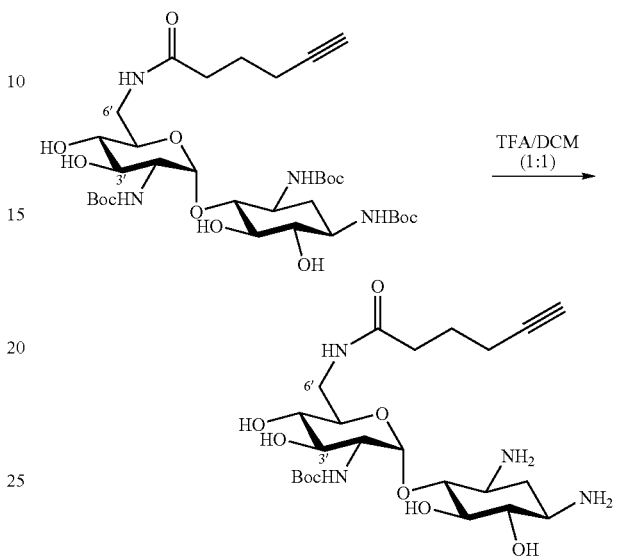

1,3,2'-Tri-N-(tert-butoxycarbonyl)-6'-N-5-hexynoate-neamine (320 mg, 447 μmole) was added to 10 mL of 1:1 TFA:DCM, and the reaction was stirred at room temperature for 1 h. A 10 mL aliquot of toluene was added to the solution, and it was concentrated in vacuo. An additional 10 mL of toluene was added and evaporated. The sample was then dissolved in 4 mL of water and evaporated in a vacuum concentrator to

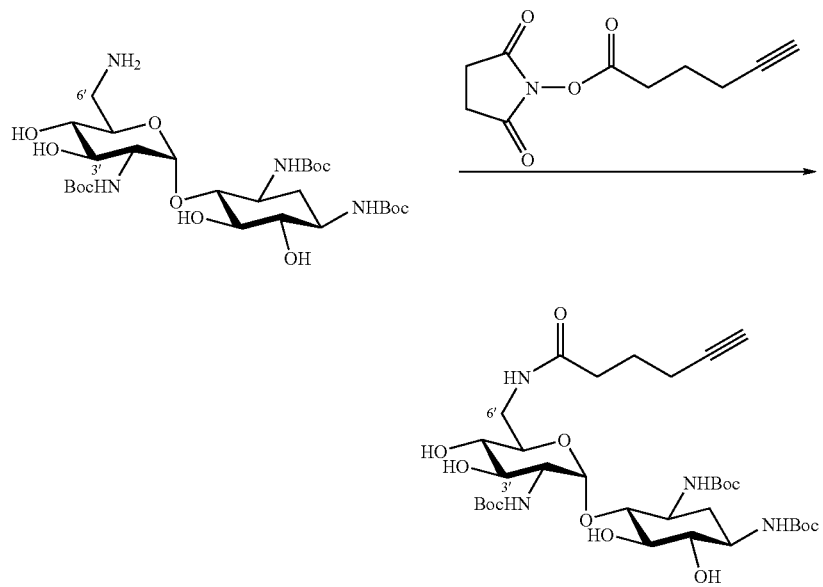

To a solution of 1,3,3''-tri-N-(tert-butoxycarbonyl)-neamine [43] (480 mg, 770 μmol) in 25.0 mL of MeOH with 200 μl of triethylamine was added N-succinimidyl-5-hexynoate (150 mg, 730 μmol), and the reaction was stirred overnight. The obtain a tan solid. To the solids was added 10 mL of diethyl ether, and the solution was stirred for an hour. The solids were filtered, and the remaining ether removed via vacuum concentration to afford a white solid (180 mg, 432 μmol, 97%).

Example 3

Figure 3A:
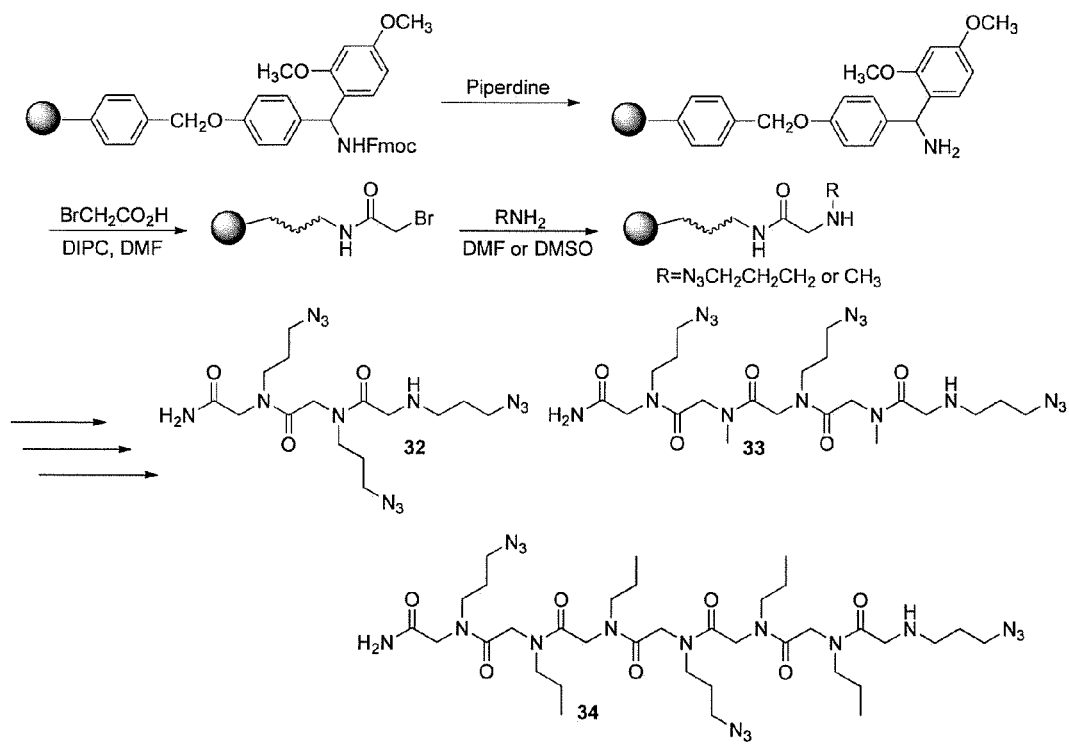
Figure 3B:
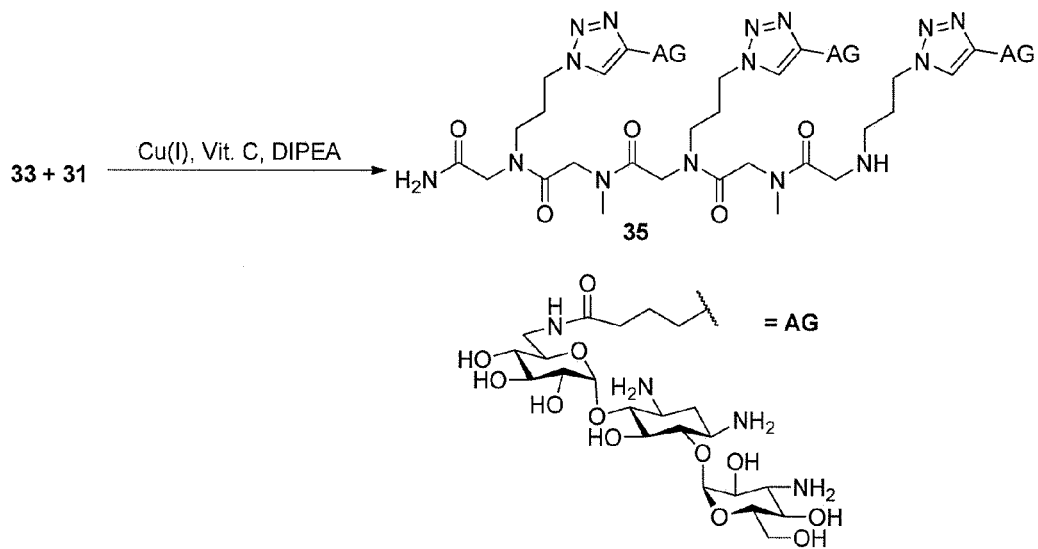
FIG. 3B is a reaction scheme for making a compound of the present invention.

Synthesis of Peptoid Oligomers Displaying Azides for Multivalent Display of RNA-Targeting Ligands FIG. 3A shows a schematic of the synthesis of multivalent peptoid oligomers to display multiple copies of 6'-N-5-hexynoate kanamycin A. Use of methylamine as a reactant in the synthesis allowed variation in the spacing of the 6'-N-5-hexynoate kanamycin A RNA-targeting ligand along the peptoid backbone, as can be seen in the azide-displaying peptoids 32, 33, and 34 (FIG. 3A). The azide-displaying peptoids are then conjugated to 6'-N-5-hexynoate kanamycin A using Cu(I) catalyst conditions to produce RNA targeting compound 35, as shown in FIG. 3B. In FIG. 3B, the group identified as "AG" has structure 36.

A description of the peptoid synthesis procedure (illustrated in FIG. 3A) is set forth below.

A 100 mg portion of Fmoc-Rink amide resin (0.67 mmol/g loading) was prepared for the first coupling step in a 10 mL solid-phase reaction flask (Chem Glass) by swelling for 20 min in DMF followed by washing with methanol and then dichloromethane. A 2 mL solution of 20% piperidine in DMF was added to the resin, and the resin was shaken at room temperature for 20 min. The solvent was removed, and the step was repeated. The solution was then washed with DMF and DCM (2×4 mL each) and then with anhydrous DMF (3×4 mL).

The first coupling of bromoacetic acid was accomplished by adding 2 mL of 1 M bromoacetic acid in DMF to the resin along with 400 mL of diisopropylcarbodiimide ("DIPC"). The solution was then placed into a conventional microwave oven and heated 3×10 s on the defrost setting. The flask was removed and manually shaken to mix the resin between each microwave incubation. The flask was then shaken at 37° C. for 20 min. The reagents were drained, and the coupling steps were repeated. After the second coupling, the resin was washed with DCM and DMF (2×4 mL each) and finally with anhydrous DMF (3×4 mL).

The resin was then coupled to 3-azidopropyl-amine (200 µL, 3 mmol) in 2 mL of DMF, and the reaction flask was heated in a microwave, incubated at 37° C., and washed as described above. For peptoid 32, all subsequent couplings used 3-azidopropylamine. For peptoids 33 and 34, methylamine was used at different steps to vary the spacing of the azide on the peptoid chain. Methylamine was coupled by incubating the resin with 2 mL of a 2 M solution of methylamine in tetrahydro-furan ("THF"), as described for the bromoacetic acid coupling; and each methylamine coupling was repeated 3 times. Each of these steps was alternated until a peptoid of the desired composition was obtained (33 and 34).

After all coupling steps, the resin was washed with methanol and DCM (4×3 mL each), and the peptoids were cleaved from the resin by adding 2 mL of a deprotection cocktail composed of 95:5 trifluoroacetic acid ("TFA"):$H_2O$. The reaction flask was shaken at room temperature for 30 min. The solvent containing the crude peptoid was removed from the resin, and the resin was deprotected again with 3×2 mL of deprotection cocktail. The solutions containing crude peptoid were combined and dried in a speed vac concentrator. A yellow/tan viscous oil was obtained. The peptoids were then purified by using a Waters HPLC equipped with 3 µm 19×150 mm C8 column at 10 mL/min and UV detection at 218 nm. A gradient of 95% Water/5% acetonitrile (MeCN) with 0.1% TFA to 30% water/70% acetonitrile with 0.1% TFA over 30 min was applied to the system. The retention times for the peptoids were: 14.5 min for 32; 16.0 min for 33, and 24 min for 34. The samples were then subjected to analysis by mass spectrometry ("MS") to confirm the identity of the products. ESI-MS: 32, observed 438 (M+H$^+$); 33, observed 602 (M+Na$^+$); 34 observed 722 (M+H$^+$).

A description of the procedure used to couple the peptoids to 31 via click chemistry (illustrated in FIG. 3B) is set forth below.

Peptoids 32-34 were reacted with 31 using 2 equivalents of 31 relative to the loading of the azide on the peptoids. Typical reactions were completed with 5.7 µmole of pure peptoid and 34.2 µmole of 31. These reactions were completed in 4:1 dimethylsulfoxide ("DMSO"):$H_2O$ with 2 mM ascorbic acid, 200 µM of TBTA [32] (a Cu+ ligand that accelerates Huigsen 1,3 dipolar cycloaddition reactions), and 1 mM $CuSO_4$. After all of the reagents were added, the reaction vessel (a 2 mL Eppendorf tube) was sonicated to dissolve all reagents. The tube was then tumbled at room temperature overnight. Crude reactions were then purified by HPLC using the same conditions as described for peptoid purification above. Compounds had a typical retention time of 18 min for each compound. MALDI MS was used to confirm the identity of the products. The click product of 32+31: observed 2172 (M+H$^+$); click product (35) of 33+31: observed 2337 (M+Na$^+$); click product of 34+31: observed 2457 (M+H$^+$).

Example 4

Binding of 31 to an Oligonucleotide that Displays a Single Copy of 5'CUG/3'CUG Motif that, when Present in Multiple Copies of the DMPK gene, causes Myotonic Dystrophy A fluorescence-based assay was used to study the binding of 31 to several RNAs and DNAs. In order to complete these studies, we conjugated a fluorescein tag onto 31 by reacting fluorescein isothiocyanate with 3-azidopropylamine. The azide-labeled fluoresceine was conjugated to 31.

The synthesis of 5-(3-(3-azidopropyl)thioureido)-2-(3-hydroxy-6-oxo-6H-xanthen-9-yl)benzoic acid was carried out using the following procedure:

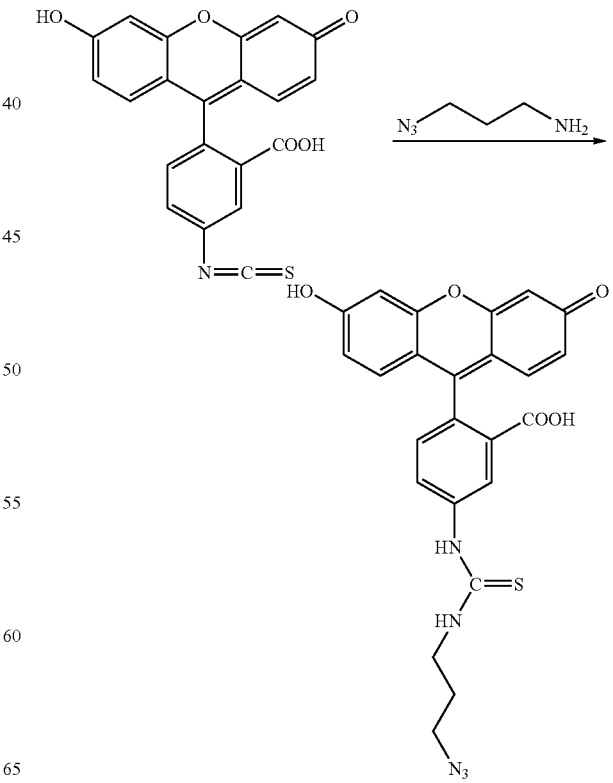

Fluorescein isothiocyanate (34 mg, 87 μmole) was dissolved in 500 μL of DMF with 15 μL of Hünig's base. Then 3-azidoproplyamine (1.3 eq, 10.5 mg, 12 μL) was added. The reaction was sonicated to dissolve all reagents and tumbled at room temperature overnight. An aliquot of the reaction was then subjected to mass spectrometry to confirm formation of the product and consumption of the starting material. (ESI+) found: 490.1 (M+H$^+$). The reaction was then placed into a speed vac overnight to remove the solvent and uncoupled 3-azidopropylamine. A quantitative yield was obtained.

Boc-protected fluorescein-labeled 6'-N-5-hexynoate kanamycin A was prepared using the procedure described below:

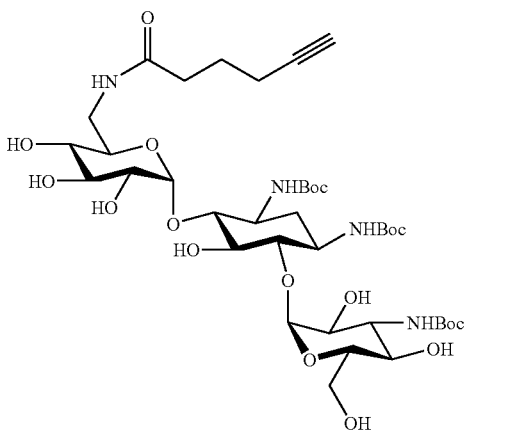

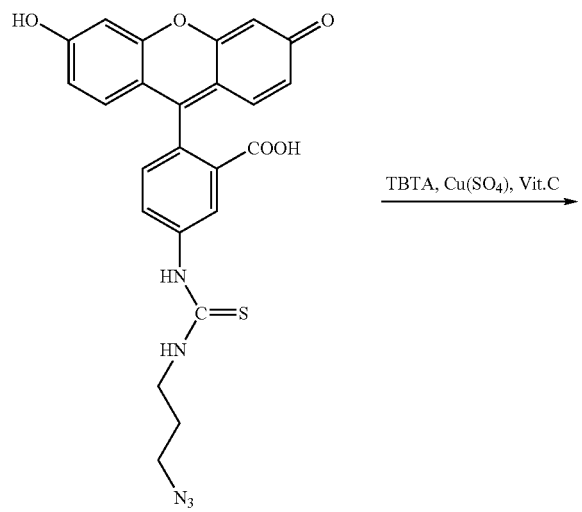

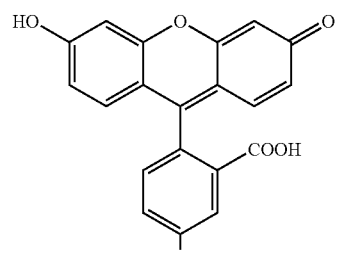

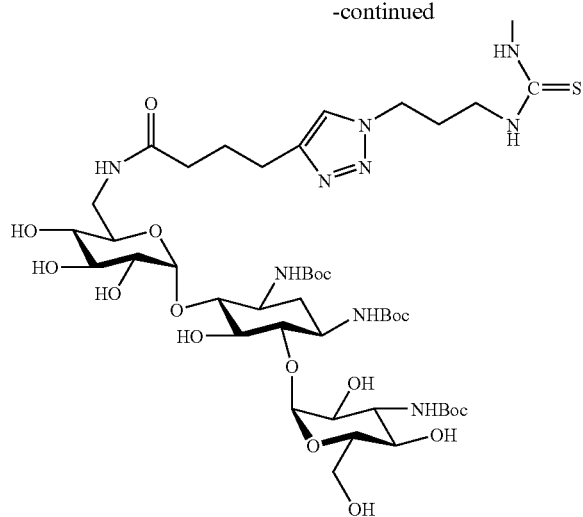

To a solution containing 1,3,3"-tri-N-(tert-butoxycarbon-yl)-6'-N-5-hexynoate kanamycin A (21.6 mg, 24 μmoles) in a 7:3 mixture of DMSO:$H_2O$ was added 5-(3-(3-azidopropyl)-thioureido)-2-(3-hydroxy-6-oxo-6H-xanthen-9-yl)benzoic acid (15 mg, 30 μmoles), 1 mM $CuSO_4$, 1 mM Vitamin C, and 100 μM of TBTA [32], and the reaction was tumbled overnight in an Eppendorf tube at 37° C. The reaction was analyzed by mass spectrometry to confirm formation of the product and consumption of the 6'-N-5-hexynoate kanamycin A starting material. (ESI+) found: 1368 (M+H⁺). The product was then purified via HPLC equipped with a Waters Symmetry C8 preparative column (7 μm, 19×150 mm). A flow rate of 10 mL/min and a gradient of methanol from 0 to 100% over 30 min was applied ($t_r$ product, 24.4 min). Isolated yield: 12 mg, 40%.

Fluorescein-labeled 6'-N-5-hexynoate kanamycin A was prepared using the procedure described below:

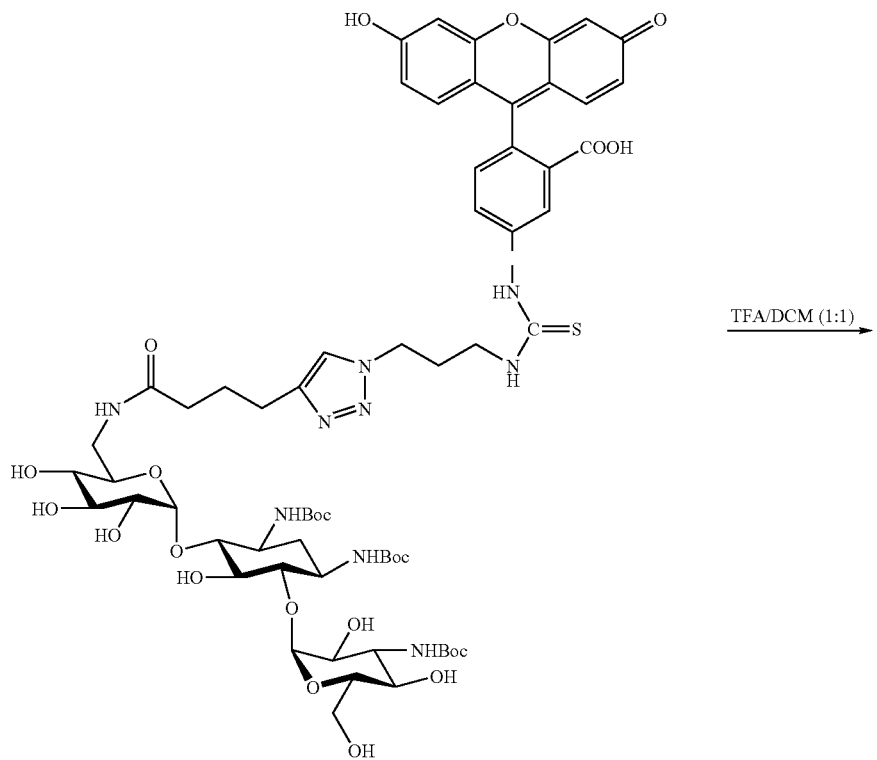

-continued

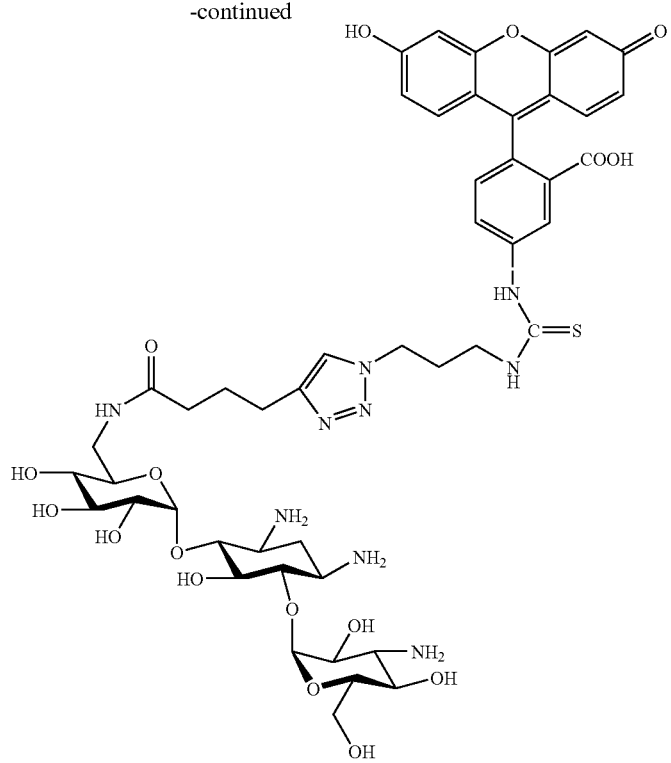

To a 500 μL solution containing 12 mg of Boc-protected fluorescein-labeled 6'-N-5-hexynoate kanamycin A was added 500 μL of trifluoroacetic acid, and the reaction was stirred for 30 min. The reaction was then diluted to 10 mL with toluene and evaporated to dryness. The product was then dissolved in water and concentrated in a speed vac overnight. The residue was tumbled twice in 1 mL of diethyl ether with the ether being removed between washes. The product was obtained as a fluorescent yellow/green solid. MS (ESI+): 1068 (100%, M+H$^+$) and 1090 (45%, M+Na$^+$). A quantitative yield was obtained.

Figure 4A:
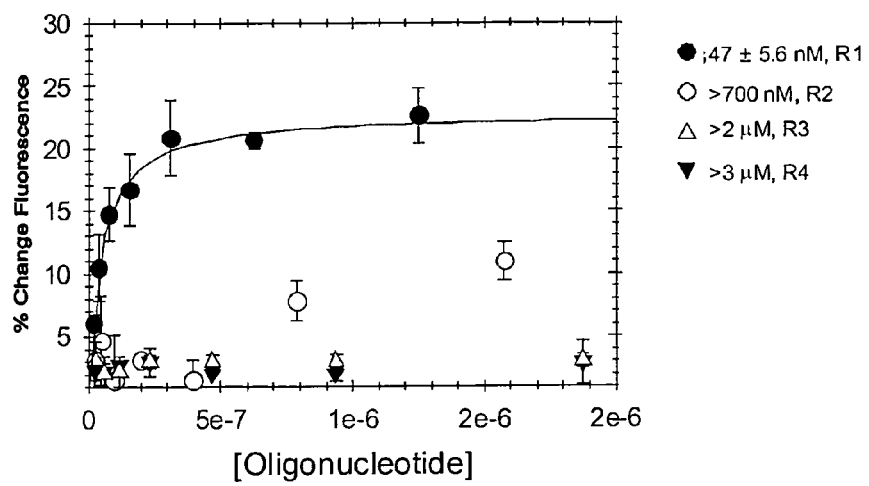
FIG. 4 is a graph showing the effect of various oligonucleotides on the fluorescence of a fluorescently-labeled RNA binding ligand that can be used in the compounds of the present invention.
Figure 4B:
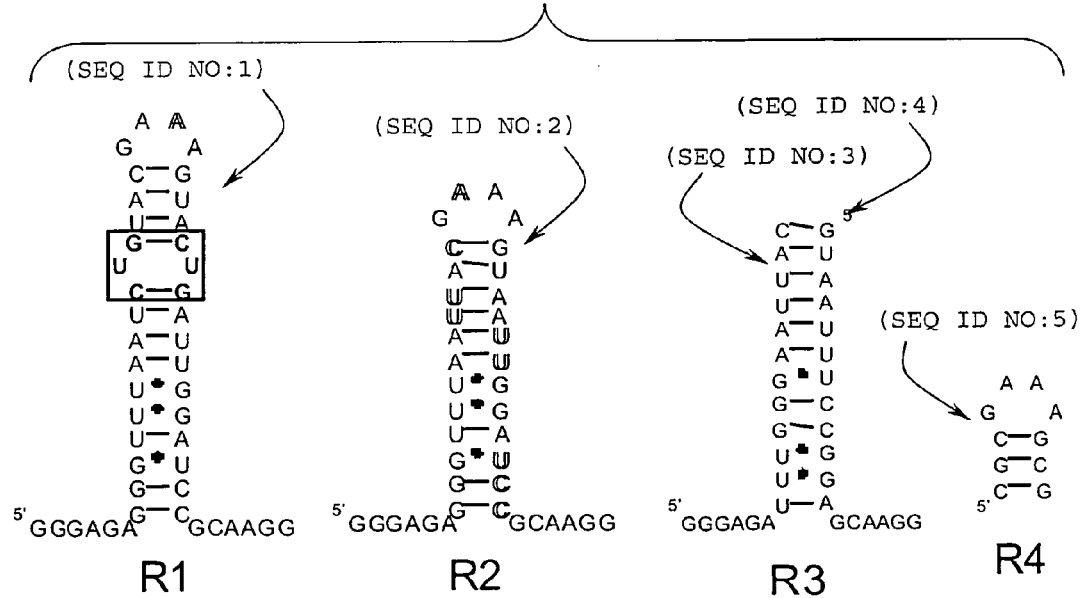

A fluorescence-based assay was used to determine the dissociation constants and the number of interacting sites of small molecule-internal loop interactions. More particularly, for the in solution affinity assays, serially diluted concentrations of RNA were annealed in 1×HB+40 μg/mL BSA at 60° C. for 5 min and allowed to slow cool on the benchtop. FITC-labeled 31 in 1×HB+40 μg/mL BSA was added to the solution of RNA at a final concentration of 10 nM. Samples were then placed into a well of a black 96-well plate. Samples were allowed to incubate for at least 30 min before reading the fluorescence on a Bio-Tek Synergy HT fluorescence plate reader set to FITC filters and a sensitivity between 38-40. Several different times were sampled to ensure that the fluorescence intensity was taken after these interactions reached equilibrium. Control experiments included incubation of a selected internal loop (concentration of 3 μM) with 10 nM FITC. No change in fluorescence was observed. The data were fit to one-site saturation curve in Sigma plot. When data was fit to a two-site saturation equation, the curve fit did not converge to the data. The binding data are shown in FIG. 4, along with the structures of the RNAs on which the assays were performed. The data show that 31 binds specifically to RNAs that have a single copy of the 5'CUG/3'GUC motif that causes myotonic dystrophy.

Figure 5:
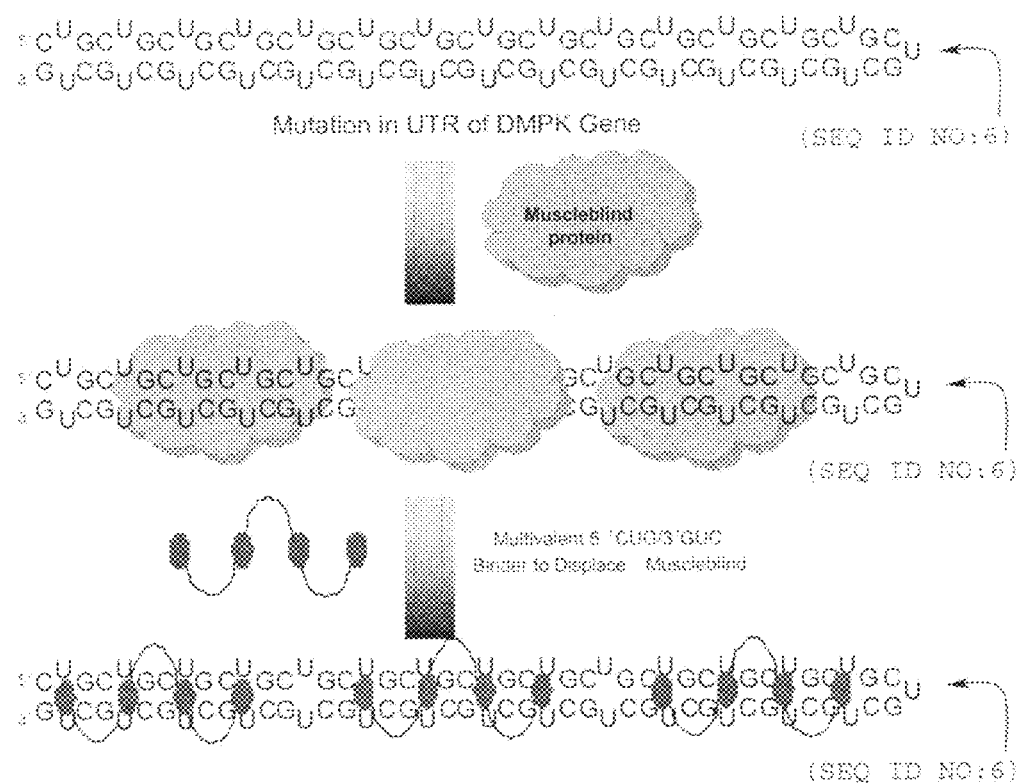
FIG. 5 is a schematic illustrating a strategy for using compounds of the present invention to inhibit muscleblind-$CUG_n$ interactions.

FIG. 5 is a schematic that outlines a strategy to use multivalent peptoids displaying 31 to inhibit muscleblind-CUG$_n$ interactions. As shown, the expanded triplet repeat folds into a hairpin structure that sequesters muscleblind and causes myotonic dystrophy. Experiments have been performed which show that multivalent peptoids displaying 31, prepared as described herein, binds unexpectedly well to RNAs that contain multiple CUG oligomers (e.g., r(CUG)$_{110}$), and it is believed that this binding will disrupt the muscleblind-CUG$_n$ interactions and can be used to treat myotonic dystrophy.

Example 5

Preparation of Multivalent RNA-Targeting Compounds Displaying Bisimidazole RNA Binding Ligands This Example 5 describes the synthesis of a multivalent RNA-targeting compound displaying a bisimidazole RNA binding ligand, Hoechst 33258 azide to target CUG$_{140}$.

Figure 6A:
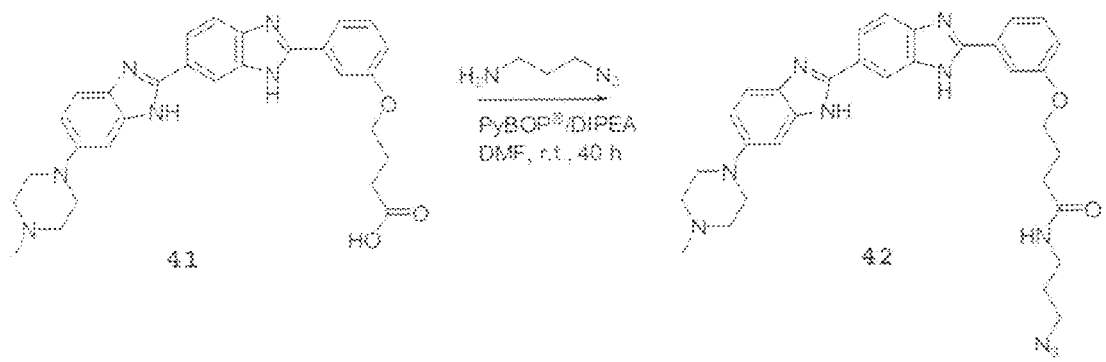
FIG. 6A is a reaction scheme showing structural formulae of RNA binding ligands that can be used to prepare compounds of the present invention and a way to convert one to the other.

Hoechst-azide derivative 42 was synthesized by a modified procedure [44] from Hoechst derivative 41 and 3-azidopropylamine as shown in FIG. 6A.

Figure 6B:
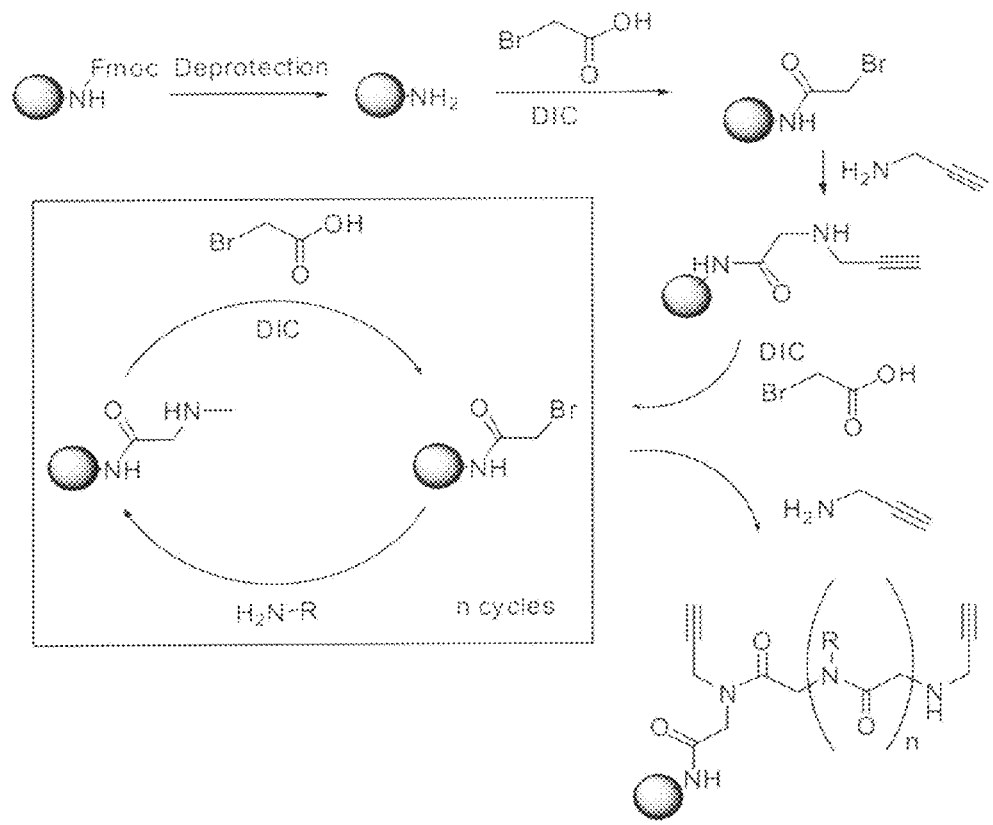
FIG. 6B is a reaction scheme for making peptoid backbones that can be used in the preparation of various compounds of the present invention.

Peptoid backbones were synthesized on a Rink amide resin solid support via standard protocol, as shown in FIG. 6B, using the methods analogous to those discussed in Example 3.

Figure 6C:
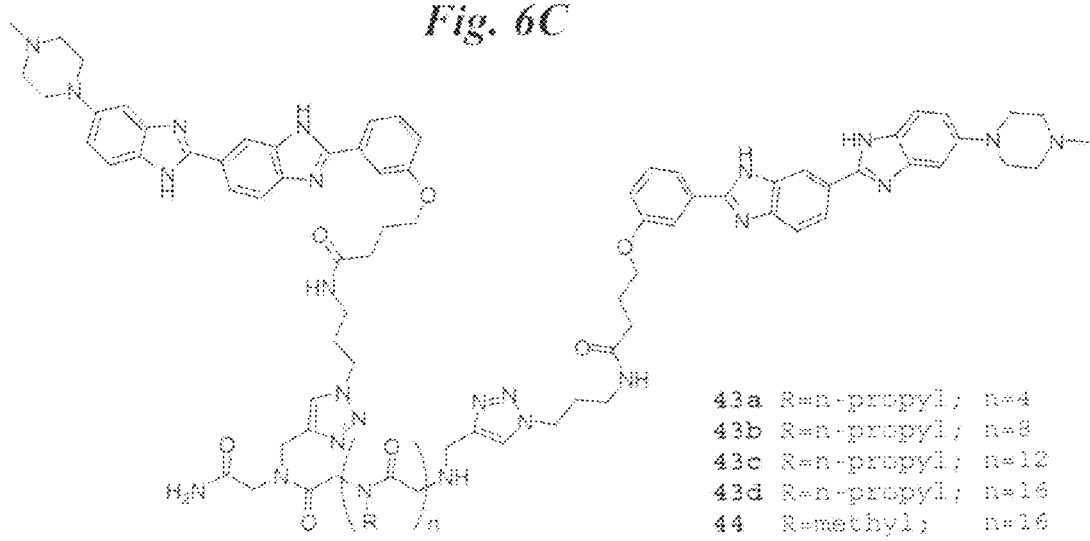
FIG. 6C is structural formulae of several compounds of the present invention.

Conjugation of Hoechst-azide 42 to the peptoid backbone was achieved via modified post-oligomerization click chemistry protocol [45] followed by cleavage. Following that procedure, five bivalent RNA-targeting compounds (43a, 43b, 43c, 43d, and 44) were isolated after HPLC purification. The products have the structure shown in FIG. 6C. In compounds 43a, 43b, 43c, and 43d, R is n-propyl, and n is 4, 8, 12, and 16, respectively. In compound 44, R is methyl, and n is 16.

The following method was used to prepare meta-(4-Hydroxybutyric acid)-Hoechst (41). A mixture of ethyl 4-(3- formylphenoxy)butanoate [46] (0.37 g, 2.1 mmol) and 4-(5-(4-methylpiperazin-1-yl)-1H-benzo[d]imidazol-2-yl)benzene-1,2-diamine [44], acetate salt (0.8 g, 2.1 mmol) in 45 mL of nitrobenzene was stirred at 140° C. for 36 h under argon. Then the solution was concentrated to dryness in vacuo, and the residue was triturated with ethyl ether (50 mL), filtered, and washed on the filter with ethyl ether (4×20 mL). The crude product was dried and dissolved in ethanol (15 mL) and then, to the solution, potassium hydroxide (0.47 g, 8 mmol) was added, and the mixture was refluxed for 4 h. The reaction was cooled down to room temperature, diluted with water (15 mL), and saturated with $CO_2$. In about 1 h, crystals of the product started to precipitate. The product was filtered, washed on the filter with ethyl ether (4×20 mL), and dried. Yield 0.9 g (84%). MS-ESI(+) 511 (M+H$^+$).

The following method was used to prepare meta-(N-(3-azidopropyl)-4-hydroxybutanamide)-Hoechst, hexafluorophosphate mono salt (42). A mixture of meta-(4-hydroxybutyric acid)-Hoechst (41) (0.9 g, 1.76 mmol), PyBOP™ (1.4 g, 2.64 mmol), and diisopropylethylamine (0.68 g, 5.28 mmol) in DMF (15 mL) was stirred under argon at room temperature for 30 min, and then 3-azidopropylamine (0.27 g, 2.64 mmol) was added. The reaction was stirred at room temperature for 40 h while monitoring the reaction progress by TLC (ethyl acetate/methanol/triethylamine, 16:8:1). Then the solution was concentrated in vacuo to a thick, gummy residue. The residue was washed with water (3×20 mL) and crystallized from ethanol (10 mL), providing off-white crystals of the product. Yield 0.7 g (54%). MS-ESI(+) 593 (M+H$^+$), MS-ESI (−) 145 (60%, PF6$^−$), 591 (30%, M$^−$), 637 (100%, M+HCO$_2^−$).

Example 6

Figure 7A:
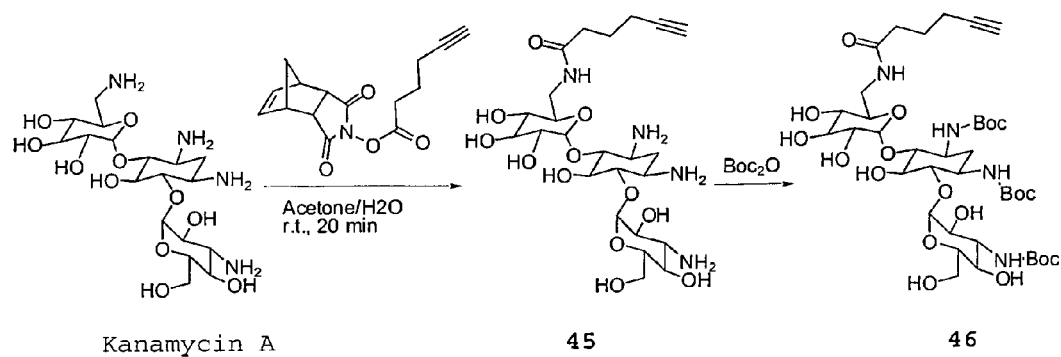
FIGS. 7A, 7B, and 7E are reaction schemes showing structural formulae of various RNA binding ligands that can be used in the preparation of compounds of the present invention and ways to convert one to another.
Figure 7B:
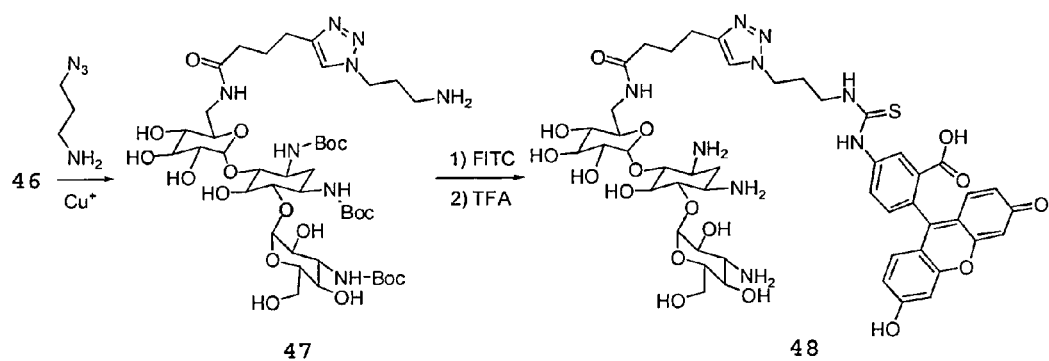

Preparation of Kanamycin-6'-N-Hexynoate and Use Thereof in the Preparation of RNA-Targeting Compounds Kanamycin-6'-N-hexynoate (45) was synthesized by analogy to the reported regio- and chemo-selective 6'-N-derivatization procedure [46] followed by one-pot Boc-protection to yield the kanamycin-alkyne derivative 46. The synthetic scheme is set forth in FIG. 7A.

Click chemistry modification of kanamycin-alkyne derivative 46 with 1-amino-3-azidopro-pane followed by treatment with FITC and deprotection led to a monovalent fluorescein-labeled ligand 48.

Figure 7C:
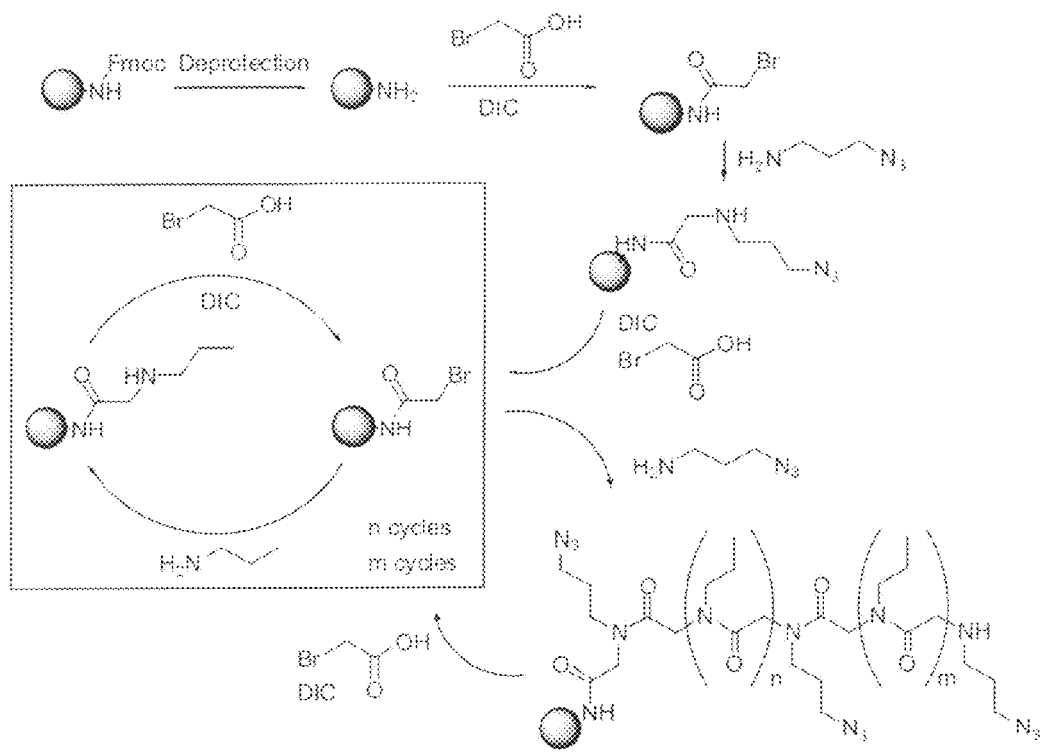
FIG. 7C is a reaction scheme for making peptoid backbones that can be used in the preparation of various compounds of the present invention.

Preparation of Peptoid Backbones was Carried out using the scheme set forth in FIG. 7C. Briefly, peptoid backbones were synthesized similarly to the scheme utilized for the Hoechst-based ligands except, here, the peptoid backbones have an azide display instead of alkyne one.

Figure 7D:
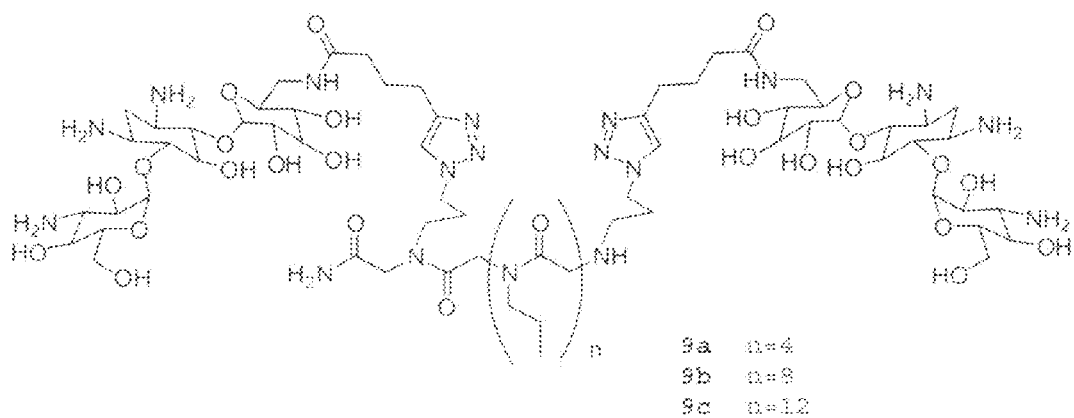
FIGS. 7D and 7F are structural formulae of several compounds of the present invention.

Conjugation of kanamycin-alkyne derivative 46 to the peptoid backbone was carried out similarly to the Hoechst click protocol followed by cleavage with simultaneous Boc-protective group removal. Following that procedure, three bivalent RNA-targeting compounds (49a, 49b, and 49c) were isolated after HPLC purification. The products have the structure shown in FIG. 7D. In compounds 49a, 49b, and 49c, n is 4, 8, and 12, respectively.

Figure 7E:
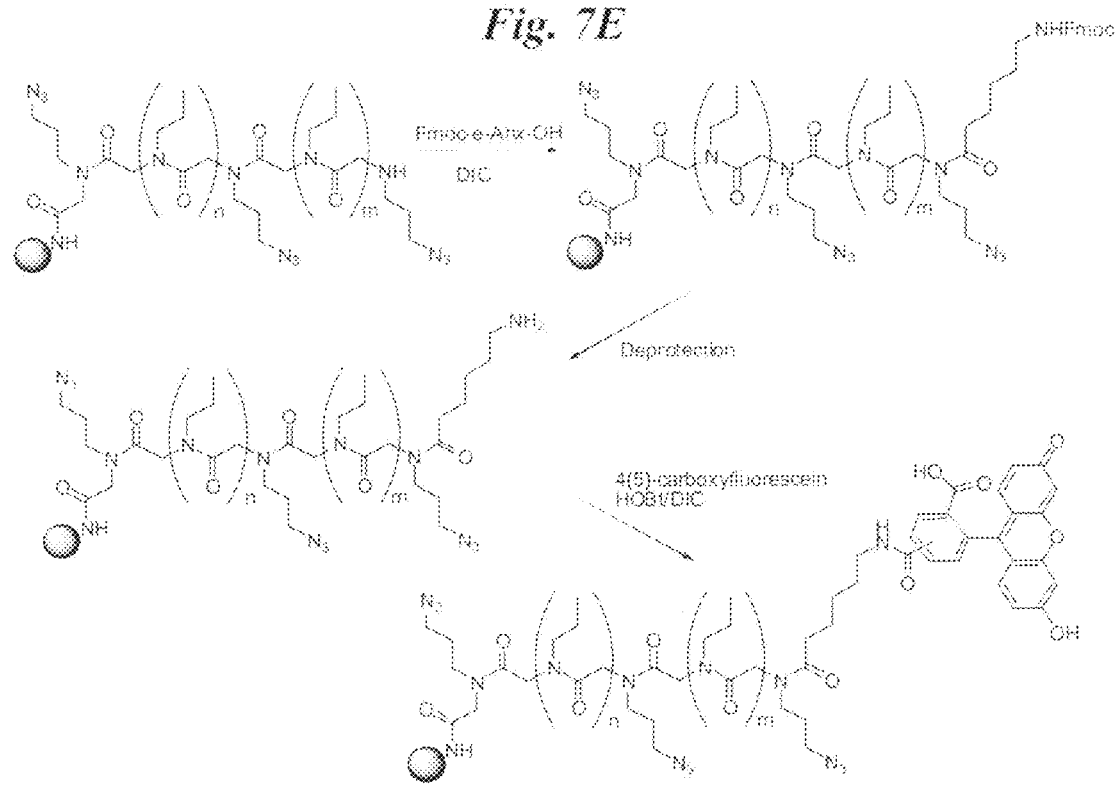

For easier quantification and binding assays, peptoids with terminal fluorescein marker attached through a 6-aminohexanoic (a 6-aminopentylcarbonyl) linker [47] were synthesized using the preparative scheme set forth in FIG. 7E.

Figure 7F:
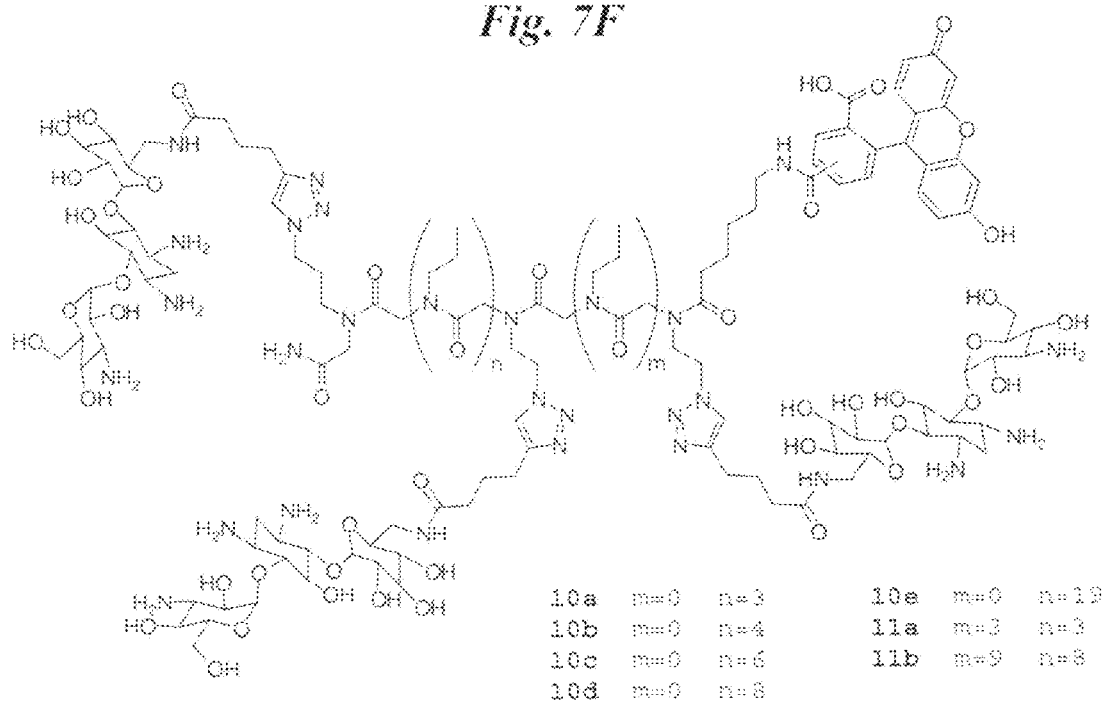

After conjugation with kanamycin-alkyne derivative 46 and subsequent cleavage from the resin and HPLC purification, five bivalent and two trivalent ligands were isolated. The products have the structure shown in FIG. 7F. In compounds 10a, 10b, 10c, 10d, 10e, m is 0, and n is 3, 4, 6, 8, and 19, respectively. In compound 11a, m is 3, and n is 3; and in compound 11a, m is 9, and n is 8.

Example 7

Experimental Procedures and Details Used in the Preparation of Multivalent RNA-Targeting Compounds Displaying Bisimidazole and Kanamycin RNA Binding Ligands This Example 7 further describes the experimental procedures and details used in Examples 5 and 6.

The following HPLC procedures were used.

Synthetic purity was evaluated by analytical HPLC on a Waters SYMMETRY™ C8 5 μm 4.6×150 mm column at room temperature on a Waters 1525 Binary HPLC Pump equipped with Waters 2487 Dual λ Absorbance Detector system at 1 mL/min flow rate and 218/254 nm wavelength. Linear gradient 5% to 95% B in A over 35 min (A: water+0.1% TFA, B: methanol+0.1% TFA, v/v).

Purification of the peptoid ligands was performed by preparative HPLC on a SYMMETRYPREP™ C8 7 μm 19×150 mm column at room temperature on a Waters 1525 Binary HPLC Pump equipped with Waters 2487 Dual λ Absorbance Detector system at 10 mL/min flow rate and 218/254 nm wavelength.

The following method was used to prepare meta-(4-Hydroxybutyric acid)-Hoechst (41). A mixture of ethyl 4-(3-formylphenoxy)butanoate [48] (0.37 g, 2.1 mmol) and 4-(5-(4-methylpiperazin-1-yl)-1H-benzo[d]imidazol-2-yl)benzene-1,2-diamine [44], acetate salt (0.8 g, 2.1 mmol) in 45 mL of nitrobenzene was stirred at 140° C. for 36 h under argon. Then the solution was concentrated to dryness in vacuo, and the residue was triturated with ethyl ether (50 mL), filtered, and washed on the filter with ethyl ether (4×20 mL). The crude product was dried and dissolved in ethanol (15 mL) and then, to the solution, potassium hydroxide (0.47 g, 8 mmol) was added, and the mixture was refluxed for 4 h. The reaction was cooled down to room temperature, diluted with water (15 mL), and saturated with $CO_2$. In about 1 h, crystals of the product started to precipitate. The product was filtered, washed on the filter with ethyl ether (4×20 mL), and dried. Yield 0.9 g (84%). MS-ESI(+) 511 (M+H$^+$).

The following method was used to prepare meta-(N-(3-azidopropyl)-4-hydroxybutanamide)-Hoechst, hexafluorophosphate mono salt (42). A mixture of meta-(4-hydroxybutyric acid)-Hoechst (41) (0.9 g, 1.76 mmol), PyBOP™ (1.4 g, 2.64 mmol), and diisopropylethylamine (0.68 g, 5.28 mmol) in DMF (15 mL) was stirred under argon at room temperature for 30 min, and then 3-azidopropylamine (0.27 g, 2.64 mmol) was added. The reaction was stirred at room temperature for 40 h while monitoring the reaction progress by TLC (ethyl acetate/methanol/triethylamine, 16:8:1). Then the solution was concentrated in vacuo to a thick, gummy residue. The residue was washed with water (3×20 mL) and crystallized from ethanol (10 mL), providing off-white crystals of the product. Yield 0.7 g (54%). MS-ESI(+) 593 (M+H$^+$), MS-ESI (−) 145 (60%, PF6$^−$), 591 (30%, M$^−$), 637 (100%, M+HCO$_2^−$).

The following method was used to prepare 1,3,3"-tri-N-(tert-butoxycarbonyl)-kanamycin-6'-N-hexynoate (46). To a solution of kanamycin A free base (0.2 g, 0.4 mmol) in an acetone-water mixture (1:1, 10 mL), N-(6-hexynoyloxy)-5-norbornene-2,3-dicarboximide (0.1 g, 0.36 mmol) was added, and the reaction was stirred at room temperature for 20 min. Then, to the mixture, Boc anhydride (0.53 g, 2.4 mmol) was added, and the reaction was stirred 24 h at room temperature. White precipitate was filtered, washed with ethyl ether (6×5 mL), and dried, providing pure product identical to the reference sample obtained via a different synthetic scheme. Yield 0.17 g (47%). MS-ESI(+) 879 (M+H$^+$).

The following method was used to prepare 6'-N-fluorescein labeled kanamycin (48). To a solution of 1,3,3"-tri-N-(tert-butoxycarbonyl)-kanamycin-6'-N-hexynoate (46) (9 mg, 10 µmol) in DMSO (81 µL), 3-azidopropylamine (6 µL, 50 µmol) and solutions of TRIS.HCl (1 µL, 1M in water), CuSO$_4$ (10 µL, 0.01M in water), ascorbic acid (1 µL, 0.1M in water), and TBTA (1 µL, 0.01 M in DMSO/tert-butanol, 1:4) were added. The mixture was incubated at 60° C. overnight and concentrated to dryness. The residue was dissolved in DMSO (0.2 mL), and, to the solution, fluoresceinisothiocyanate ("FITC") (8 mg, 20 µmol) and triethylamine (7 µL, 50 µmol) were added. The reaction was incubated at 40° C. for 1 h and then concentrated to dryness. The residue was dissolved in methanol and purified by preparative HPLC. Combined fractions were concentrated to dryness, and, to the residue, a mixture of TFA/DCM/water (60:40:2, 0.5 mL) was added. The solution was gently shaken at room temperature for 1 h and concentrated to dryness. After lyophilization from water, 7.3 mg (5.2 µmol) of the product (tris-trifluoroacetate salt) were obtained. MS-ESI(+) 1068 (100%, M+H$^+$), 535 (50%, M+2H$^+$).

The general protocol for the peptoid synthesis is described below. The peptoid oligomers were synthesized at room temperature (22° C.) in BioRad POLY-PREP™ chromatography columns (0.8×4 cm) orthogonally installed on a plate of Thermolyne MAXI-MIX III™ shaker. Fmoc-protected Rink amide polystyrene resin (AnaSpec) with a substitution level 0.45 mmol/g (23 mg, 10 µmol) was swollen in DCM (1 mL) for 20 min, drained, and deprotected with 1 mL of 20% piperidine in DMF for 40 min with shaking at 800 rpm, followed by draining and then rinsing with DMF (6×3/6×3 mL).

The coupling step was carried out as follows. To the resin-bound amine bromoacetic acid (0.2 mL, 1M in DMF) and diisopropylcarbodiimide ("DIC") (0.2 mL, 1M in DMF) were added. The resin was shaken for 20 min at 1000 rpm, drained, and then rinsed with DMF (5×2/5×2 mL).

The displacement step involved a two step process. In one step, a click counterpart was introduced by sequentially adding, into a column, DMF (0.2 mL) and corresponding amine (20 µL of either 3-azidopropylamine or propargylamine). The resin was shaken for 3 h at 1000 rpm, drained, and then rinsed with DMF (5×2/5×2 mL). In the other step, the chain was extended with a spacer by sequentially adding, into a column, DMF (0.2 mL) and propyl amine (50 µL). The resin was shaken for 20 min at 1000 rpm, drained, and then rinsed with DMF (5×2/5×2 mL).

The following general protocol was followed for the peptoid post-oligomerization ligand introduction, click chemistry. The resin-bound oligomer was washed with methanol (3×2 mL) and dichloromethane (3×2 mL) and dried under stream of air, and a small portion of the resin was cleaved and analyzed by HPLC and MS-ESI prior to a conjugation step. Then, into a resin-bound oligomer containing column, a click counterpart (4 equivalents per conjugation site) was added. The column was sealed with a rubber septum and purged with argon for 20 min. Then the column was capped from another side, and 2 mL of the pre-prepared catalyst solution (0.1M copper acetate, 1M diisopropylethylamine, 0.1M ascorbic acid, and 0.01M TBTA in pyridine/DMF, 3:7) were loaded into the column under argon. The reaction was sonicated (Branson BRANSONIC™ 5210, 140 watts, 47 kHz) in darkness at 40° C. with periodic vortexing for 36 h. The click solution was drained; and the resin was rinsed with DMF (5×2 mL), 2% ascorbic acid in pyridine (5×2 mL), and DMF (5×2/5×2 mL) and washed with methanol (3×2 mL) and dichloromethane (3×2 mL). The product was cleaved from the resin in a mixture of TFA/DCM/water (60:40:2, 2×1 mL) with shaking (600 rpm) at room temperature for 1 h. The filtrate was concentrated under a stream of air, the residue was dissolved in water, and product was isolated by preparative HPLC. Fractions were analyzed by MS-ESI. Combined fractions of the product were concentrated to dryness, and the product was lyophilized from water.

The following general protocol was followed for peptoid post-oligomerization fluorescein labeling. The resin-bound oligomer was washed with methanol (3×2 mL) and DCM (3×2 mL) and dried under a stream of air; and Fmoc-6-aminohexanoic acid ("Fmoc-e-Ahx-OH") (18 mg, 50 µmol) and DIC (0.2 mL, 1M in DMF) were added. The resin was shaken at room temperature for 2 h at 800 rpm, drained, rinsed with DMF (5×2/5×2 mL), and deprotected with 1 mL of 20% piperidine in DMF for 50 min with shaking at 800 rpm, followed by draining and then rinsing with DMF (6×3/6×3 mL). Then, into a column, 4(5)-carboxyfluorescein (19 mg, 50 µmol), N-hydroxybenzotriazole (11 mg, 80 µmol), DMF (0.1 mL), and DIC (0.2 mL, 1M in DMF) were added. The resin was shaken at room temperature for 2 h at 800 rpm, drained, washed with DMF (6×3 mL), and rinsed with DMF (5×2/5×2 mL). The resulting resin-bound oligomer with fluorescein marker was then conjugated with the corresponding ligand.

Although the invention has been described in detail for the purpose of illustration, it is understood that such detail is solely for that purpose, and variations can be made therein by those skilled in the art without departing from the spirit and scope of the invention which is defined by the claims that are set forth below after the section entitled "References".

REFERENCES

1. Doudna, J. A. (2000) Structural genomics of RNA, Nat. Struct. Biol. 7 Suppl., 954-956.
2. Batey, R. T., et al. (1999) Tertiary motifs in RNA structure and folding, Angew. Chem., Int. Ed. Engl. 38, 2326-2343.
3. Zaug, A. J., et al. (1986) The intervening sequence RNA of tetrahymena is an enzyme, Science 231, 470-475.
4. Lagos-Quintana, M., et al. (2001) Identification of novel genes coding for small expressed RNAs, Science 294, 853-858.
5. Winkler, W., et al. (2002) Thiamine derivatives bind messenger RNAs directly to regulate bacterial gene expression, Nature 419, 952-956.
6. Gallego, J., et al. (2001) Targeting RNA with small molecule drugs: therapeutic promise and chemical challenges, Acc. Chem. Res. 34, 836-843.
7. Hamy, F., et al. (1997) An inhibitor of the Tat/TAR RNA interaction that effectively suppresses HIV-1 replication, Proc. Natl. Acad. Sci. U.S.A. 94, 3548-3553.
8. Mathews, D. H., et al. (2004) Incorporating chemical modification constraints into a dynamic programming algorithm for prediction of RNA secondary structure, Proc. Natl. Acad. Sci. U.S.A. 101, 7287-7292.
9. Mathews, D. H., et al. (1999) Expanded sequence dependence of thermodynamic parameters improves prediction of RNA secondary structure, J. Mol. Biol. 288, 911-940.

10. Woese, C. R., et al. (1980) Secondary structure model for bacterial 16S ribosomal RNA: phylogenetic, enzymatic and chemical evidence, Nucleic Acids Res. 8, 2275-2293.
11. Fourmy, D., et al. (1996) Structure of the A site of *Escherichia coli* 16S ribosomal RNA complexed with an aminoglycoside antibiotic, Science 274, 1367-1371.
12. Lynch, S. R., et al. (2003) Comparison of X-ray crystal structure of the 30S subunit-antibiotic complex with NMR structure of decoding site oligonucleotide-paromomycin complex, Structure (Cambridge, Mass., US) 11, 43-53.
13. Carter, A. P., et al. (2000) Functional insights from the structure of the 30S ribosomal subunit and its interactions with antibiotics, Nature 407, 340-348.
14. Kaul, M., et al. (2006) Aminoglycosideinduced reduction in nucleotide mobility at the ribosomal RNA a-site as a potentially key determinant of antibacterial activity, J. Am. Chem. Soc. 128, 1261-1271.
15. Kaul, M., et al. (2004) Fluorescencebased approach for detecting and characterizing antibiotic-induced conformational changes in ribosomal RNA: comparing aminoglycoside binding to prokaryotic and eukaryotic ribosomal RNA sequences, J. Am. Chem. Soc. 126, 3447-3453.
16. Shandrick, S., et al. (2004) Monitoring molecular recognition of the ribosomal decoding site, Angew. Chem., Int. Ed. Engl. 43, 3177-3182.
17. Thomas, J. R., et al. (2006) Biochemical and thermodynamic characterization of compounds that bind to RNA hairpin loops: toward an understanding of selectivity, Biochemistry 45, 10928-10938.
18. Thomas, J. R., et al. (2005) Size-specific ligands for RNA hairpin loops, J. Am. Chem. Soc. 127, 12434-12435.
19. Thomas, J. R., et al. (2005) The relationship between aminoglycosides' RNA binding proclivity and their antiplasmid effect on an IncB plasmid combating drug-resistant bacteria: small molecule mimics of plasmid incompatibility as antiplasmid compounds, Biochemistry 44, 6800-6808.
20. Denap, J. C., et al. (2004) Combating drug-resistant bacteria: small molecule mimics of plasmid incompatibility as antiplasmid compounds, J. Am. Chem. Soc. 126, 15402-15404.
21. Klug, S. J., et al. (1994) All you wanted to know about SELEX, Mol. Biol. Rep. 20, 97-107.
22. Joyce, G. F. (1994) In vitro evolution of nucleic acids, Curr. Opin. Struct. Biol. 4, 331-336.
23. Griffey, R. H., et al. (1999) Determinants of aminoglycoside-binding specificity for rRNA by using mass spectrometry, Proc. Natl. Acad. Sci. U.S.A. 96, 10129-10133.
24. Swayze, E. E., et al. (2002) SAR by MS: a ligand based technique for drug lead discovery against structured RNA targets, J. Med. Chem. 45, 3816-3819.
25. He, Y., et al. (2004) Synthesis and evaluation of novel bacterial rRNA-binding benzimidazoles by mass spectrometry, Bioorg. Med. Chem. Lett. 14, 695-699.
26. Seth, P. P., et al. (2005) SAR by MS: discovery of a new class of RNA-binding small molecules for the hepatitis C virus: internal ribosome entry site IIA subdomain, J. Med. Chem. 48, 7099-7102.
27. Johnson, E. C., et al. (2003) Application of NMR SHAPES screening to an RNA target, J. Am. Chem. Soc. 125, 15724-15725.
28. MacBeath, G., et al. (1999) Printing small molecules as microarrays and detecting protein-ligand interactions en masse, J. Am. Chem. Soc. 121, 7967-7968.
29. Disney, M. D., et al. (2004) Aminoglycoside microarrays to explore interactions of antibiotics with RNAs and proteins, Chemistry 10, 3308-3314.
30. Ratner, D. M., et al. (2004) Tools for glycomics: mapping interactions of carbohydrates in biological systems, Chem Bio Chem 5, 1375-1383.
31. R. N. Zuckermann, J. M. Kerr, S. B. H. Kent, W. H. Moos, J Am Chem Soc 1992, 114, 10646.
32. T. R. Chan, R. Hilgraf, K. B. Sharpless, V. V. Fokin, Org Lett 2004, 6, 2853.
33. H. C. Kolb, K. B. Sharpless, Drug Discov Today 2003, 8, 1128.
34. H. C. Kolb, M. G. Finn, K. B. Sharpless, Angew Chem Int Ed Engl 2001, 40, 2004.
35. B. Tian, R. J. White, T. Xia, S. Welle, D. H. Turner, M. B. Mathews, C. A. Thornton, RNA 2000, 6, 79.
36. R. N. Kanadia, K. A. Johnstone, A. Mankodi, C. Lungu, C. A. Thornton, D. Esson, A. M. Timmers, W. W. Hauswirth, M. S. Swanson, Science 2003, 302, 1978.
37. A. Mankodi, E. Logigian, L. Callahan, C. McClain, R. White, D. Henderson, M. Krym, C. A. Thornton, Science 2000, 289, 1769.
38. A. Mankodi, C. A. Thornton, Curr Opin Neurol 2002, 15, 545.
39. X. Lin, J. W. Miller, A. Mankodi, R. N. Kanadia, Y. Yuan, R. T. Moxley, M. S. Swanson, C. A. Thornton, Hum Mol Genet 2006, 15, 2087.
40. A. Mankodi, C. R. Urbinati, Q. P. Yuan, R. T. Moxley, V. Sansone, M. Krym, D. Henderson, M. Schalling, M. S. Swanson, C. A. Thornton, Hum Mol Genet 2001, 10, 2165.
41. J. W. Miller, C. R. Urbinati, P. Teng-Umnuay, M. G. Stenberg, B. J. Byrne, C. A. Thornton, M. S. Swanson, Embo J 2000, 19, 4439.
42. P. Henklein, H. U. Heyne, W. R. Halatsch, H. Niedrich, Synthesis-Stuttgart 1987, 166.
43. J. Roestamadji, I. Grapsas, S. Mobashery, J Am Chem Soc 1995, 117, 11060.
44. Satz, A. L.; Bruice, T. C. Biorg. Med. Chem. 2000, 8, 1871-1880.
45. Jang, H.; Fafarman, A.; Holub, J. M.; Kirshenbaum, K. Org. Lett. 2005, 7, 1951-1954.
46. Gao, F.; Yan, X.; Baetting, O. M.; Berghuis, A. M.; Auclair, K. Angew. Chem. Int. Ed. 2005, 44, 6859-6862.
47. Weber, P. J. A.; Bader, J. E.; Folkers, G.; Beck-Sickinger, A. G. Biorg. Med. Chem. Lett. 1998, 8, 597-600.

SEQUENCE LISTING

<160> NUMBER OF SEQ ID NOS: 6

<210> SEQ ID NO 1
<211> LENGTH: 46
<212> TYPE: RNA
<213> ORGANISM: Artificial Sequence
<220> FEATURE:
<223> OTHER INFORMATION: RNA sequence displaying internal loop motif

```
<400> SEQUENCE: 1
gggagagggu uuaaucugua cgaaaguacu gauuggaucc gcaagg                    46

<210> SEQ ID NO 2
<211> LENGTH: 40
<212> TYPE: RNA
<213> ORGANISM: Artificial Sequence
<220> FEATURE:
<223> OTHER INFORMATION: cassette sequence

<400> SEQUENCE: 2
gggagagggu uuaauuacga aaguaauugg auccgcaagg                           40

<210> SEQ ID NO 3
<211> LENGTH: 18
<212> TYPE: RNA
<213> ORGANISM: Artificial Sequence
<220> FEATURE:
<223> OTHER INFORMATION: stem sequence

<400> SEQUENCE: 3
gggagagggu uuaauuac                                                   18

<210> SEQ ID NO 4
<211> LENGTH: 18
<212> TYPE: RNA
<213> ORGANISM: Artificial Sequence
<220> FEATURE:
<223> OTHER INFORMATION: stem sequence

<400> SEQUENCE: 4
guaauuggau ccgcaagg                                                   18

<210> SEQ ID NO 5
<211> LENGTH: 10
<212> TYPE: RNA
<213> ORGANISM: Artificial Sequence
<220> FEATURE:
<223> OTHER INFORMATION: hairpin loop sequence

<400> SEQUENCE: 5
cgcgaaagcg                                                            10

<210> SEQ ID NO 6
<211> LENGTH: 87
<212> TYPE: RNA
<213> ORGANISM: Artificial Sequence
<220> FEATURE:
<223> OTHER INFORMATION: CUG repeat

<400> SEQUENCE: 6
cugcugcugc ugcugcugcu gcugcugcug cugcugcugc ugcugcugcu gcugcugcug     60
cugcugcugc ugcugcugcu gcugcug                                         87
```

Claim 30, Columns 63 and 64, Lines 32-60 should read:
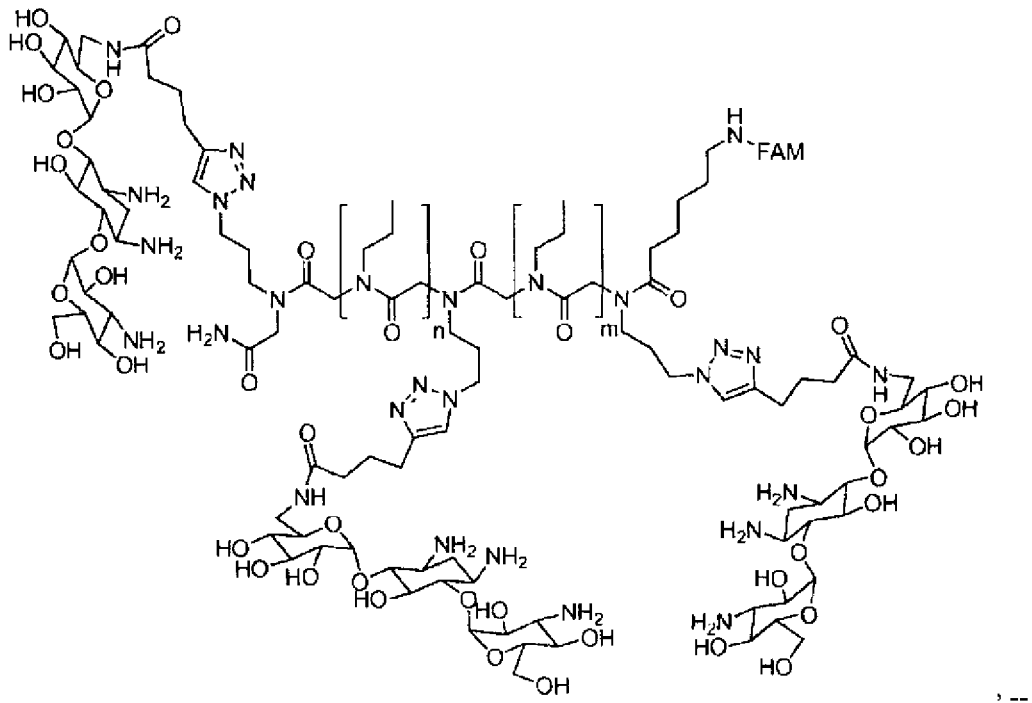
Claim 32, Column 65, Lines 35-60 should read:
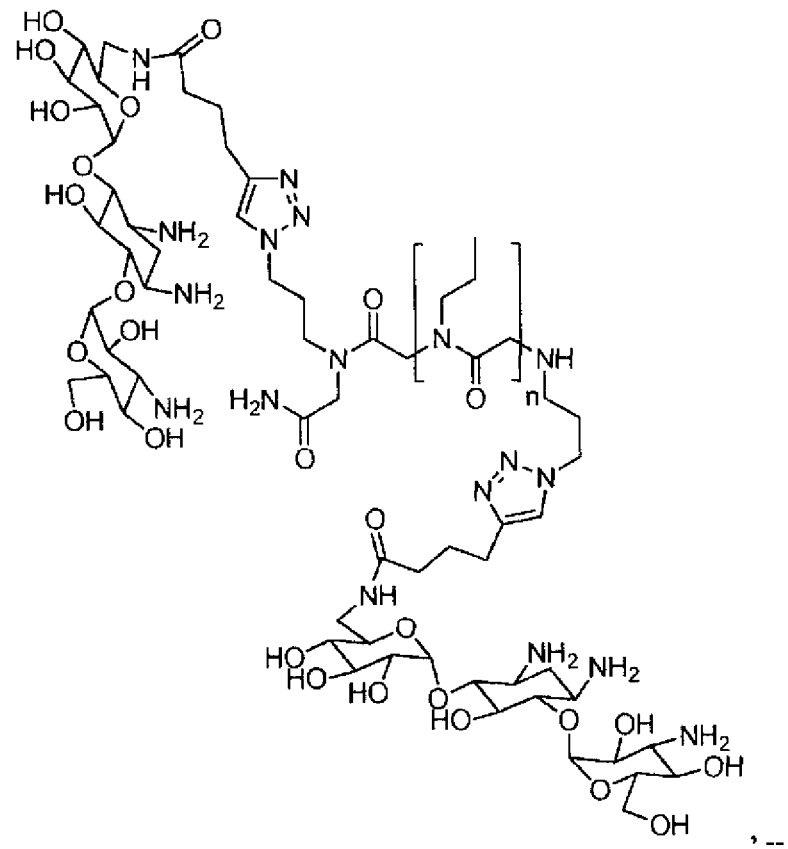

What is claimed is:

1. A compound having the formula:

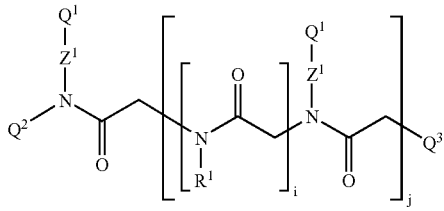

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ is the same or different and represents a ligand selected from aminoglycoside sugars and bis-benzimidazoles; $Q^2$ is an unsubstituted or substituted alkyl group; and $Q^3$ is a halogen, an alkyl group, an aryl group, or an amine.

2. A compound according to claim 1, wherein j is an integer from 2 to 10; and wherein each i is the same or different and is zero or an integer from 1 to 20.

3. A compound according to claim 1, wherein each $R^1$ is the same.

4. A compound according to claim 1, wherein each $R^1$ is the same or different and is an unsubstituted alkyl group.

5. A compound according to claim 1, wherein $Q^3$ is an amine.

6. A compound according to claim 1, wherein $Q^3$ has the formula $-NR^2R^3$, wherein $R^2$ is a hydrogen atom or an alkyl group, and wherein $R^3$ is a hydrogen atom, an alkyl group, or an alkylcarbonyl group.

7. A compound according to claim 1, wherein $Q^3$ has the formula $-NR^2R^3$, wherein $R^2$ has the formula $-Z^1-Q^1$, and wherein $R^3$ is a hydrogen atom, an alkyl group, or an alkylcarbonyl group.

8. A compound according to claim 1, wherein $Q^3$ has the formula $-NR^2R^3$, wherein $R^3$ is an alkylcarbonyl group substituted with a dye, and wherein $R^2$ is a hydrogen atom or an alkyl group.

9. A compound according to claim 1, wherein $Q^3$ has the formula $-NR^2R^3$, wherein $R^3$ is an alkylcarbonyl group substituted with a dye, and wherein $R^2$ has the formula $-Z^1-Q^1$.

10. A compound according to claim 1, wherein $Q^2$ has the formula $-CH_2-C(O)-Q^5$, wherein $Q^5$ is an amine.

11. A compound according to claim 1, wherein $Q^2$ has the formula $-CH_2-C(O)-NR^4R^5$, wherein $R^4$ is a hydrogen atom or an alkyl group, and wherein $R^5$ is a hydrogen atom or an alkyl group.

12. A compound according to claim 1, wherein $Q^2$ has the formula $-CH_2-C(O)-NR^4R^5$, wherein $R^4$ is an alkyl group substituted with a dye, and wherein $R^5$ is a hydrogen atom.

13. A compound according to claim 1, wherein $Q^2$ has the formula $-CH_2-C(O)-NR^4R^5$, wherein $R^4$ is a hydrogen atom, and wherein $R^5$ is a hydrogen atom.

14. A compound according to claim 1, wherein each $Z^1$ is the same or different and has the formula: $-Z^2-Z^3-Z^4$, wherein $Z^2$ is an alkylene moiety, $Z^4$ is an alkylene moiety, and $Z^3$ is a linkage selected from an amide, an ester, an ether, and a triazole ring.

15. A compound according to claim 14, wherein $Z^3$ is a triazole ring linkage having one of the following formulae:

16. A compound according to claim 14, wherein $Z^1$ has one of the following formulae:

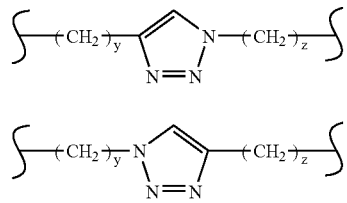

wherein y is an integer from 1 to 6, and wherein z is an integer from 1 to 6.

17. A compound according to claim 1, wherein each $Q^1$ is the same or different and is an aminoglycoside sugar.

18. A compound according to claim 1, wherein each $Q^1$ is the same or different and is selected from kanamycin As, tobramycins, neamines, and neomycins.

19. A compound comprising a peptoid polymer backbone and two or more pendant ligands, wherein each of said two or more pendant ligands are bound to said polymer backbone, and wherein each of said two or more pendant ligands are the same or different and are selected from aminoglycoside sugars and bis-benzimidazoles.

20. A compound according to claim 19, wherein each of said two or more pendant ligands are the same.

21. A compound according to claim 19, wherein each of said two or more pendant ligands are aminoglycoside sugars.

22. A compound according to claim 19, wherein each of said two or more pendant ligands are selected from kanamycin As, tobramycins, neamines, and neomycins.

23. A compound according to claim 1, wherein $Q^3$ has the formula $-NR^2R^3$, $R^2$ has the formula $-Z^1-Q^1$, and $R^3$ is a hydrogen atom.

24. A compound according to claim 23, wherein the compound has the following structure:

45
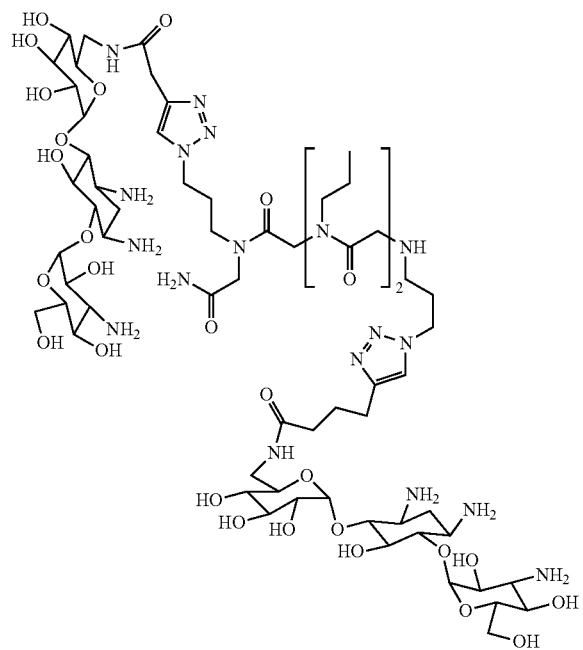
46
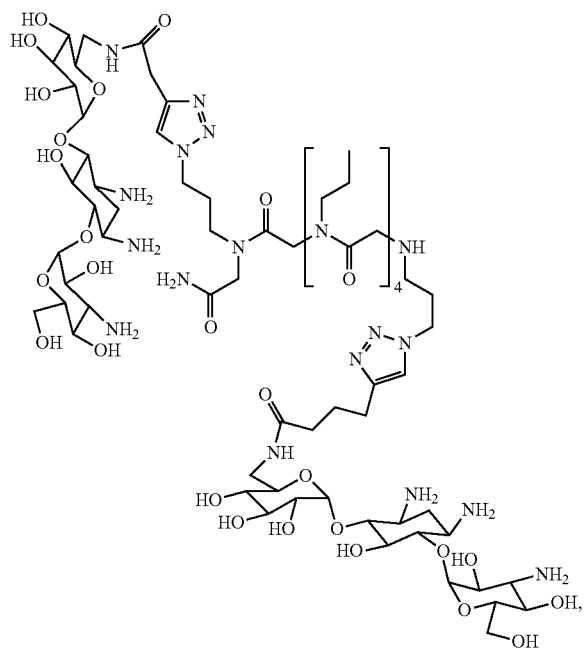
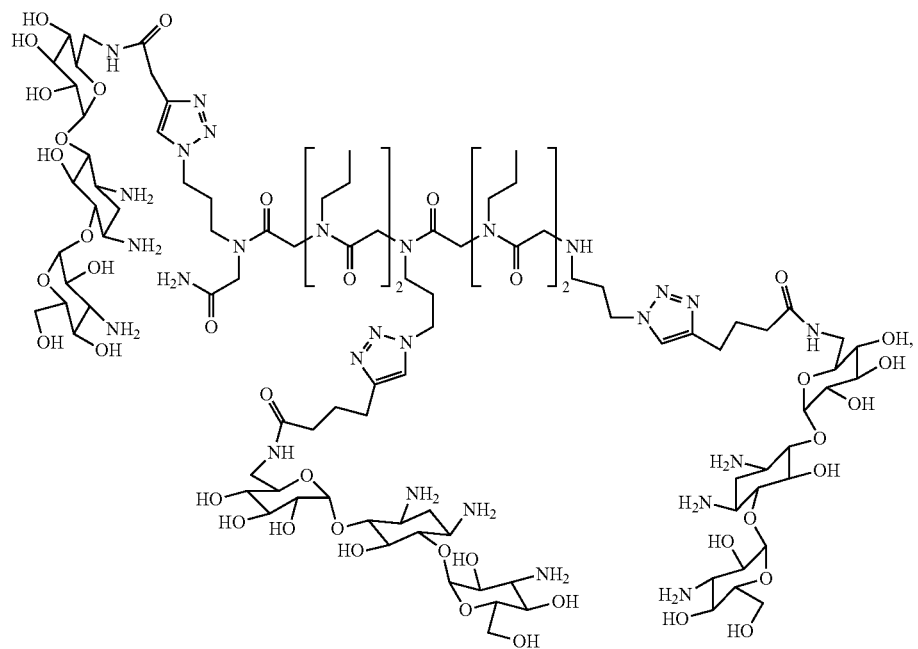

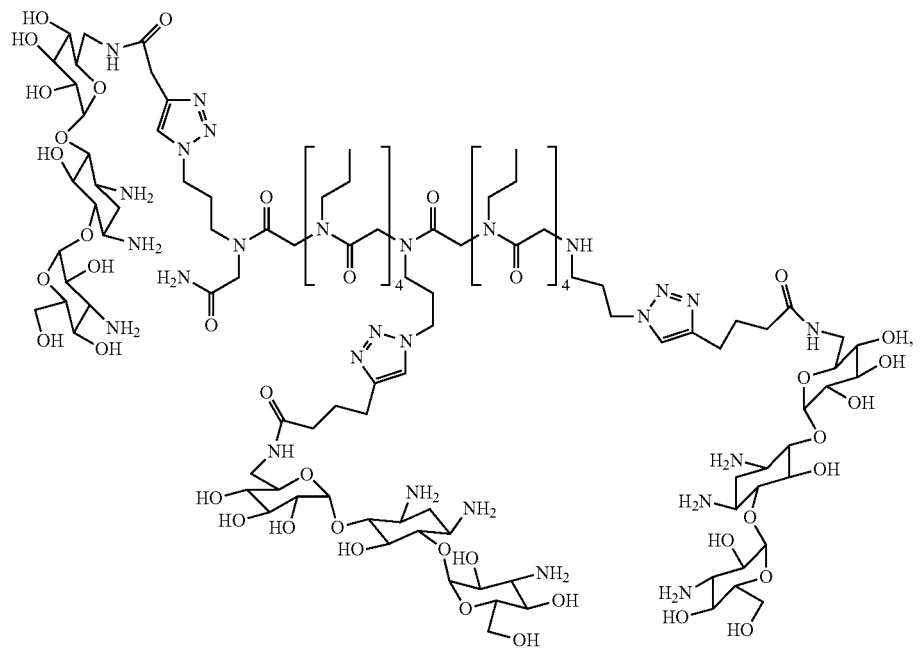
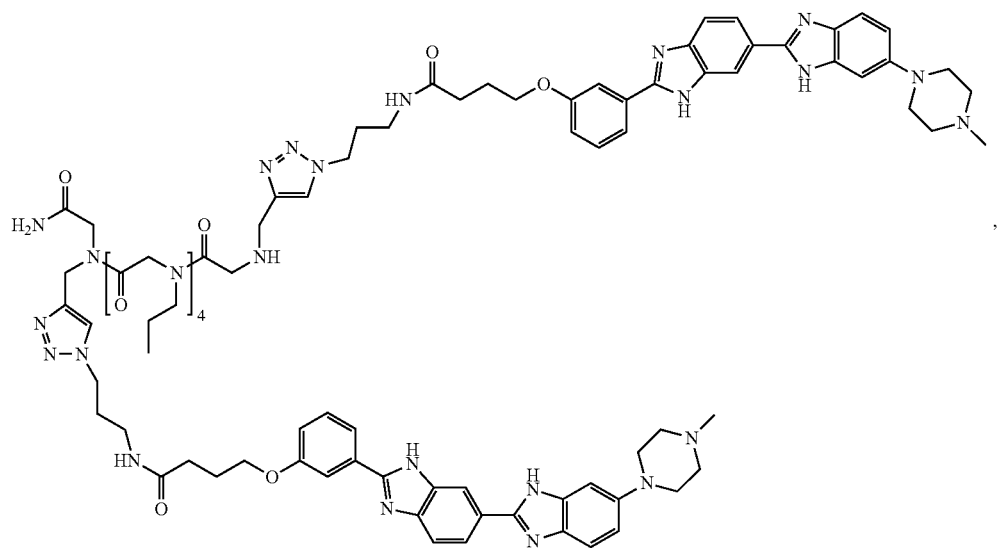
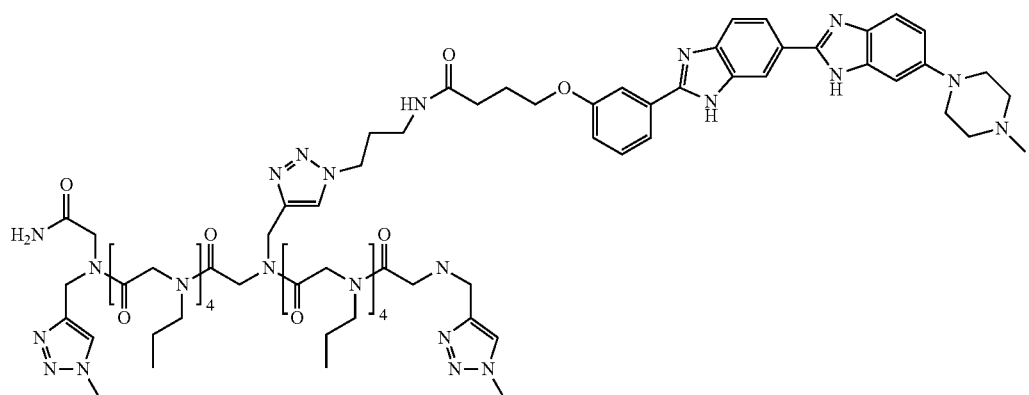

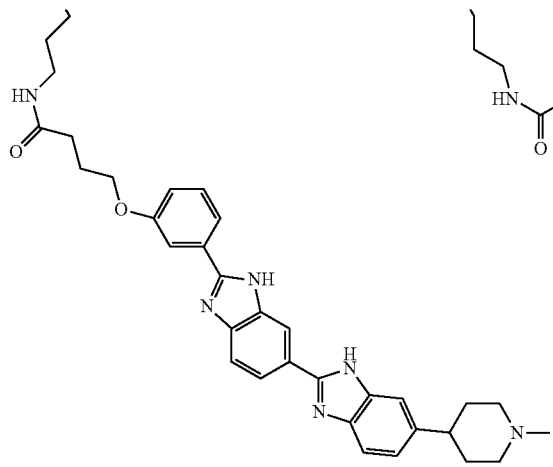
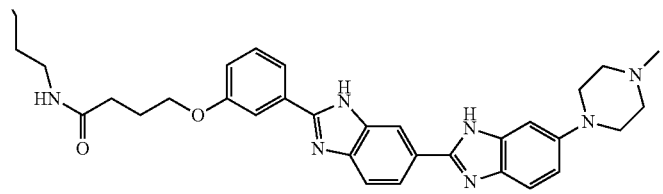
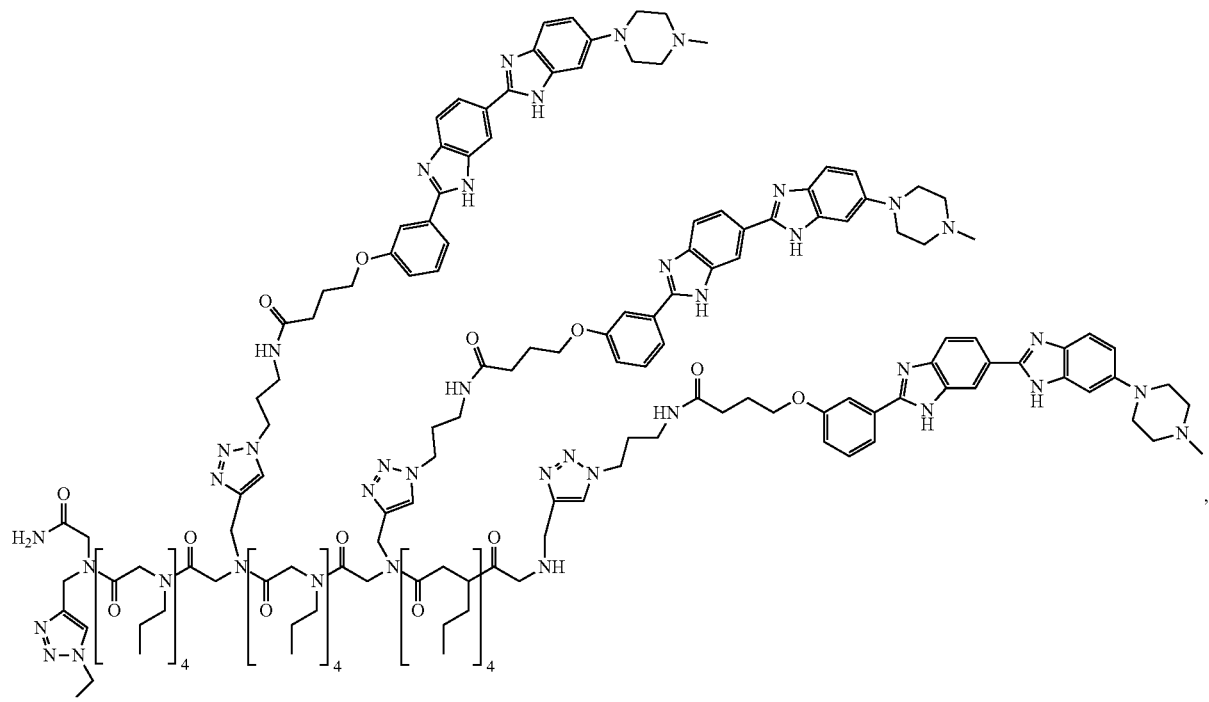
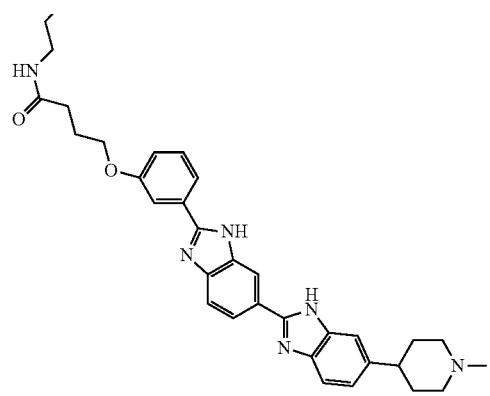

or
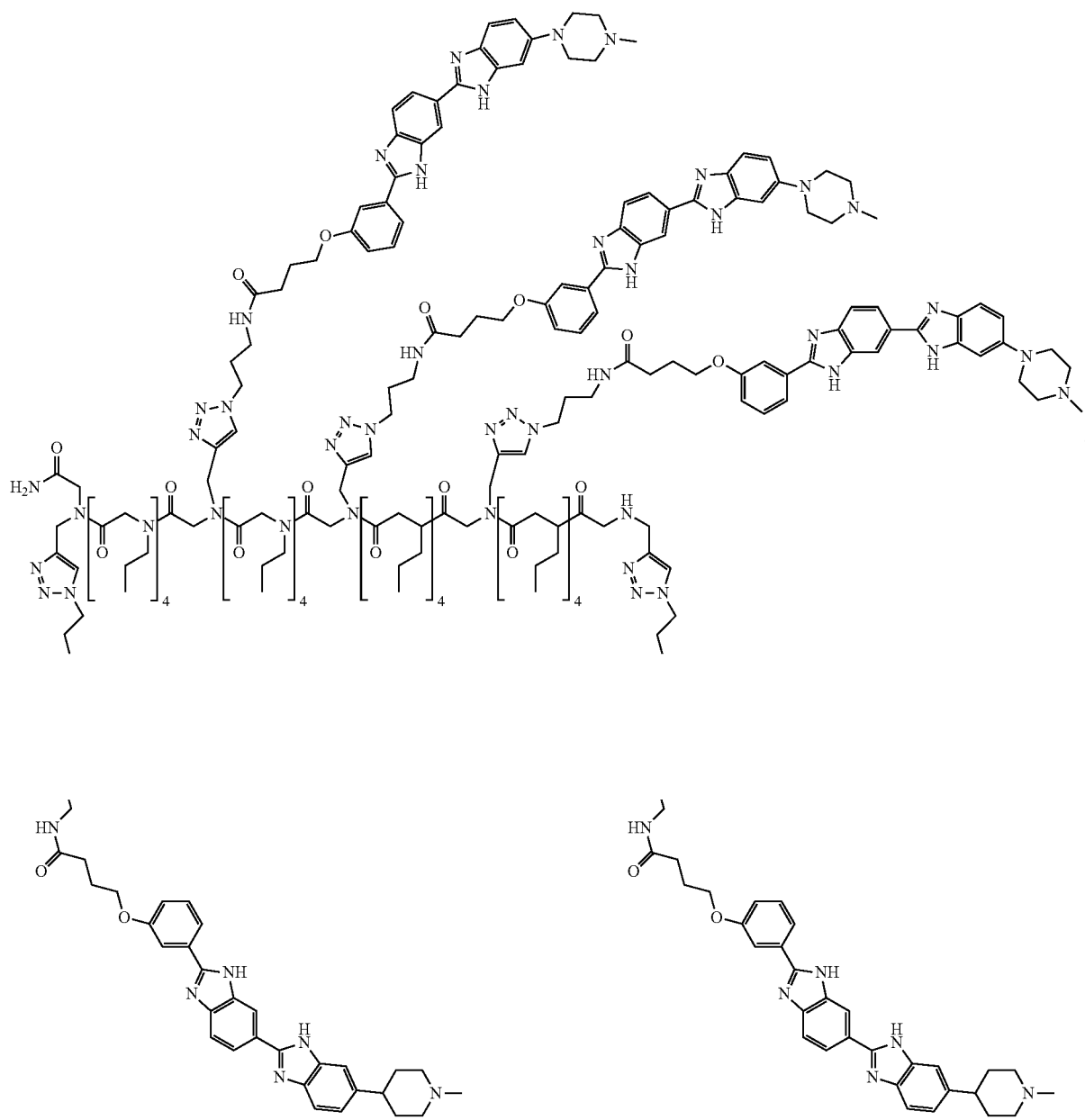
25. A compound according to claim 1, wherein $Q^3$ has the formula —$NR^2R^3$, $R^2$ has the formula -$Z^1$-$Q^1$, and $R^3$ is an alkylcarbonyl group substituted with a label.
26. A compound according to claim 25, wherein the label is a dye, a radioactive label, or enzymatic label.
27. A compound according to claim 25, wherein the compound has the following structure:

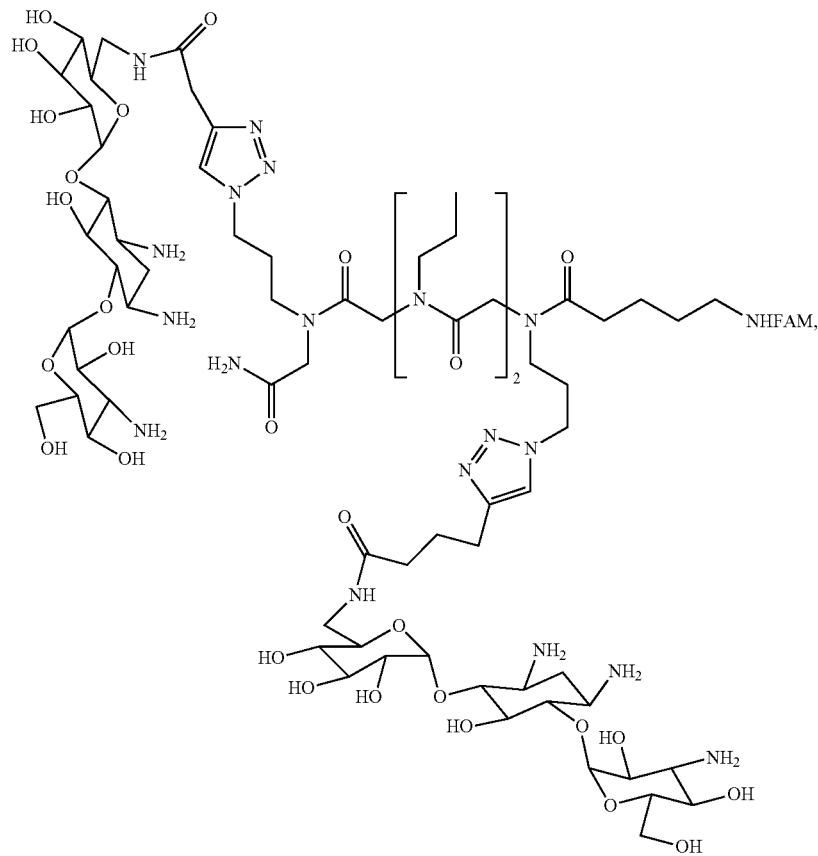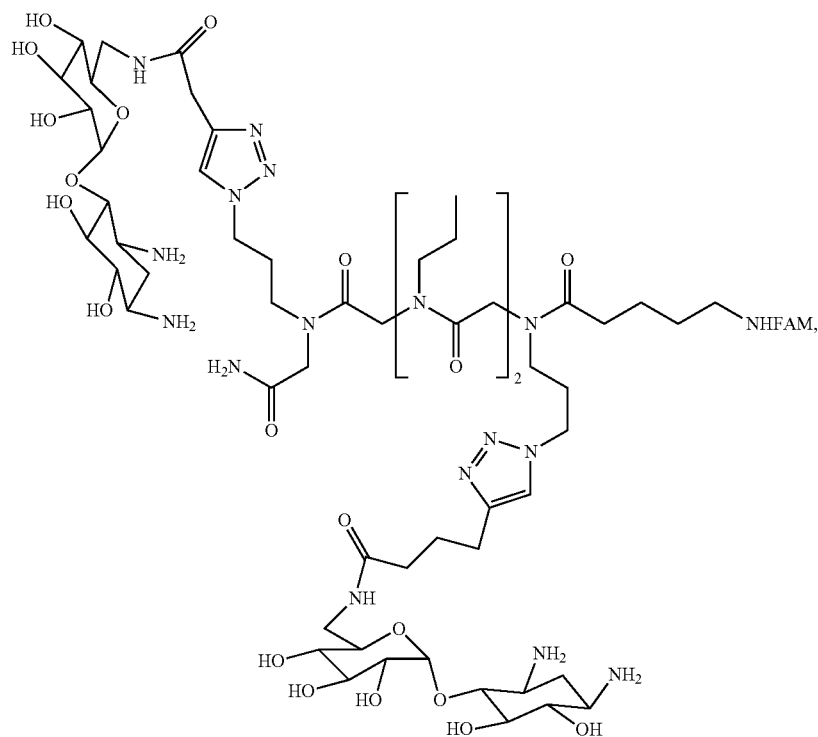

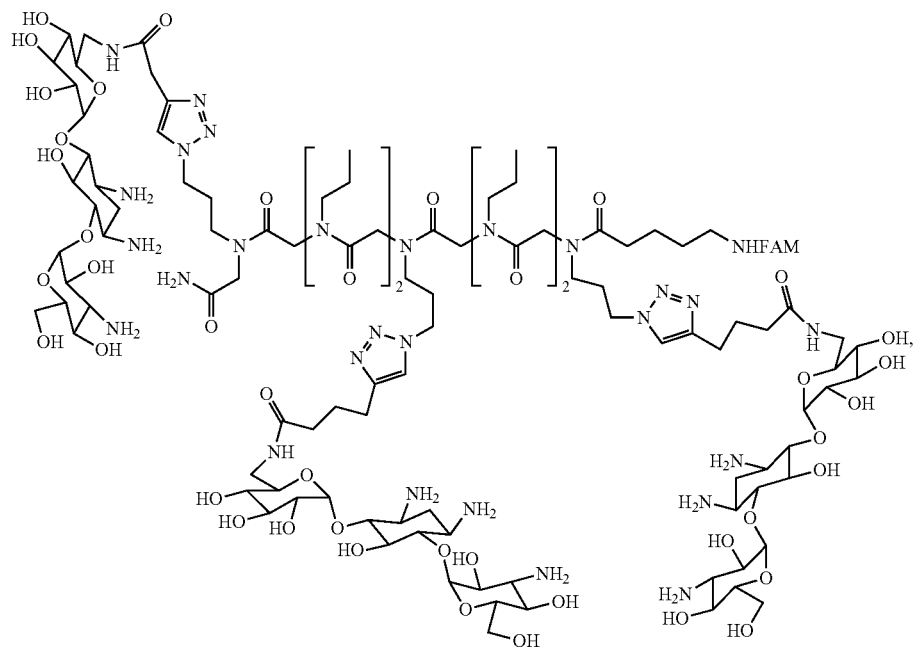
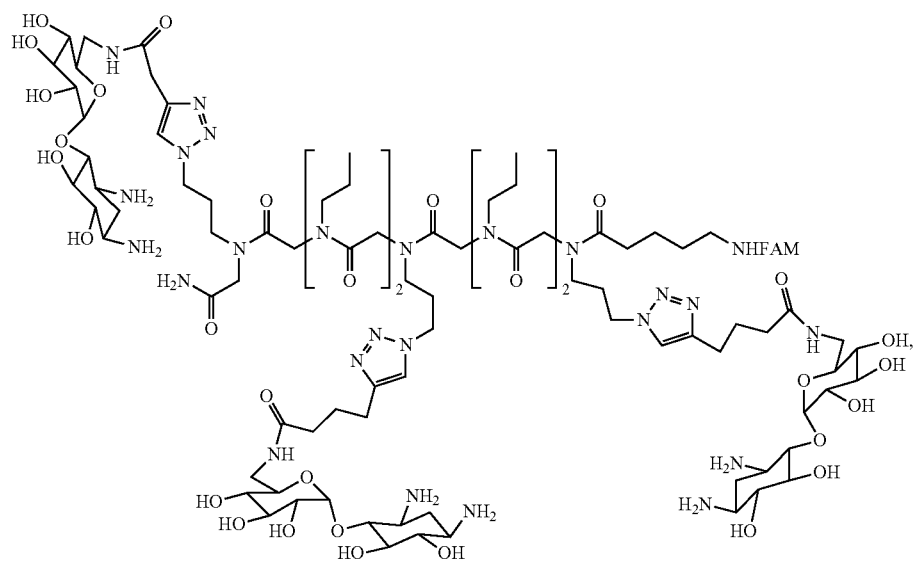

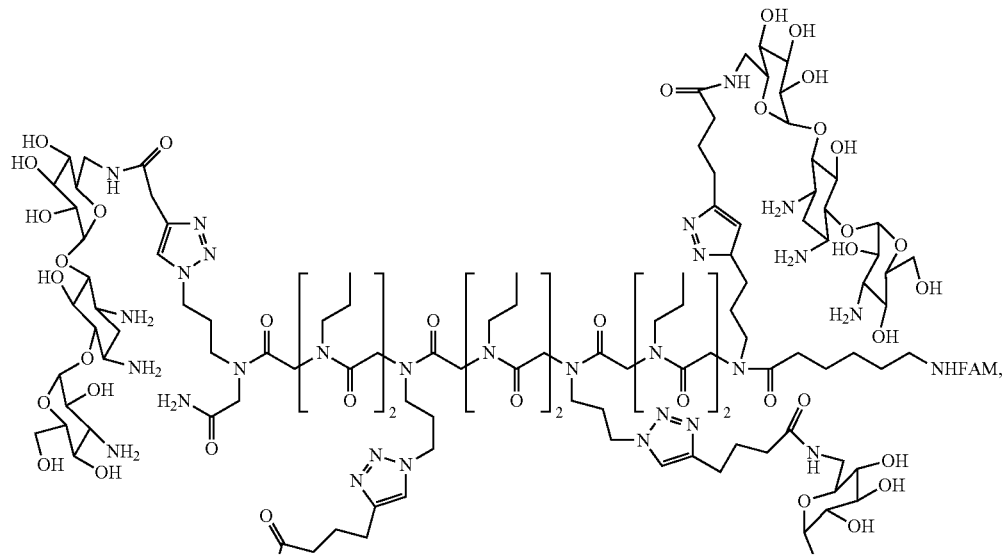
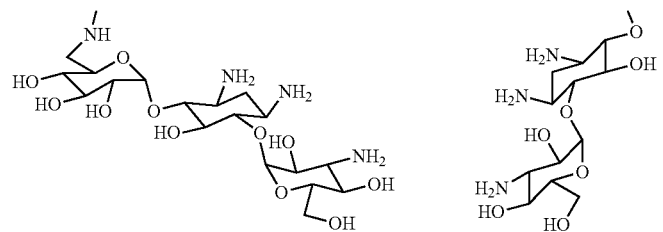
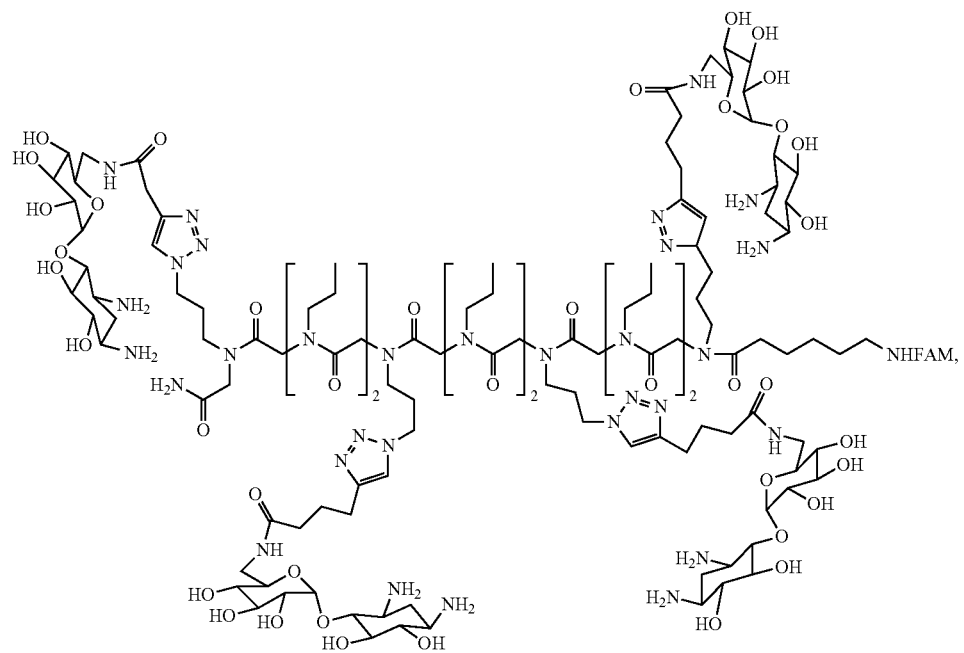

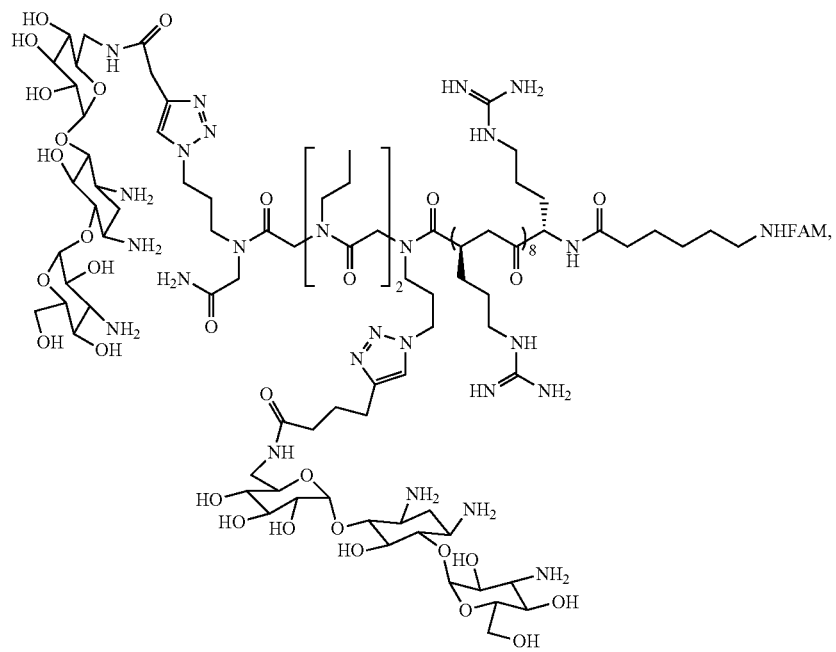
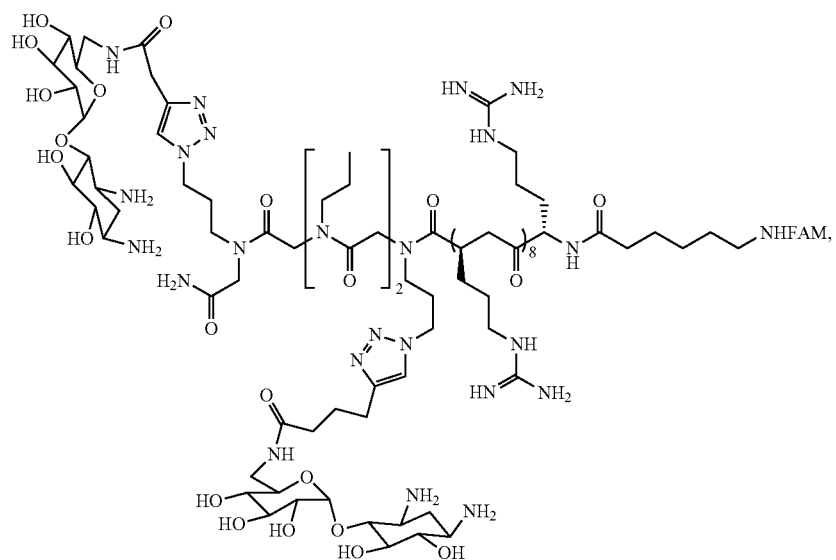
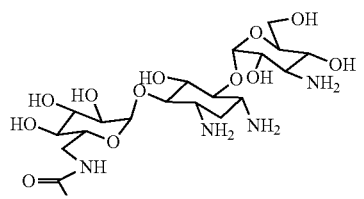

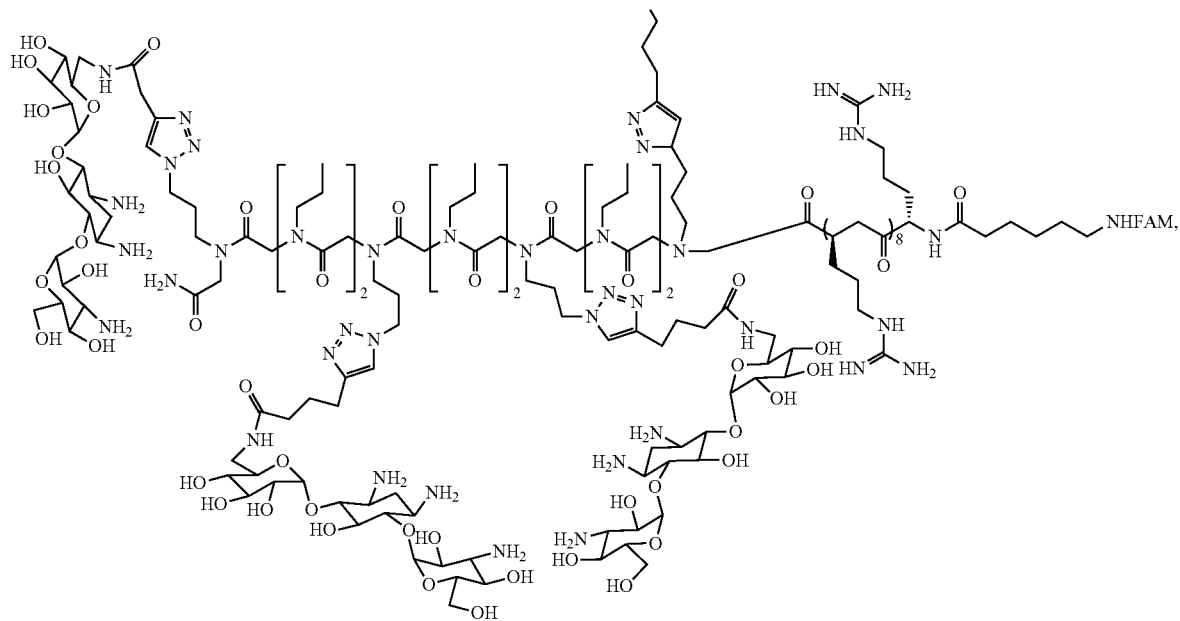
or
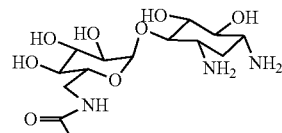
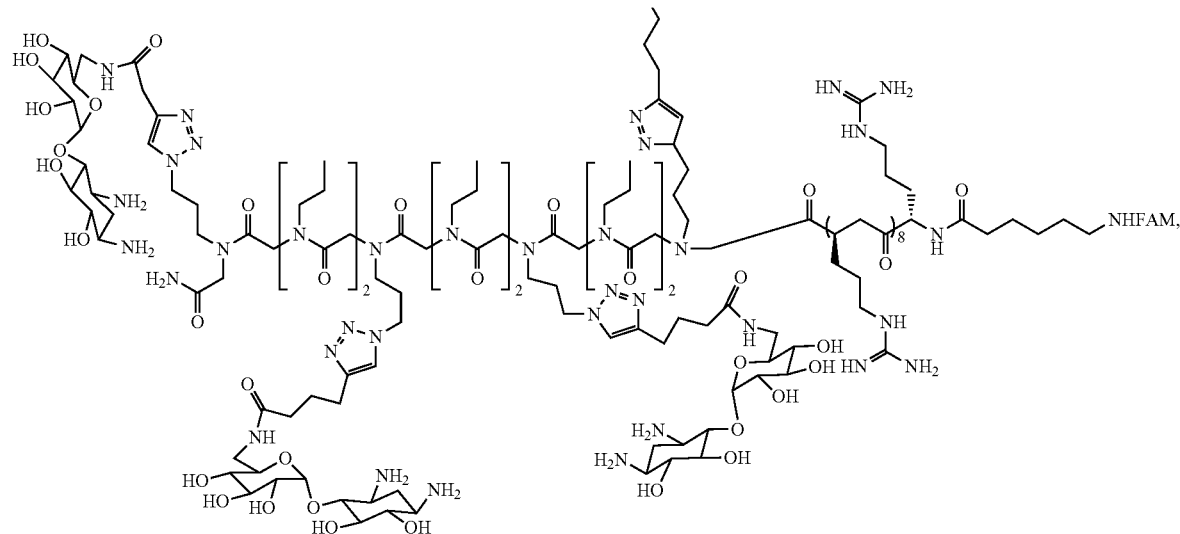
where FAM is a carboxyfluorescein.

28. A compound having the formula:

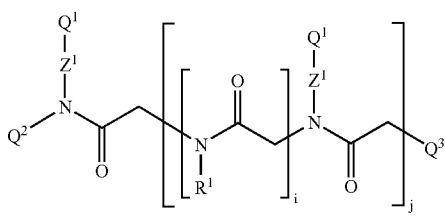

wherein j is an integer from 1 to 100; each i is the same or different and is zero or an integer from 1 to 100; each $Z^1$ represents the same or different linking moiety and has one of the following formulae:

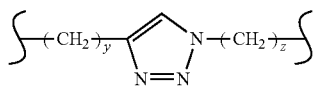

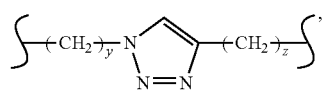

wherein y is an integer from 1 to 6, and wherein z is an integer from 1 to 6; each $R^1$ is the same or different and represents an alkyl group or an aryl group; each $Q^1$ is the same or different and represents a ligand selected from proteins, polypeptides, carbohydrates, non-nucleic acid biopolymers, peptoids, whole cells, aminoglycoside sugars, and bis-benzimidazoles; $Q^2$ is an unsubstituted or substituted alkyl group; and $Q^3$ is a halogen, an alkyl group, an aryl group, or an amine.

29. A compound having the formula:

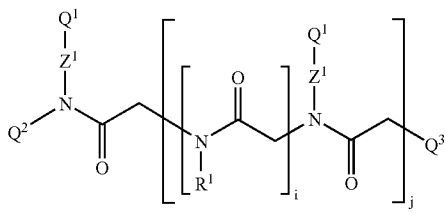

wherein j is an integer from 1 to 100; each i is the same or different and is zero or an integer from 1 to 100; each $Z^1$ represents the same or different linking moiety; each $R^1$ is the same or different and represents an alkyl group or an aryl group; each $Q^1$ is the same or different and represents a ligand selected from proteins, polypeptides, carbohydrates, non-nucleic acid biopolymers, peptoids, whole cells, aminoglycoside sugars, and bis-benzimidazoles; $Q^2$ is an unsubstituted or substituted alkyl group; and $Q^3$ is a halogen, an alkyl group, an aryl group, or an amine.

30. The compound of claim 19, wherein the compound has the following structure:

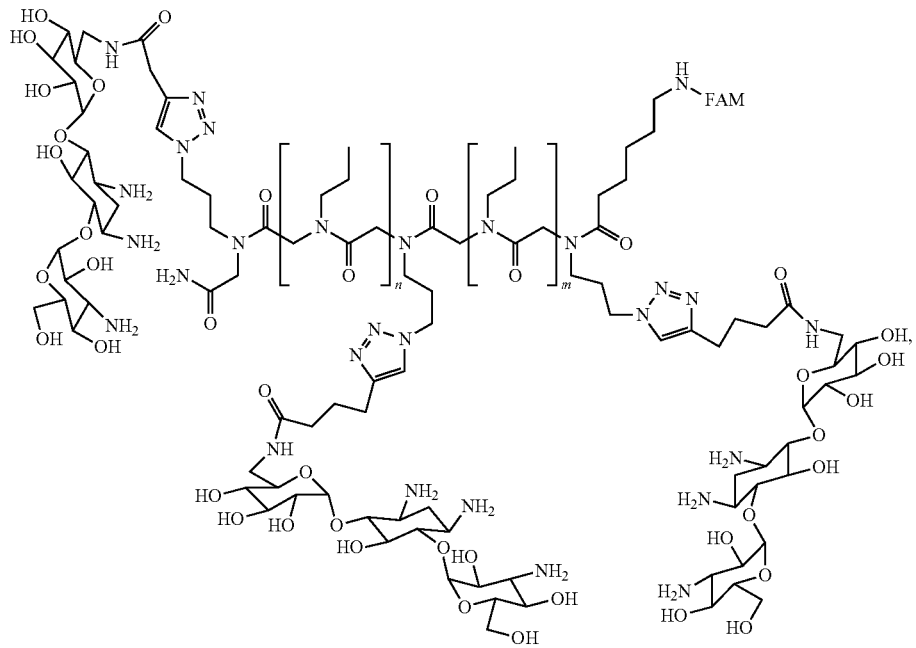

wherein m equals 0 and n equals 3, m equals 0 and n equals 4, m equals 0 and n equals 6, m equals 0 and n equals 8, m equals 0 and n equals 19, m equals 3 and n equals 3, or m equals 9 and n equals 8.

31. The compound of claim 19, wherein the compound has the following structure:

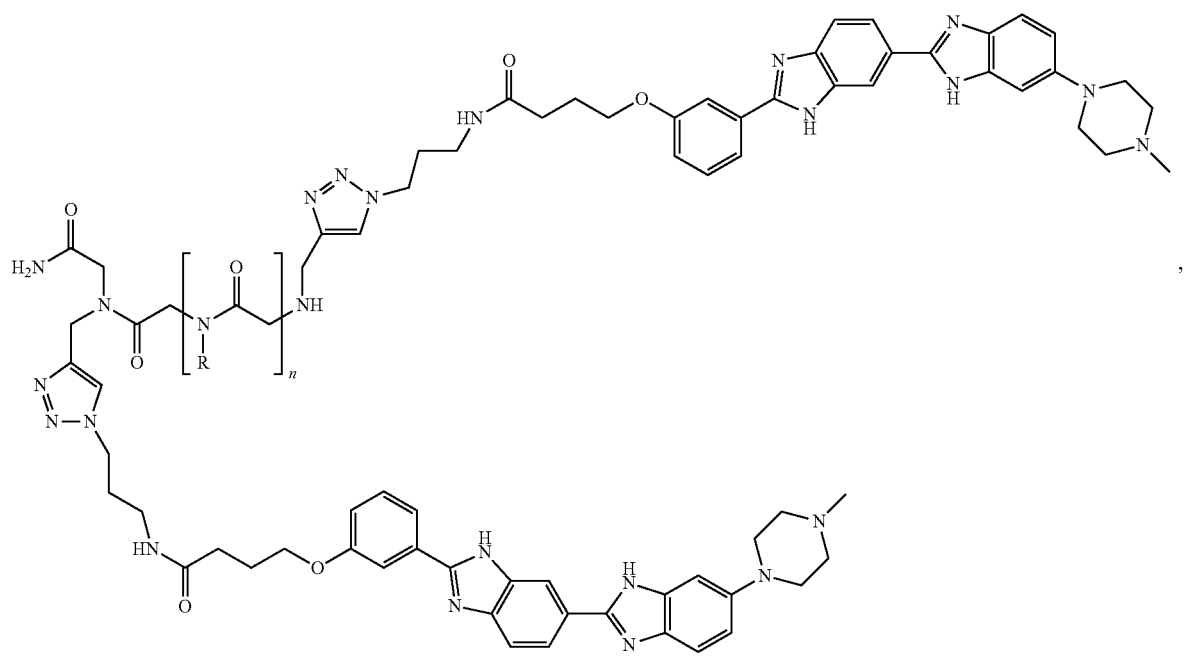
wherein R is n-propyl and n equals 4, R is n-propyl and n equals 8, R is n-propyl and n equals 12, R is n-propyl and n equals 16, or R is methyl and n equals 16.
32. The compound of claim 19, wherein the compound has the following structure:
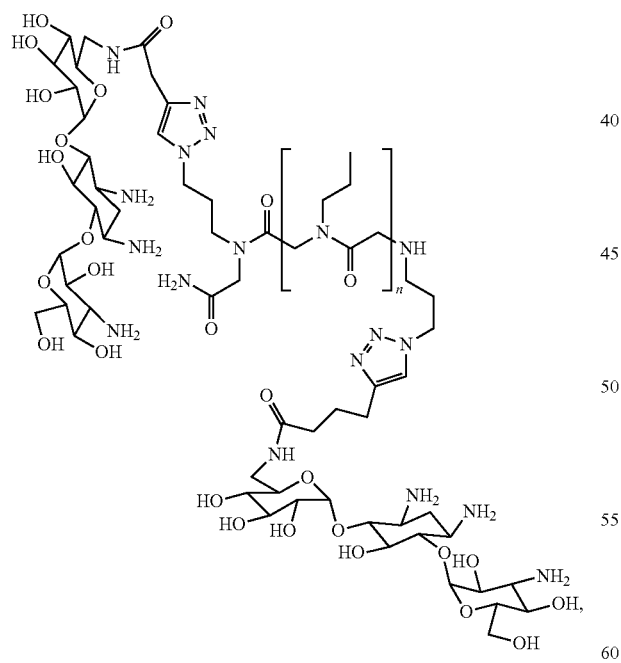
wherein n is equal to 4, 8, or 12.
* * * * *

UNITED STATES PATENT AND TRADEMARK OFFICE
CERTIFICATE OF CORRECTION

PATENT NO. : 9,150,612 B2  Page 1 of 10
APPLICATION NO. : 12/072291
DATED : October 6, 2015
INVENTOR(S) : Disney et al.

It is certified that error appears in the above-identified patent and that said Letters Patent is hereby corrected as shown below:

IN THE CLAIMS

Claim 24, Column 45 and 46 should read:

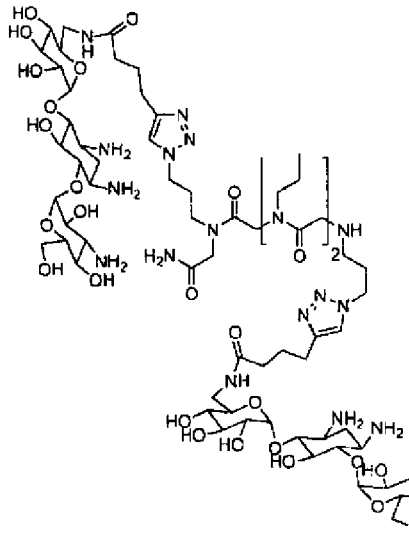 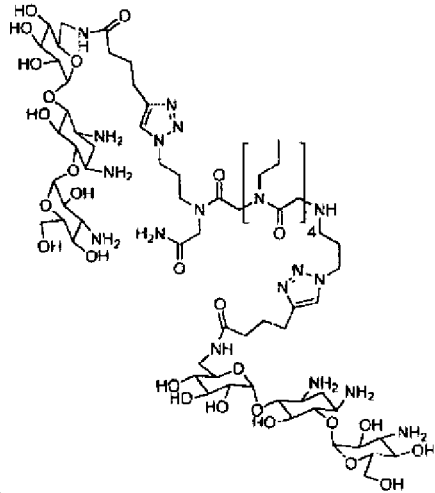

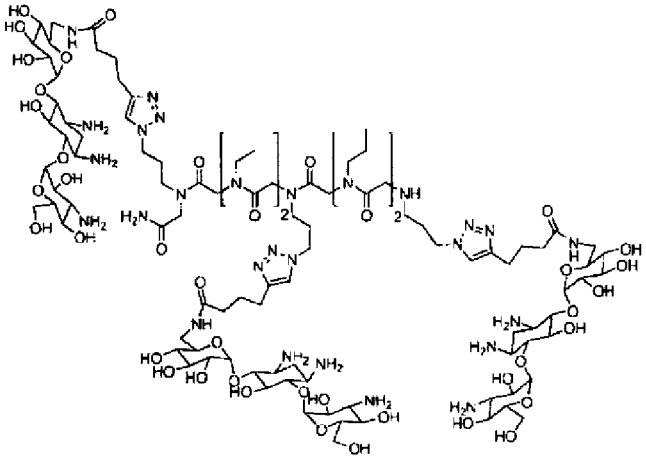

--  .  --

Signed and Sealed this
Fifth Day of April, 2016

Michelle K. Lee
*Director of the United States Patent and Trademark Office*

CERTIFICATE OF CORRECTION (continued)
U.S. Pat. No. 9,150,612 B2

Claim 24, Columns 47 and 48 should read:
-- -continued

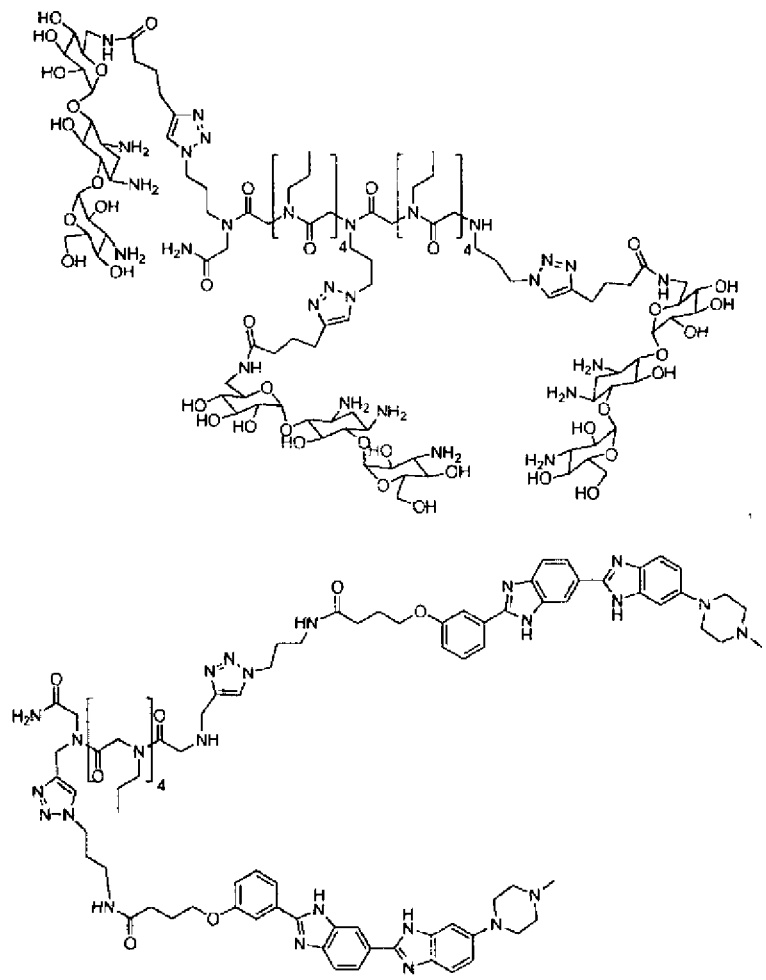

CERTIFICATE OF CORRECTION (continued)
U.S. Pat. No. 9,150,612 B2

Page 3 of 10

Claim 24, Columns 47 and 48 (continued) should read:

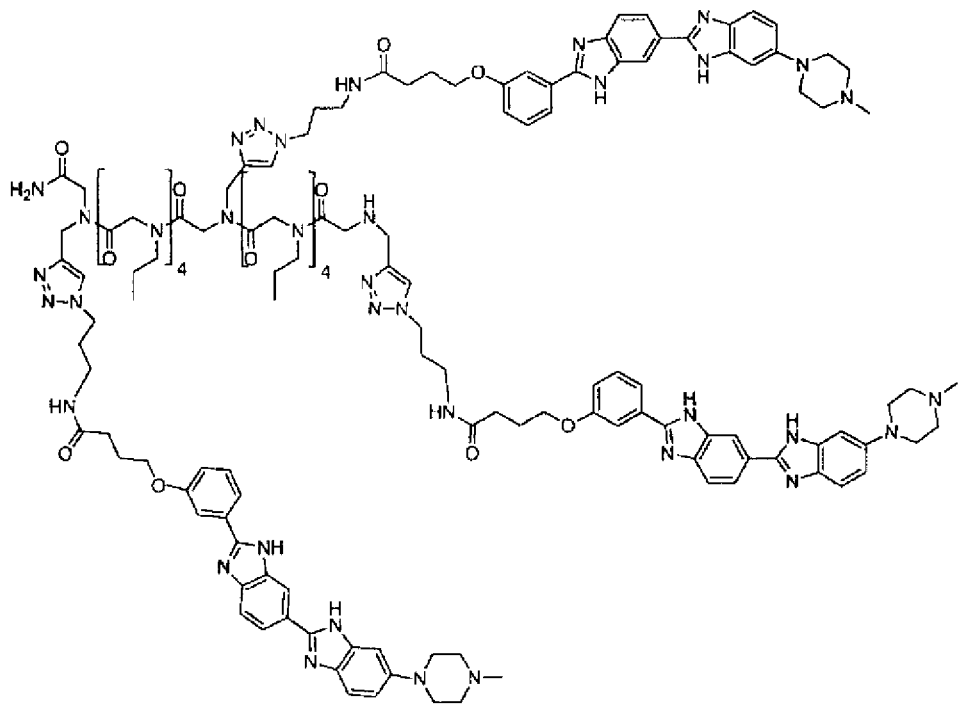

--                                                                  , --

Claim 24, Columns 49 and 50 should read:
-- -continued

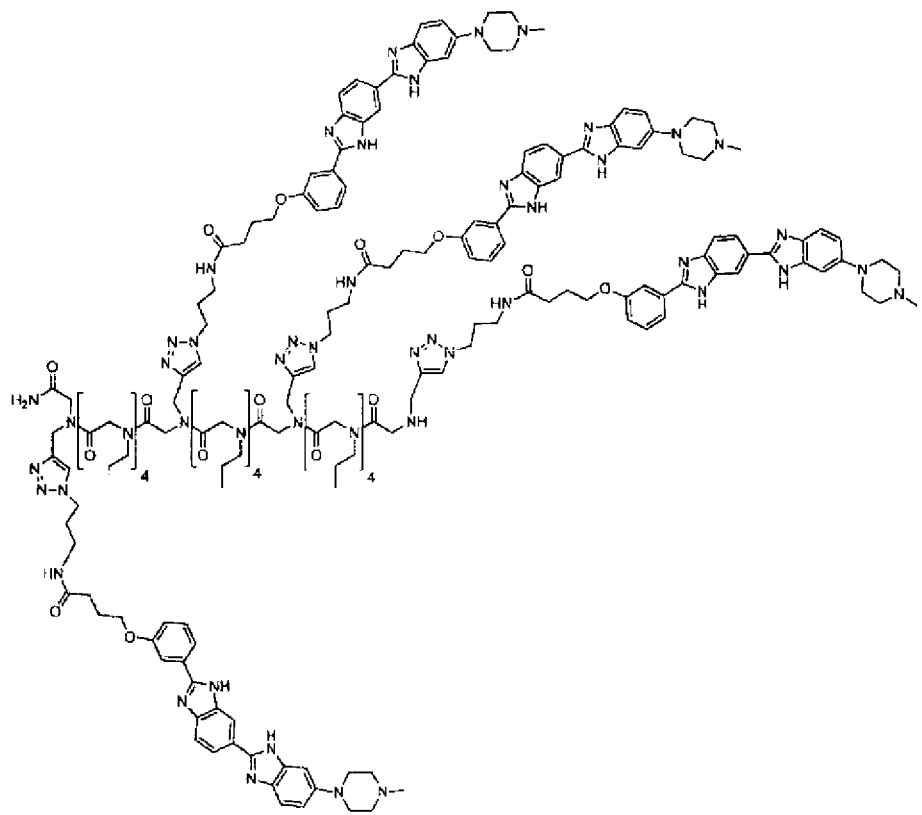

, or --

CERTIFICATE OF CORRECTION (continued)

Claim 24, Columns 51 and 52, Lines 2-63 should read:

-- -continued

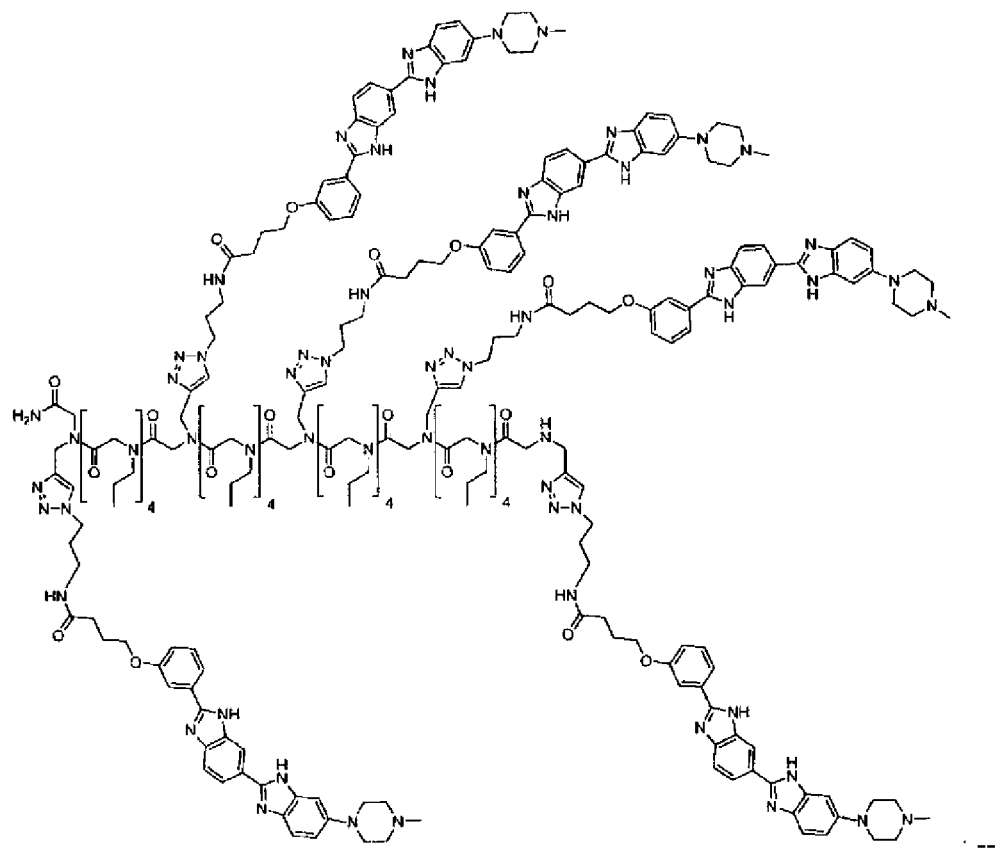

CERTIFICATE OF CORRECTION (continued)
U.S. Pat. No. 9,150,612 B2

Claim 27, Columns 53 and 54 should read:

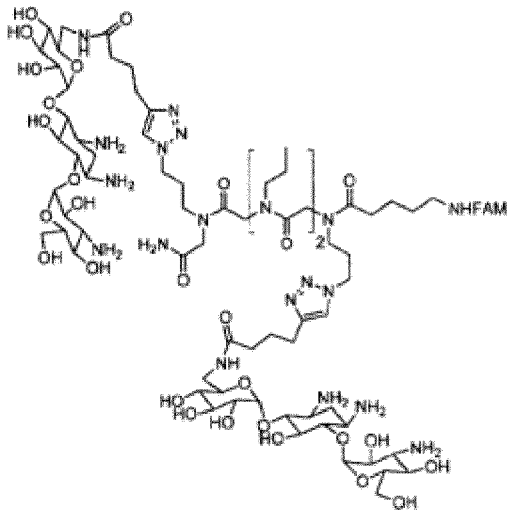

--

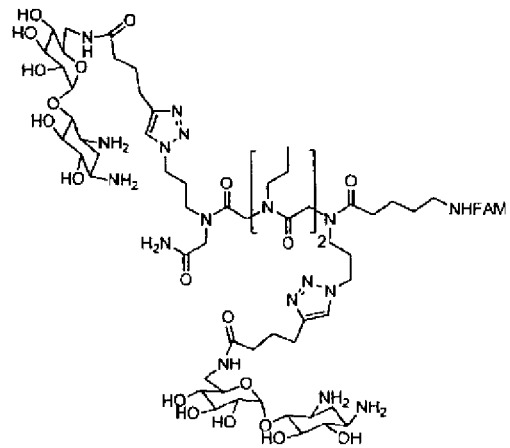

, --

Claim 27, Columns 55 and 56 should read:
-- -continued
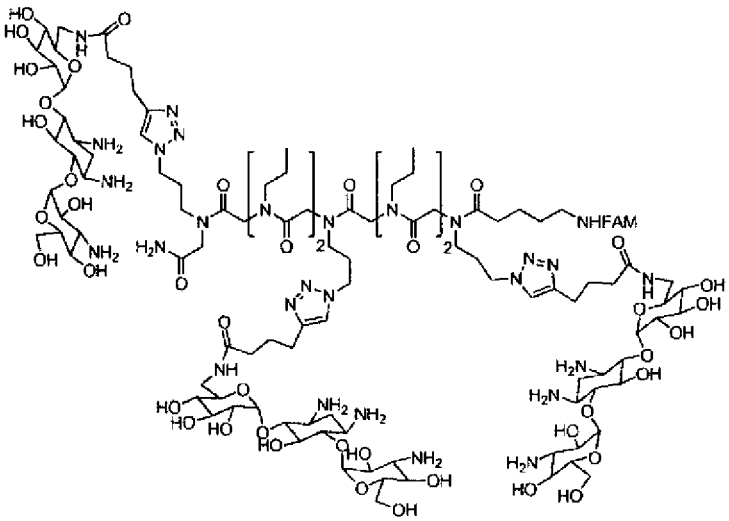
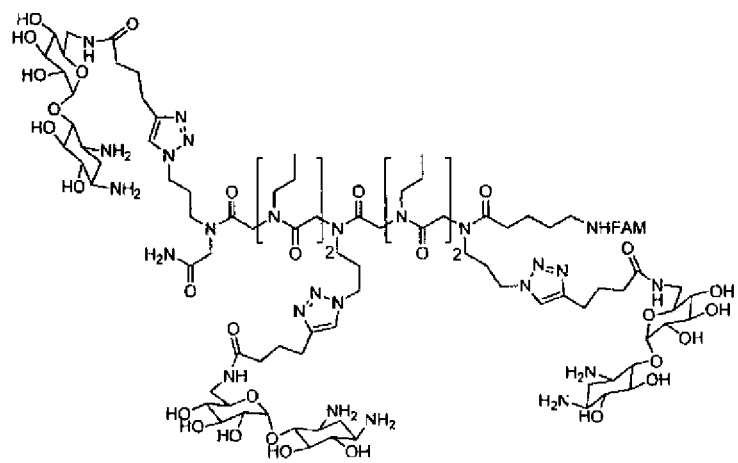
, --

Claim 27, Columns 57 and 58 should read:
-- -continued
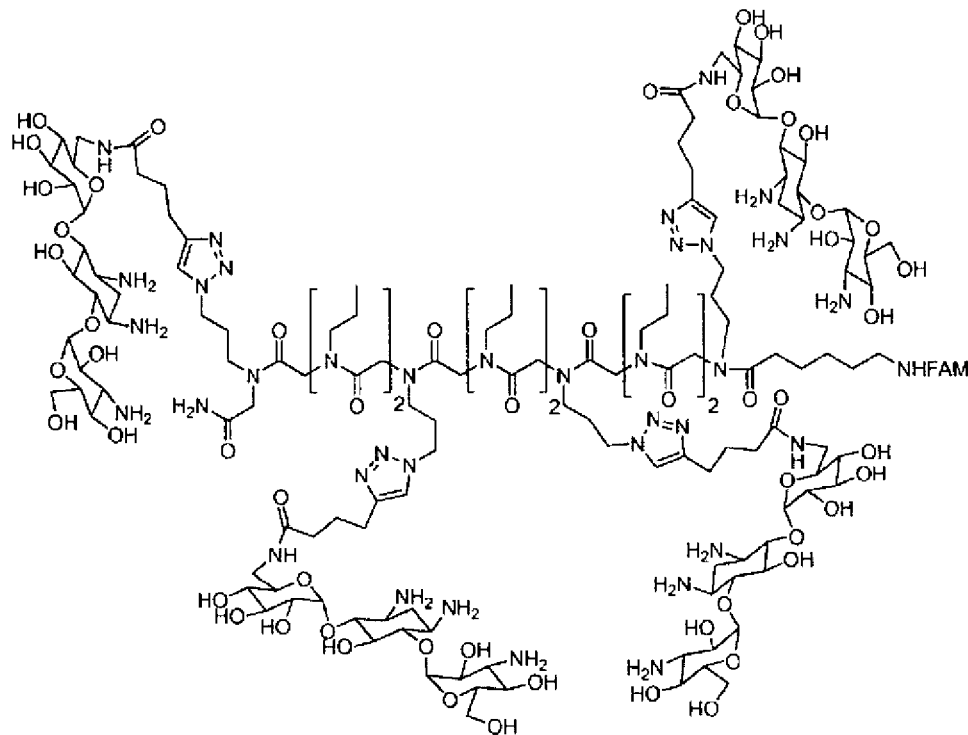
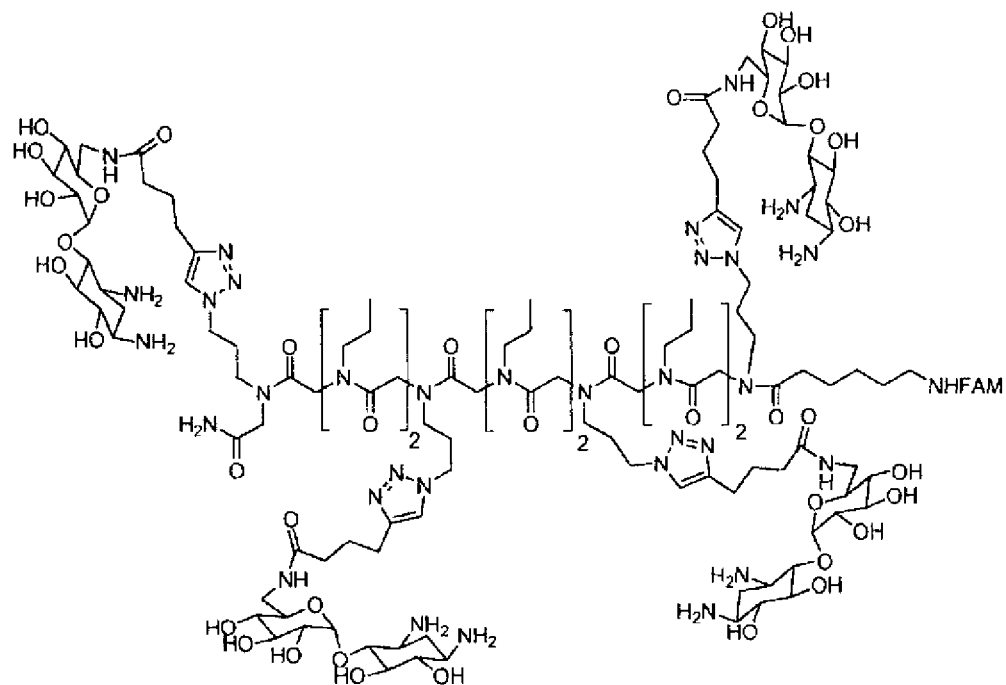
,  --

CERTIFICATE OF CORRECTION (continued)
U.S. Pat. No. 9,150,612 B2

Claim 27, Columns 59 and 60 should read:
-- -continued

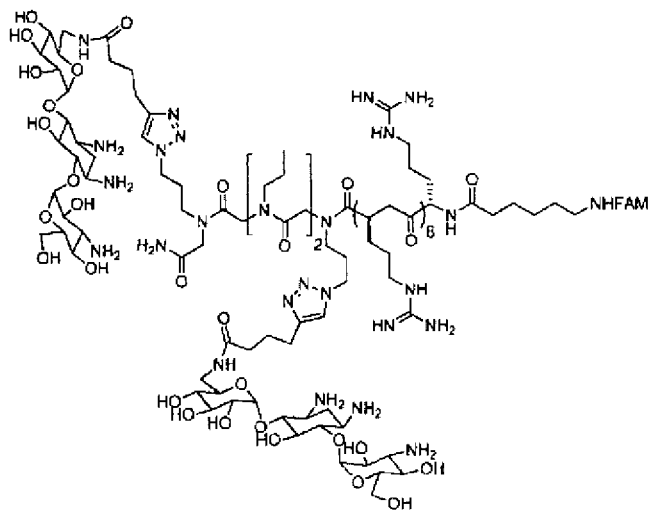

,

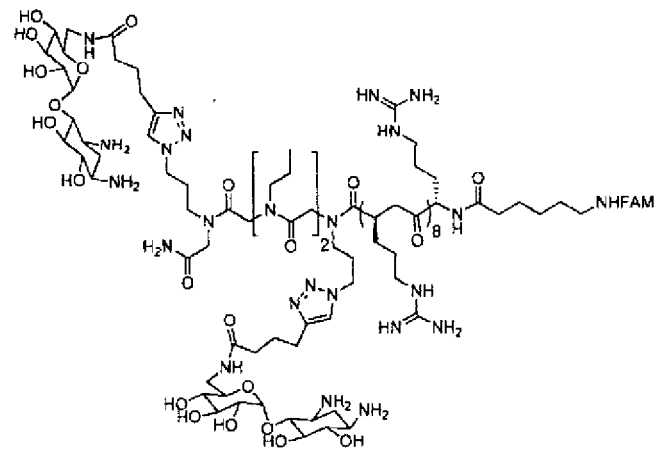

--

CERTIFICATE OF CORRECTION (continued)
U.S. Pat. No. 9,150,612 B2

Claim 27, Columns 61 and 62 should read:
-- -continued

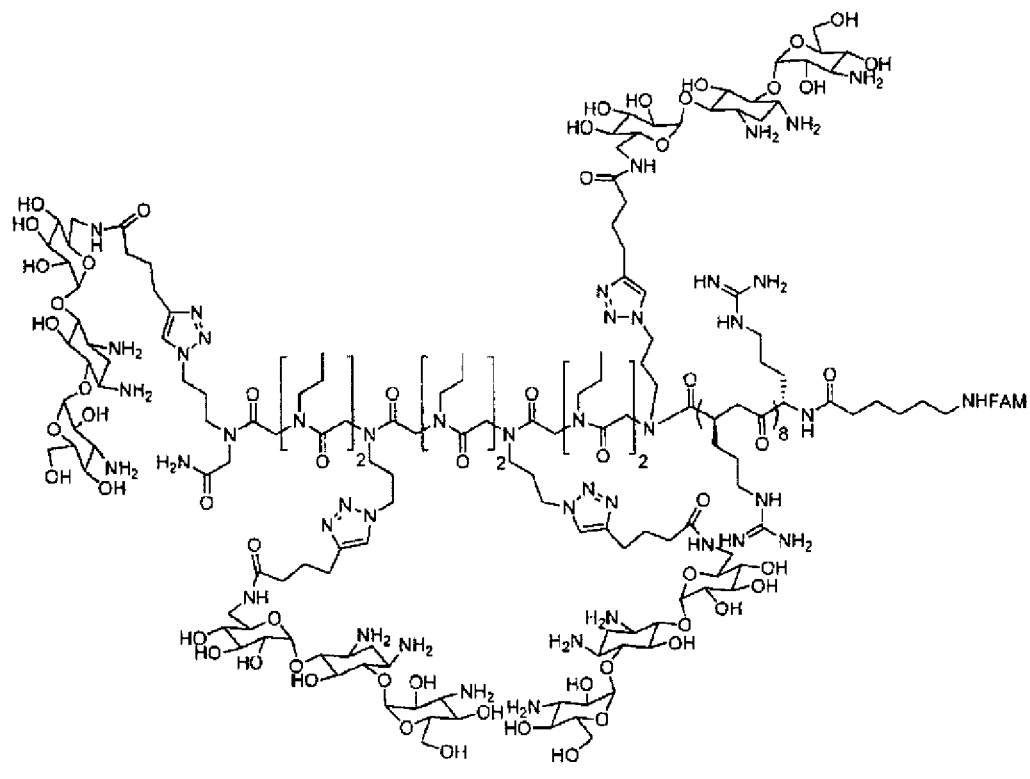

, or

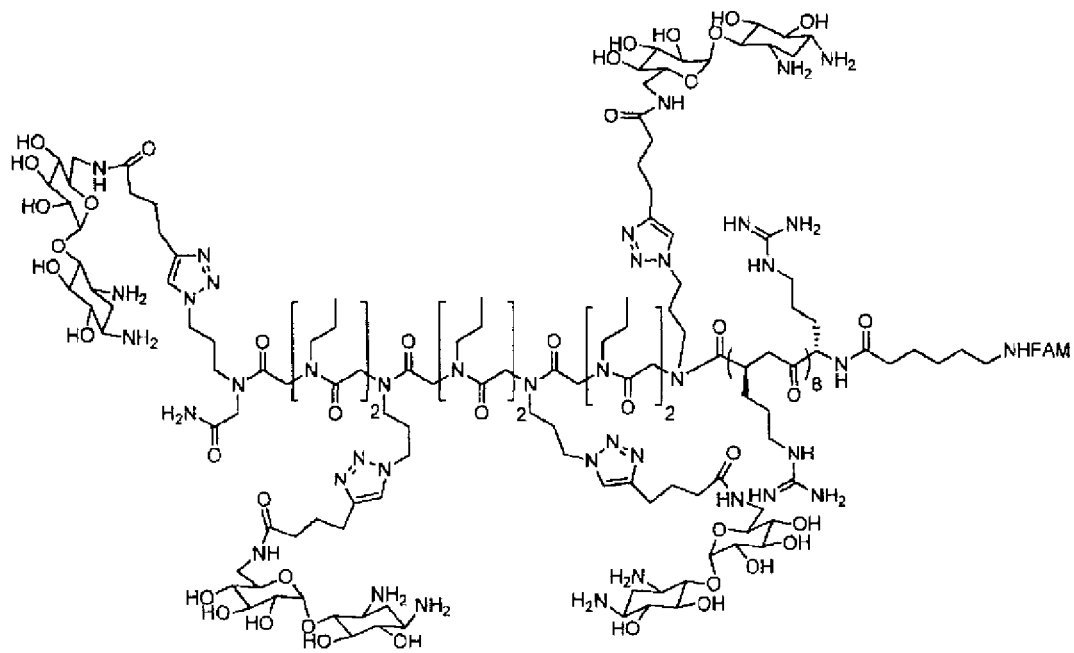

, --

Claim 29, Column 64, Line 19 should read:
--different and an integer from 1 to 100; each $Z^1$--